(12) United States Patent
Arnett et al.

(10) Patent No.: US 12,370,354 B2
(45) Date of Patent: Jul. 29, 2025

(54) COUPLING MECHANISMS FOR MEDICAL DEVICES

(71) Applicant: Boston Scientific Medical Device Limited, Ballybrit (IE)

(72) Inventors: Jeffery Arnett, Gilbert, AZ (US); Moussa Chehade, Toronto (CA); John Paul Urbanski, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 1075 days.

(21) Appl. No.: 17/053,414

(22) PCT Filed: May 8, 2019

(86) PCT No.: PCT/IB2019/053755
§ 371 (c)(1),
(2) Date: Nov. 6, 2020

(87) PCT Pub. No.: WO2019/215623
PCT Pub. Date: Nov. 14, 2019

(65) Prior Publication Data
US 2021/0228858 A1    Jul. 29, 2021

Related U.S. Application Data

(60) Provisional application No. 62/668,700, filed on May 8, 2018.

(51) Int. Cl.
*A61M 39/10* (2006.01)
*A61M 25/06* (2006.01)
*A61M 39/02* (2006.01)

(52) U.S. Cl.
CPC ........ *A61M 39/10* (2013.01); *A61M 25/0662* (2013.01); *A61M 39/1011* (2013.01);
(Continued)

(58) Field of Classification Search
CPC .............. A61M 39/10; A61M 39/1011; A61M 2039/1016; A61M 2039/1061;
(Continued)

(56) References Cited

U.S. PATENT DOCUMENTS

| 175,254 A | 3/1876 | Oberly |
|---|---|---|
| 827,626 A | 7/1906 | Gillet |

(Continued)

FOREIGN PATENT DOCUMENTS

| CN | 204601342 U | 9/2015 |
|---|---|---|
| EP | 1144041 A3 | 9/2002 |

(Continued)

OTHER PUBLICATIONS

Patent Corporation Treaty, International Search Report for PCT Application No. PCT/IB2019/053755, mailed Sep. 16, 2019.
(Continued)

*Primary Examiner* — Nathan R Price
*Assistant Examiner* — Haden Matthew Ritchie
(74) *Attorney, Agent, or Firm* — Nelson Mullins Riley & Scarborough LLP

(57) ABSTRACT

Apparatus and systems are disclosed that incorporate coupling mechanisms to enable coupling of two mating member such as medical devices such as introducers, sheaths, dilators. More specifically, the disclosure relates to releasable coupling mechanisms, to allow for releasable coupling of two medical devices such as a dilator and a sheath so the devices can be maneuvered and/or manipulated together for example during a part of a medical procedure.

32 Claims, 28 Drawing Sheets

(52) U.S. Cl.
CPC ............... *A61M 2025/0681* (2013.01); *A61M 2025/0687* (2013.01); *A61M 2039/0229* (2013.01); *A61M 2039/1016* (2013.01); *A61M 2039/1061* (2013.01)

(58) Field of Classification Search
CPC .. A61M 2039/1027; A61M 2039/1044; A61B 2017/00477; A61B 2017/347
See application file for complete search history.

(56) References Cited

U.S. PATENT DOCUMENTS

| | | |
|---|---|---|
| 848,711 A | 4/1907 | Daniel |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Matthew |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 3,990,727 A | 11/1976 | Gallagher |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,844,512 A | 7/1989 | Gahwiler |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,090,747 A | 2/1992 | Kotake |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,213,376 A | 5/1993 | Szabo |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,324,080 A | 6/1994 | McNaughton et al. |
| 5,327,905 A | 7/1994 | Avitall |
| 5,356,183 A | 10/1994 | Cole |
| 5,364,393 A | 11/1994 | Auth et al. |
| 5,372,596 A | 12/1994 | Klicek et al. |
| 5,374,088 A | 12/1994 | Moretti et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,466,017 A | 11/1995 | Szabo et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,520,420 A | 5/1996 | Moretti |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,573,279 A | 11/1996 | Rea et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,062 B1 | 5/2001 | Howell et al. |
| 6,228,076 B1 | 5/2001 | Winston et al. |
| 6,245,054 B1 | 6/2001 | Fuimaono et al. |
| 6,267,758 B1 | 7/2001 | Daw et al. |

(56) References Cited

U.S. PATENT DOCUMENTS

| | | |
|---|---|---|
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,217,256 B2 | 5/2007 | Di Palma |
| 7,240,926 B2 | 7/2007 | Dalle et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,401 B2 | 6/2012 | Morris et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 9,636,278 B2 | 5/2017 | Sanders et al. |
| 9,700,701 B2 | 7/2017 | Benjamin et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0149200 A1 | 10/2002 | Fumioka |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | Mcguckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Molante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0058579 A1 | 3/2006 | Oberlaender et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264911 A1 | 11/2006 | Nelson |
| 2006/0264927 A1 | 11/2006 | Ryan |
| 2006/0267341 A1 | 11/2006 | Takayanagi |
| 2006/0276710 A1 | 12/2006 | Krishnan |
| 2007/0021648 A1 | 1/2007 | Lenker et al. |
| 2007/0060879 A1 | 3/2007 | Weitzner et al. |
| 2007/0066975 A1 | 3/2007 | Wong et al. |
| 2007/0118099 A1 | 5/2007 | Trout |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |

(56) References Cited

U.S. PATENT DOCUMENTS

| | | |
|---|---|---|
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2008/0294111 A1 | 11/2008 | Tal et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2011/0251597 A1 | 10/2011 | Bharadwaj et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2013/0320672 A1 | 12/2013 | Steele |
| 2014/0206987 A1 | 7/2014 | Urbanski et al. |
| 2014/0296769 A1 | 10/2014 | Hyde et al. |
| 2016/0033068 A1 | 2/2016 | Wilhelm |
| 2016/0220741 A1 | 8/2016 | Garrison et al. |
| 2016/0271364 A1 | 9/2016 | Rowe et al. |
| 2017/0009920 A1 | 1/2017 | Canatella |
| 2019/0021763 A1 | 1/2019 | Zhou et al. |
| 2019/0247035 A1 | 8/2019 | Gittard et al. |

FOREIGN PATENT DOCUMENTS

| | | | |
|---|---|---|---|
| JP | 2010-137043 A | 6/2010 | |
| JP | 2010-207610 A | 9/2010 | |
| WO | 01/32524 A1 | 5/2001 | |
| WO | 2006/130378 A1 | 12/2006 | |
| WO | 2011049824 A1 | 4/2011 | |
| WO | WO-2016018998 A1 * | 2/2016 | ............ A61B 5/24 |
| WO | 2016/152016 A1 | 9/2016 | |

OTHER PUBLICATIONS

Patent Corporation Treaty, Written Opinion for PCT Application No. PCT/IB2019/053755, mailed Sep. 16, 2019.

* cited by examiner

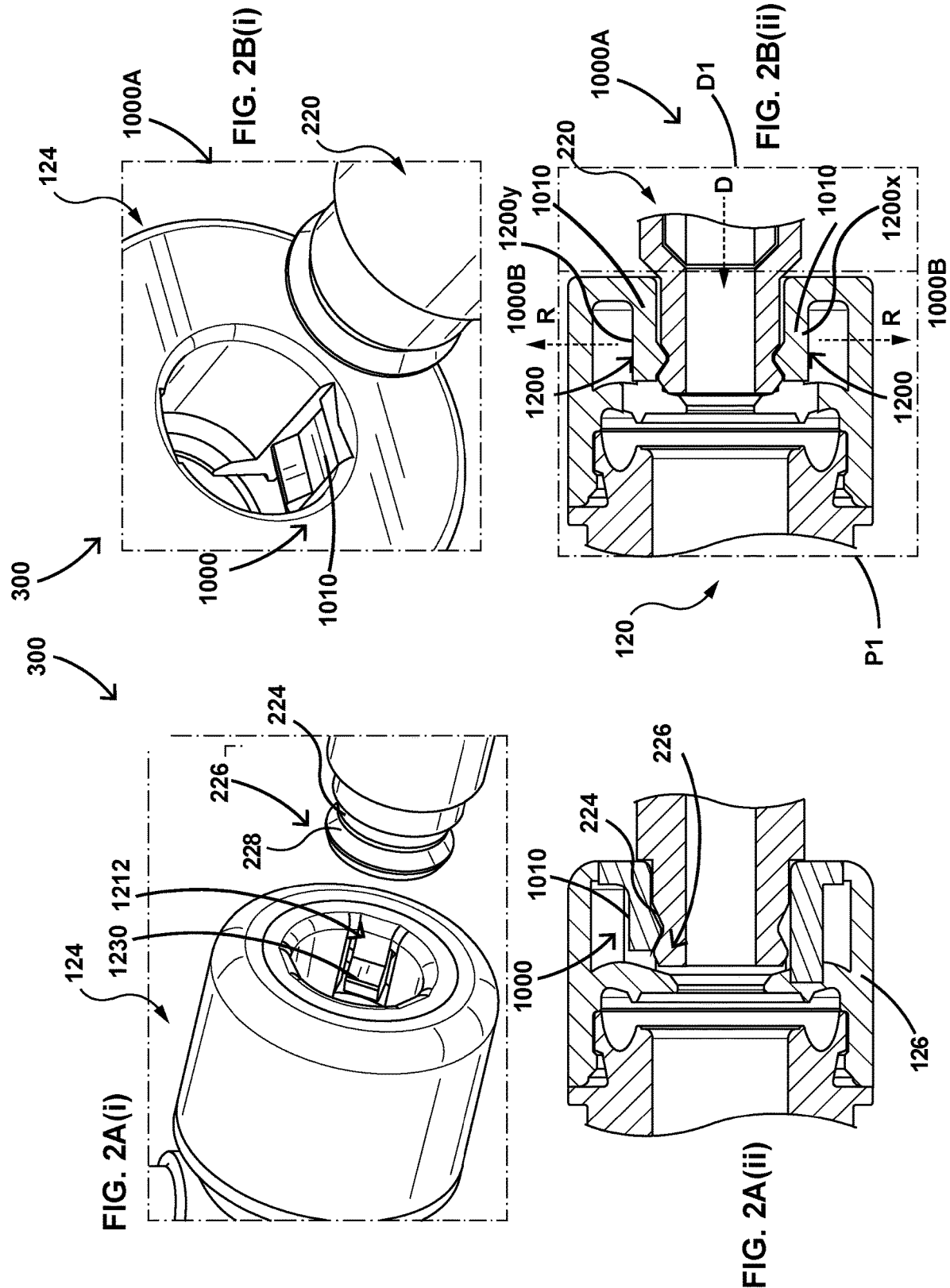

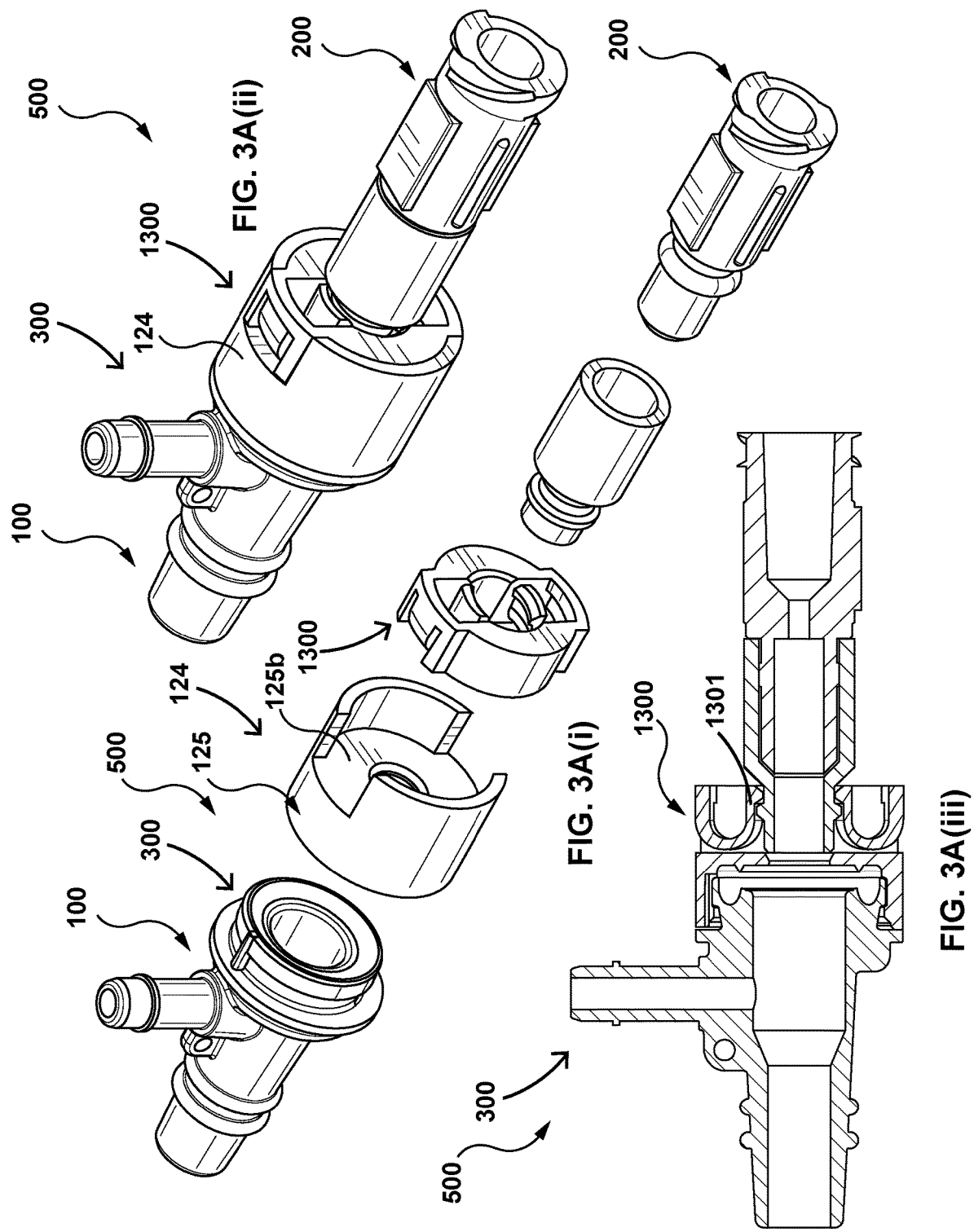

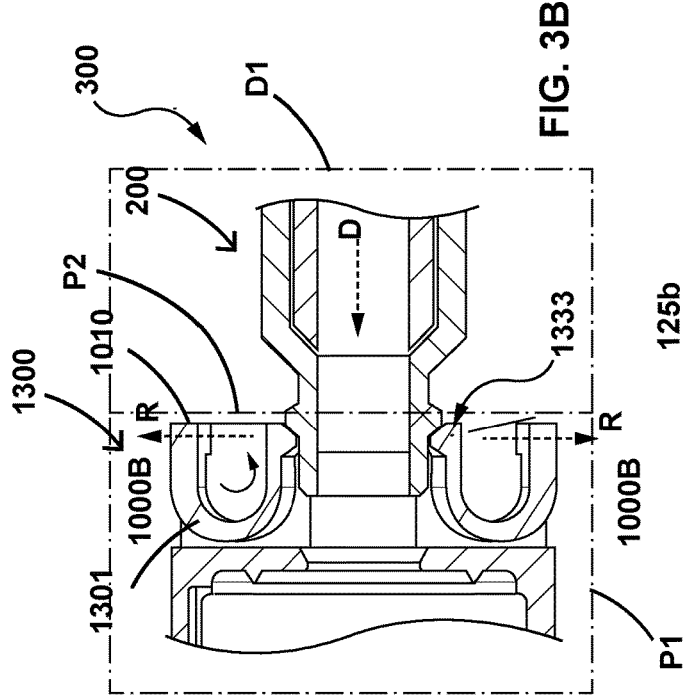
FIG. 3B
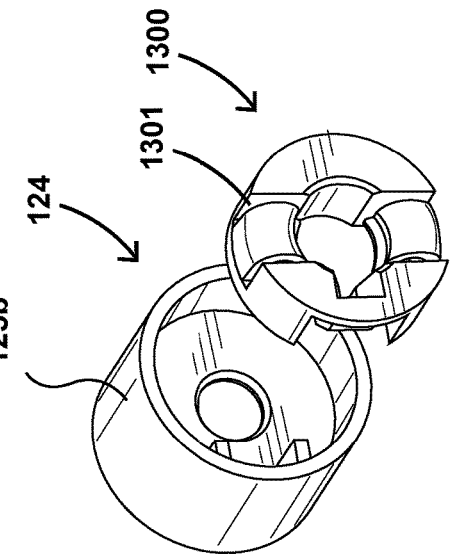
FIG. 3D(ii)
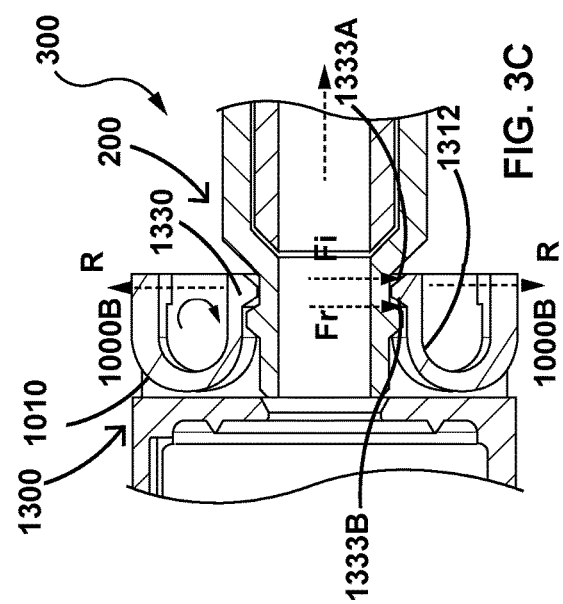
FIG. 3C
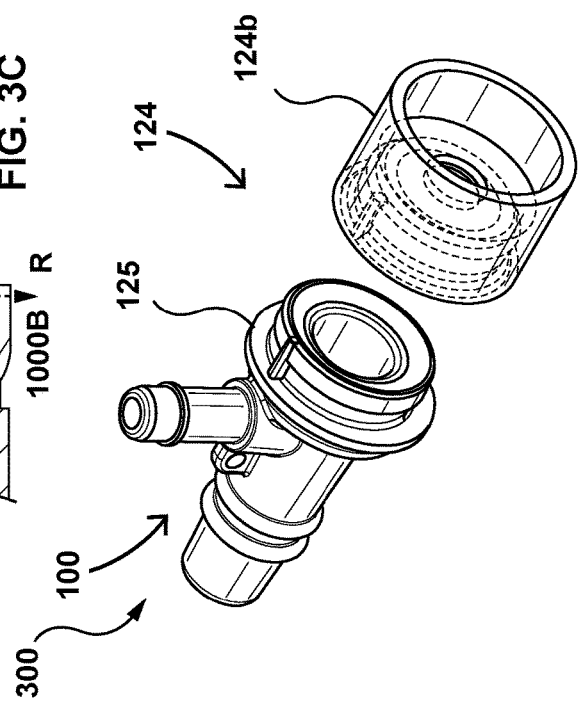
FIG. 3D(i)

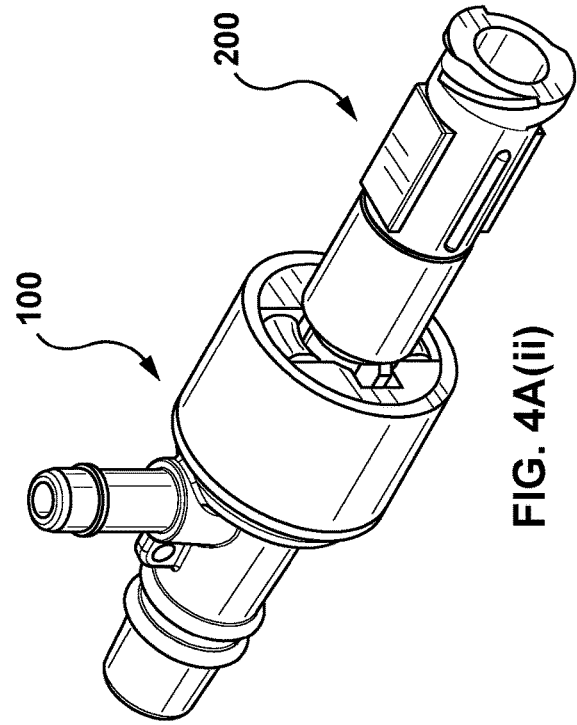
FIG. 4A(i)
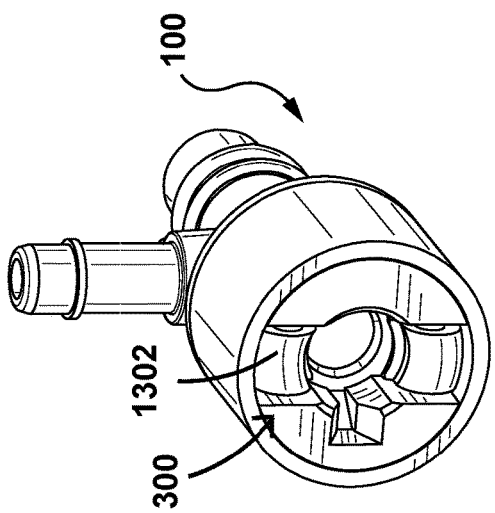
FIG. 4A(ii)
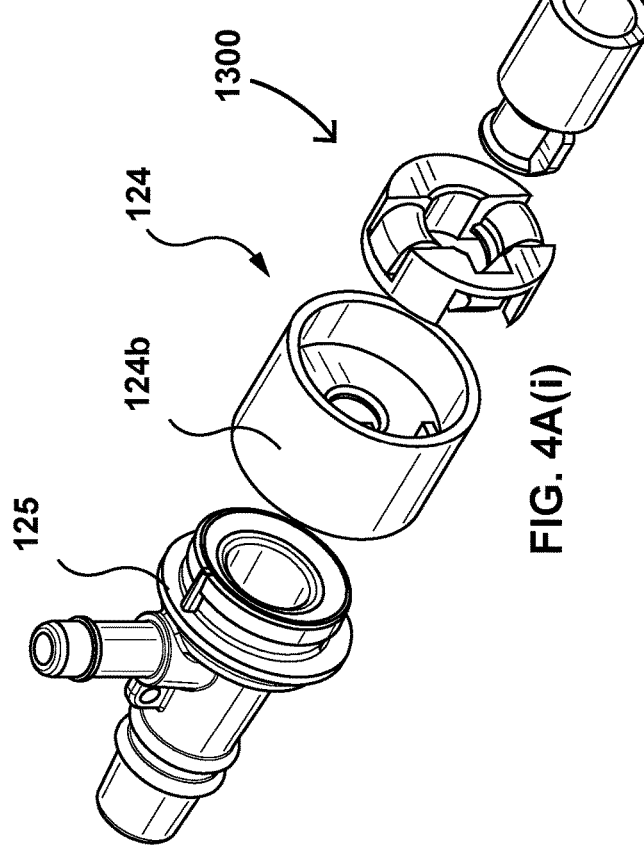
FIG. 4A(iii)
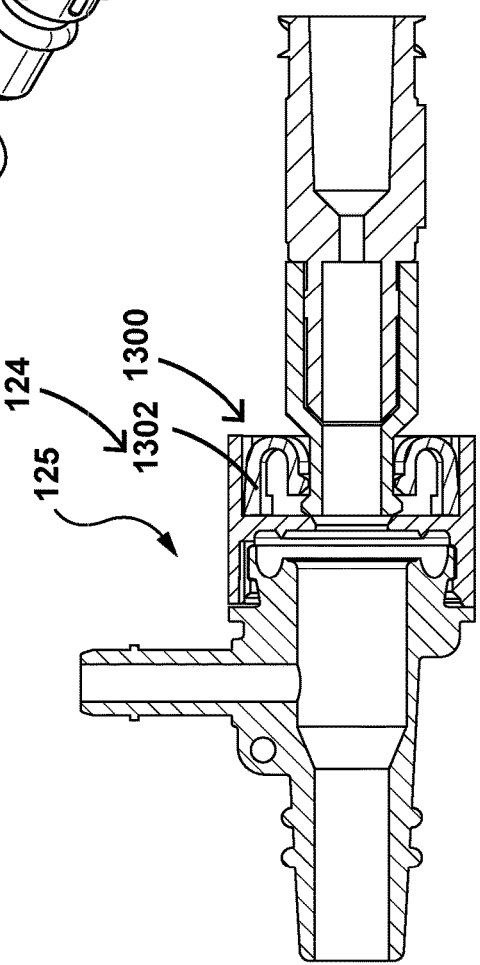
FIG. 4A(iv)

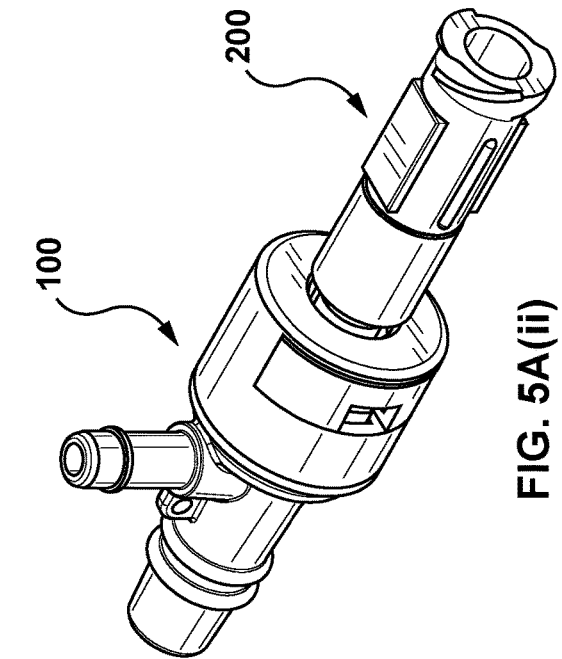
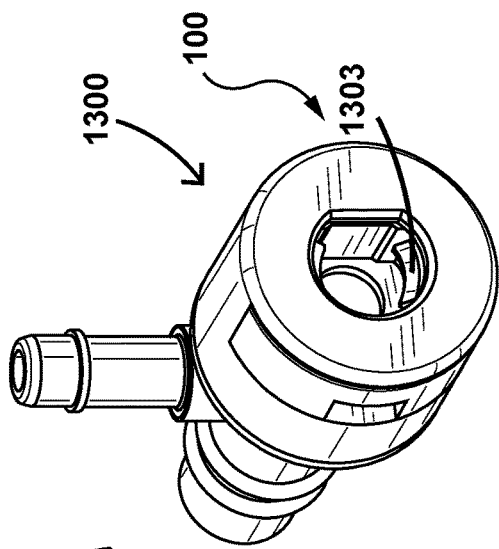
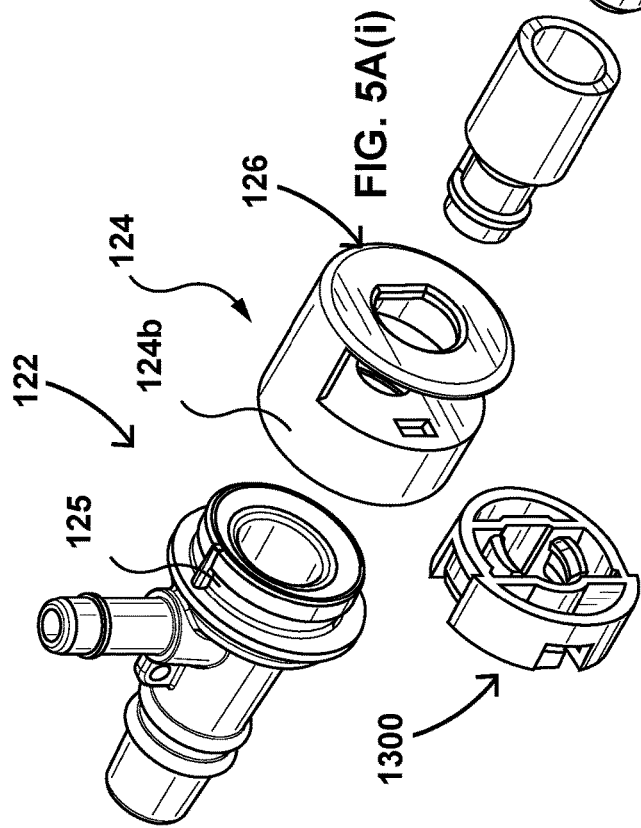
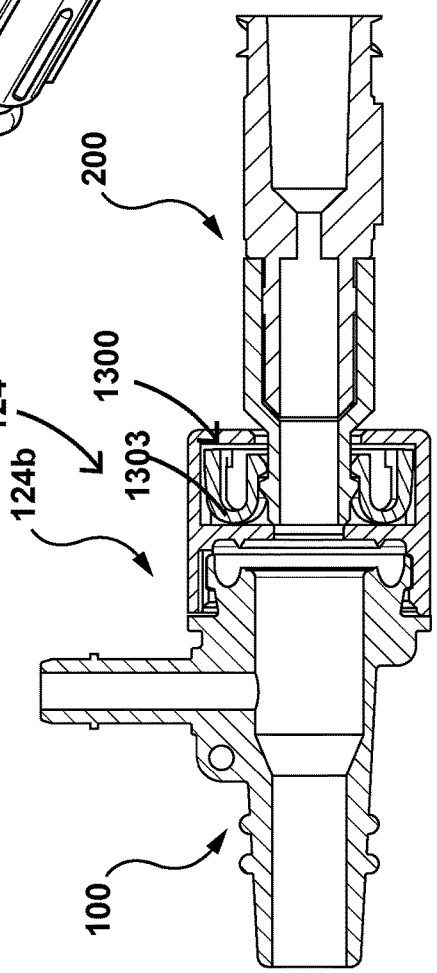
FIG. 5A(i)
FIG. 5A(ii)
FIG. 5A(iii)
FIG. 5A(iv)

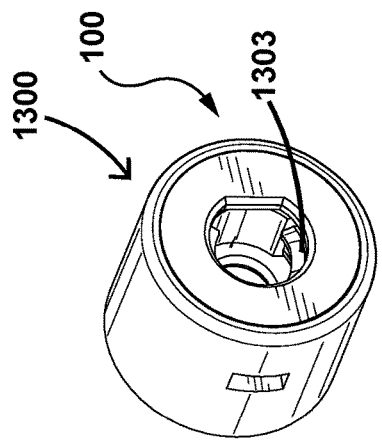
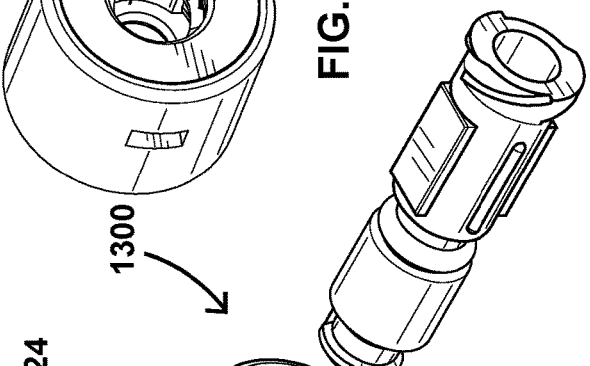
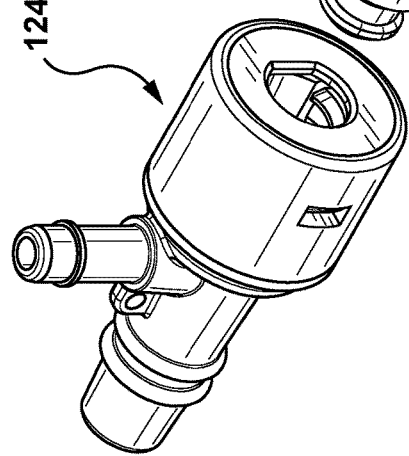
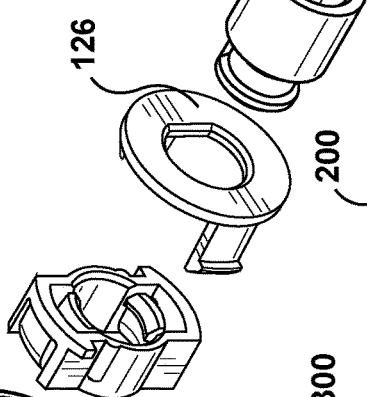
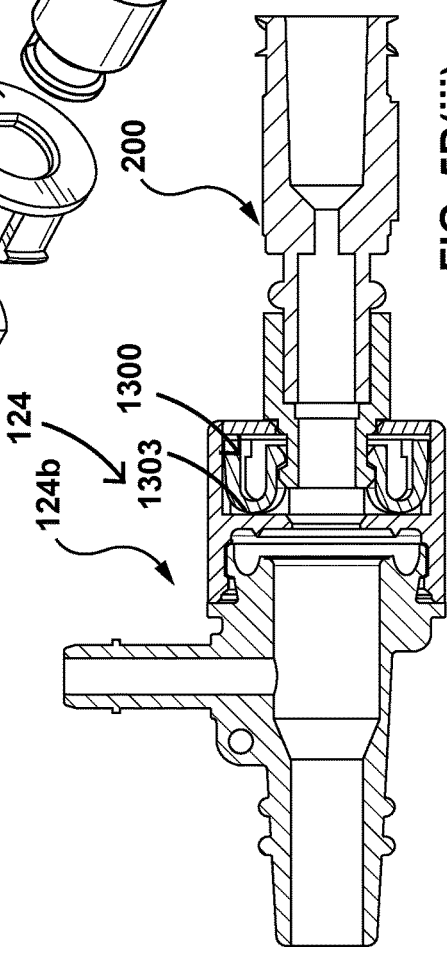

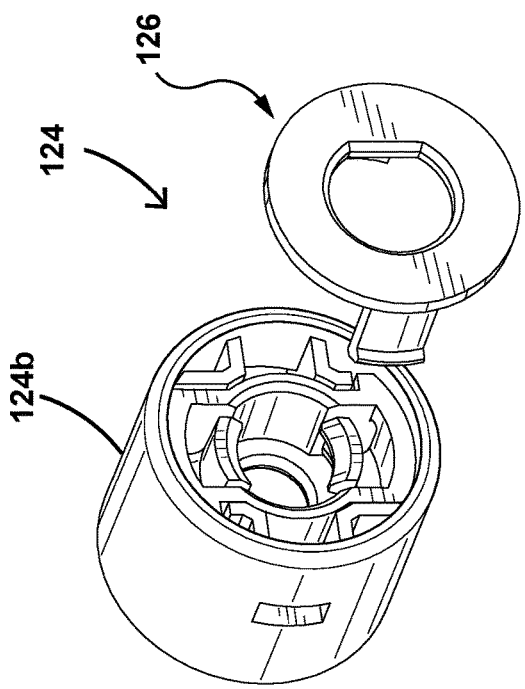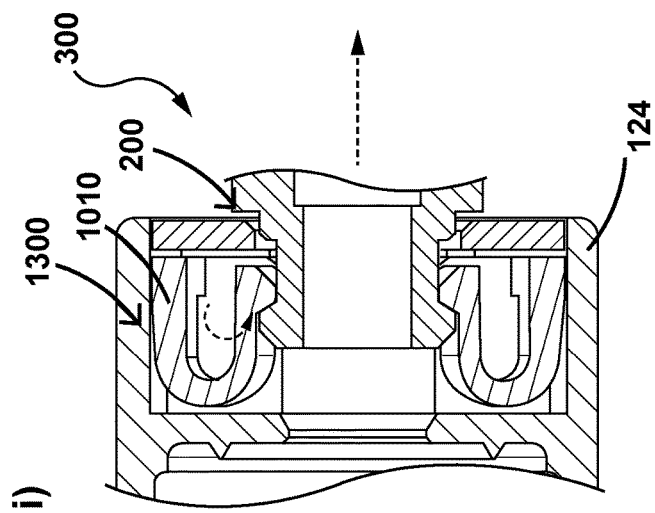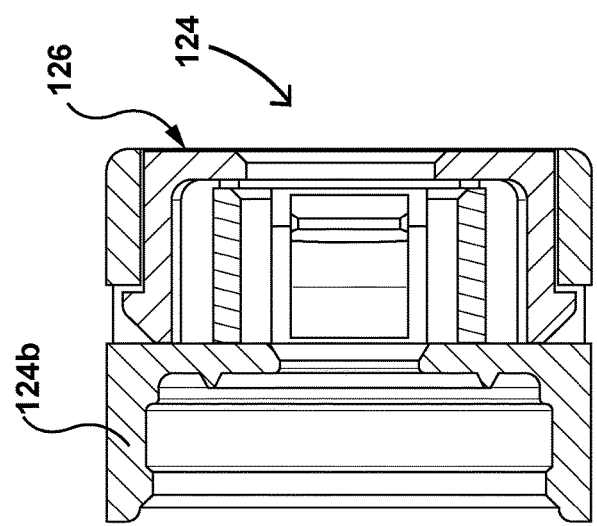
FIG. 5E(i)
FIG. 5E(ii)
FIG. 5F(i)
FIG. 5F(ii)

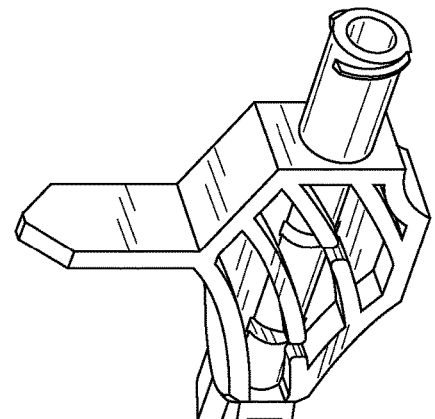
FIG. 6A(i)
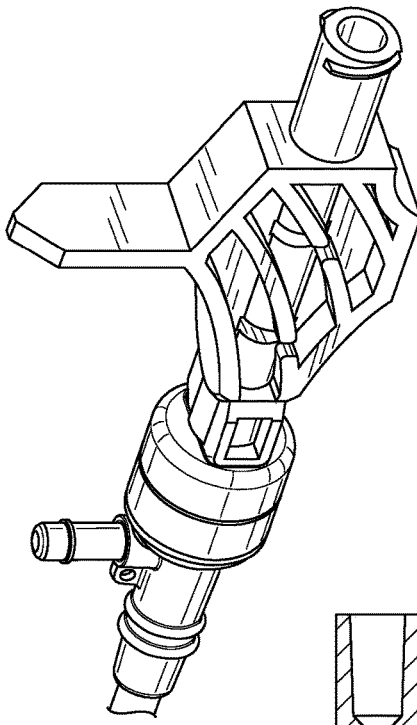
FIG. 6A(iv)
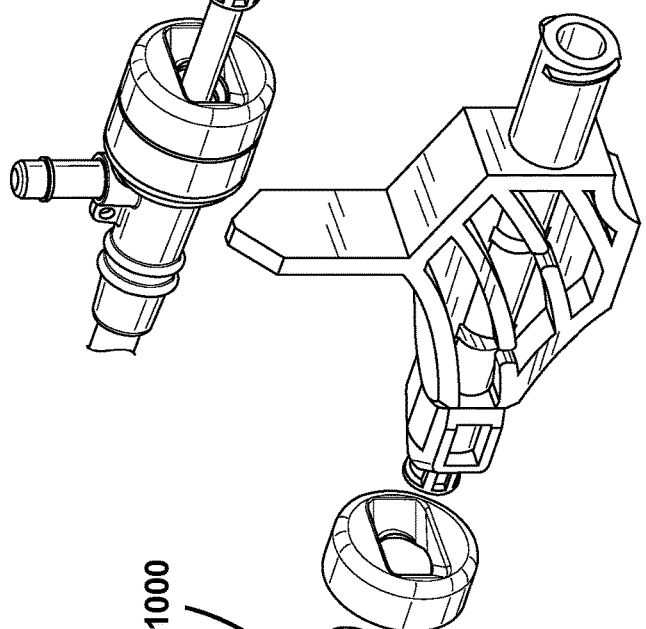
FIG. 6A(ii)
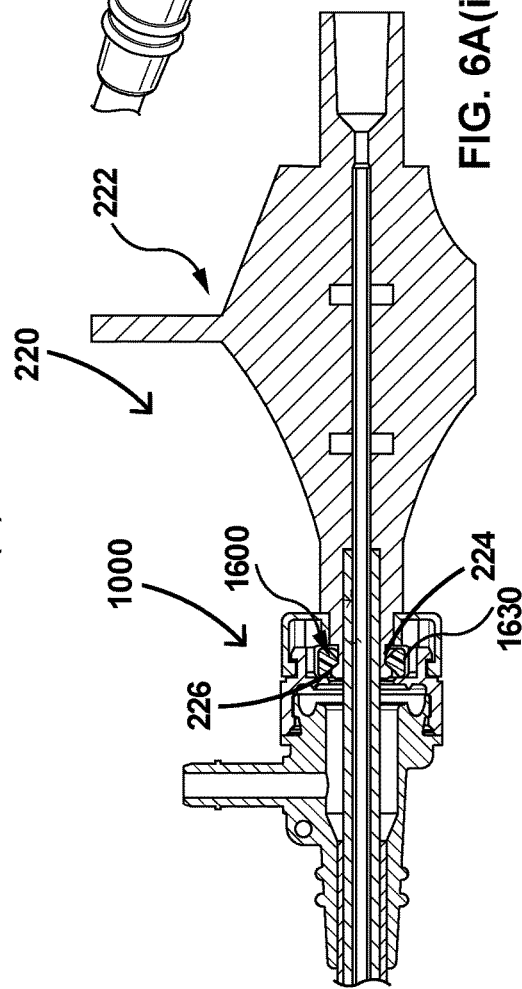
FIG. 6A(iii)

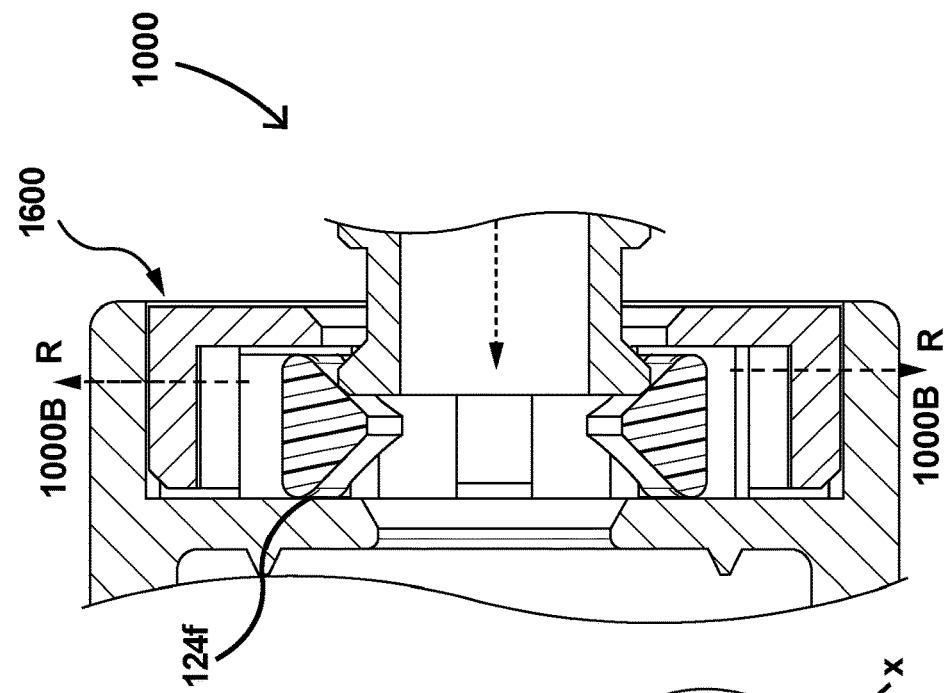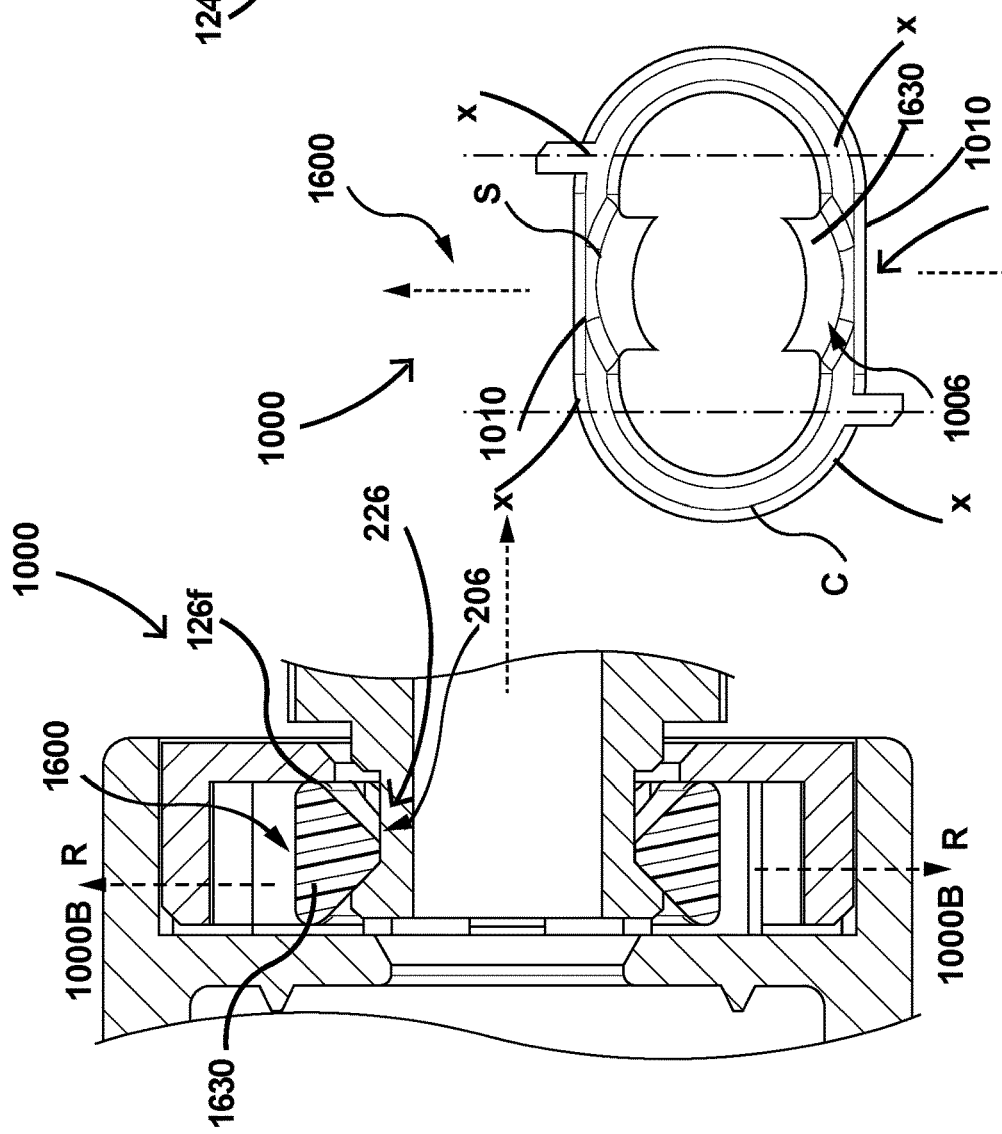

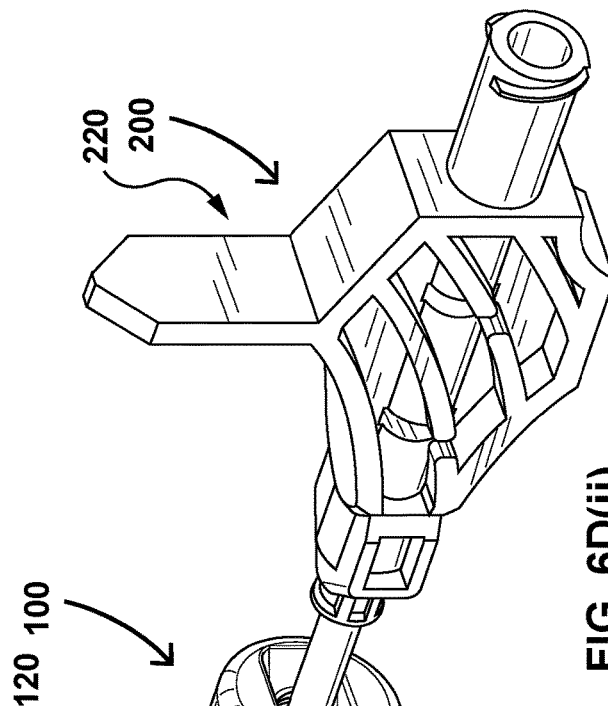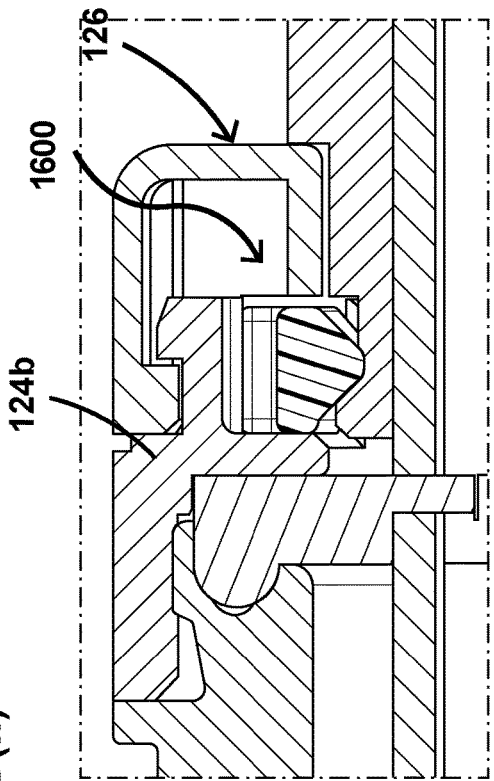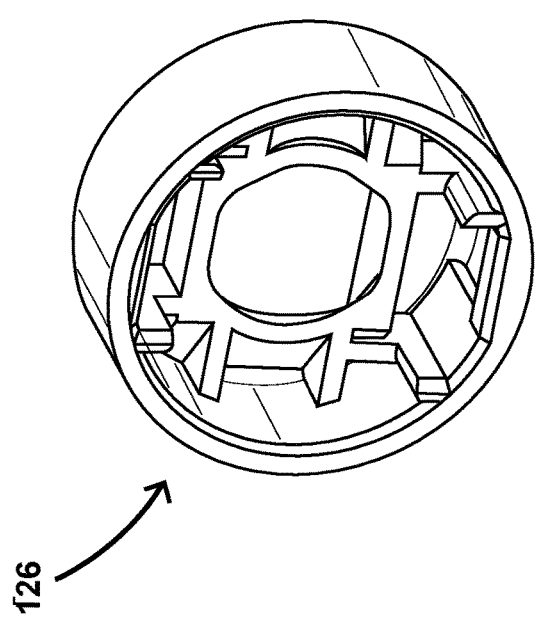
FIG. 6D(ii)
FIG. 6E(ii)
FIG. 6E(i)

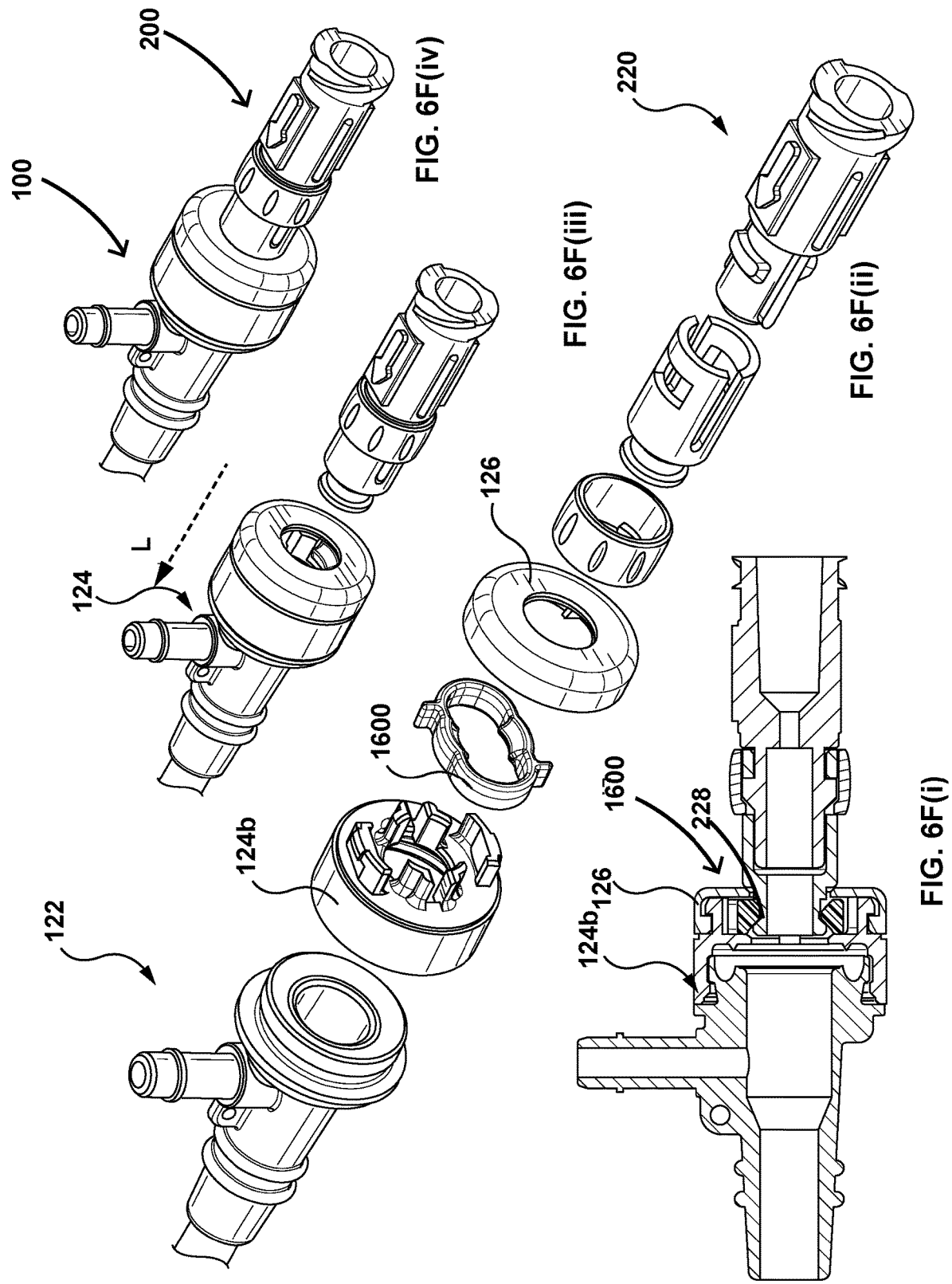

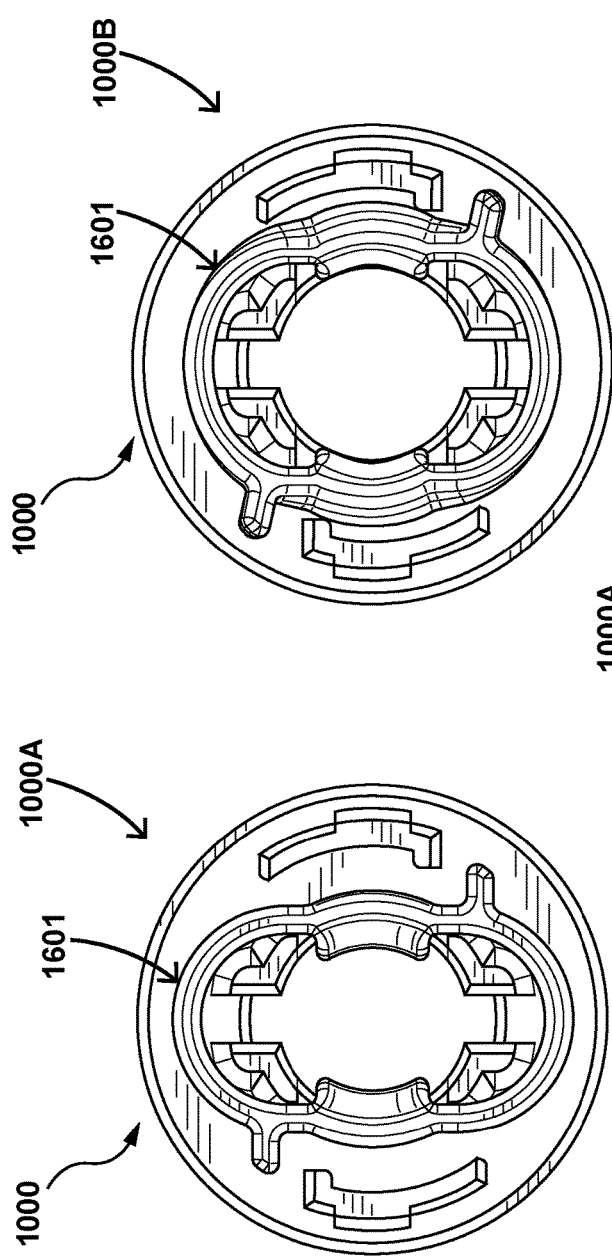
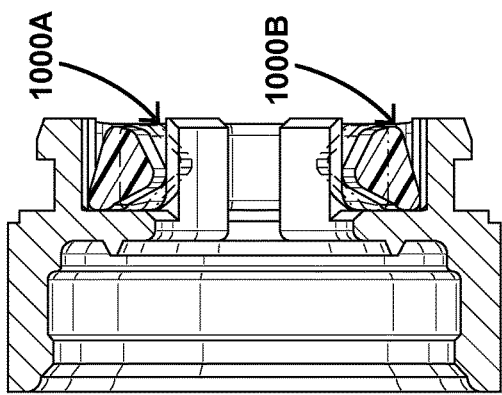
FIG. 7A
FIG. 7B
FIG. 7C
FIG. 7D

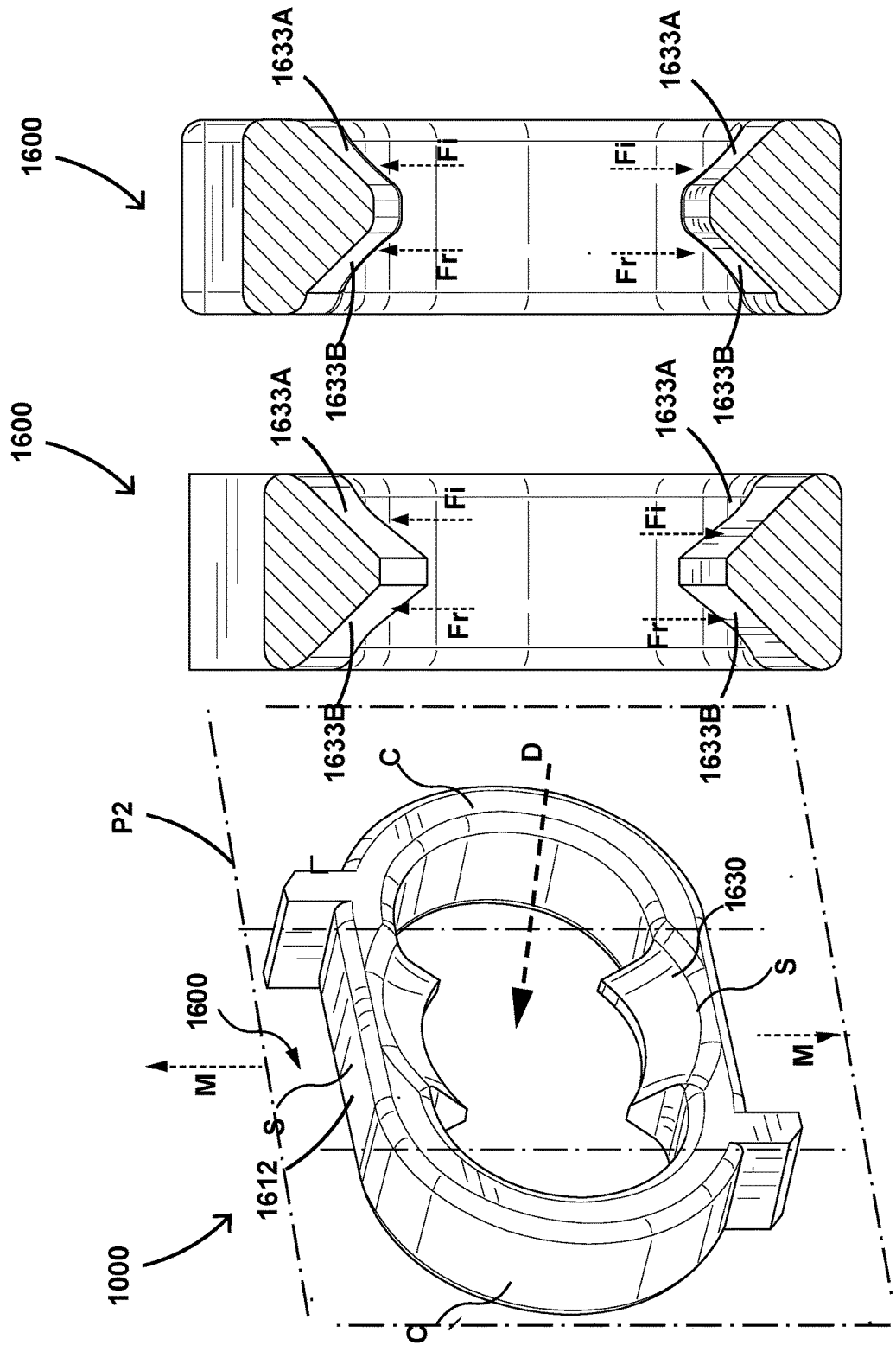

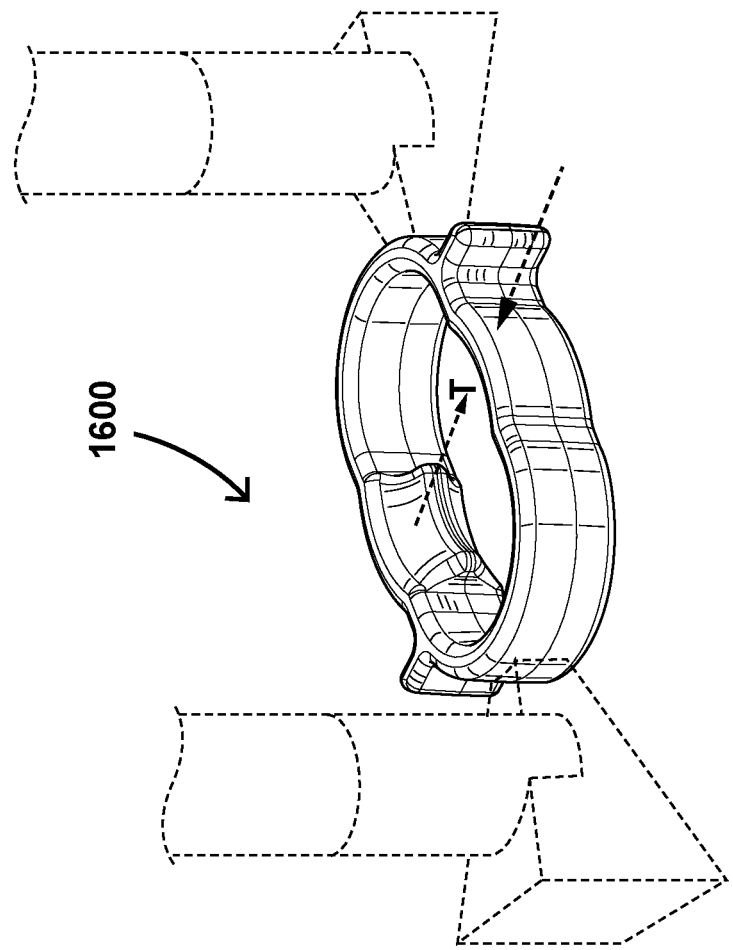
FIG. 8D(ii)
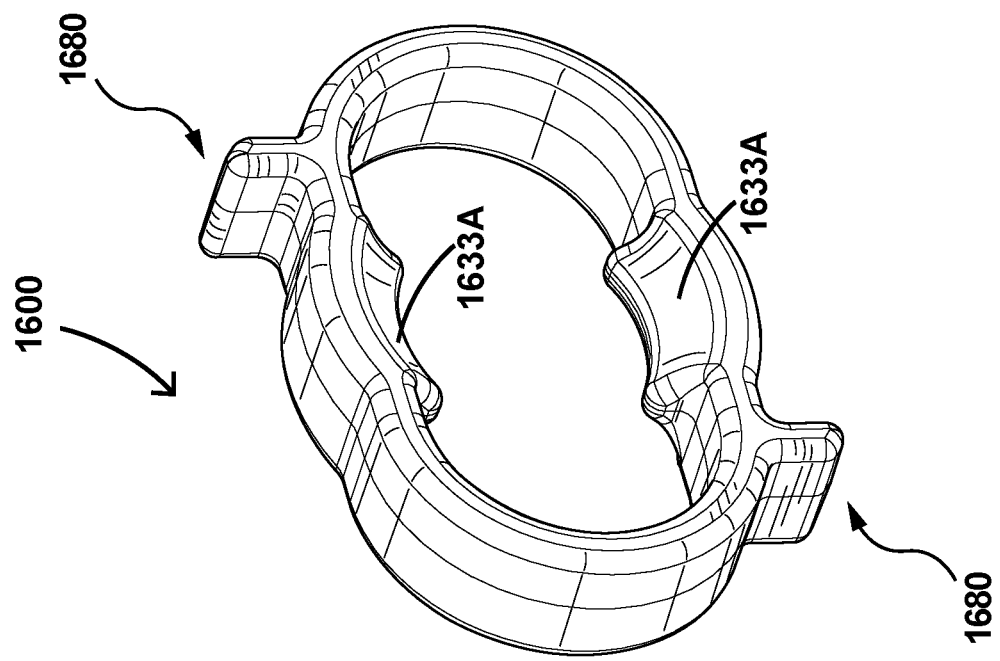
FIG. 8D(i)

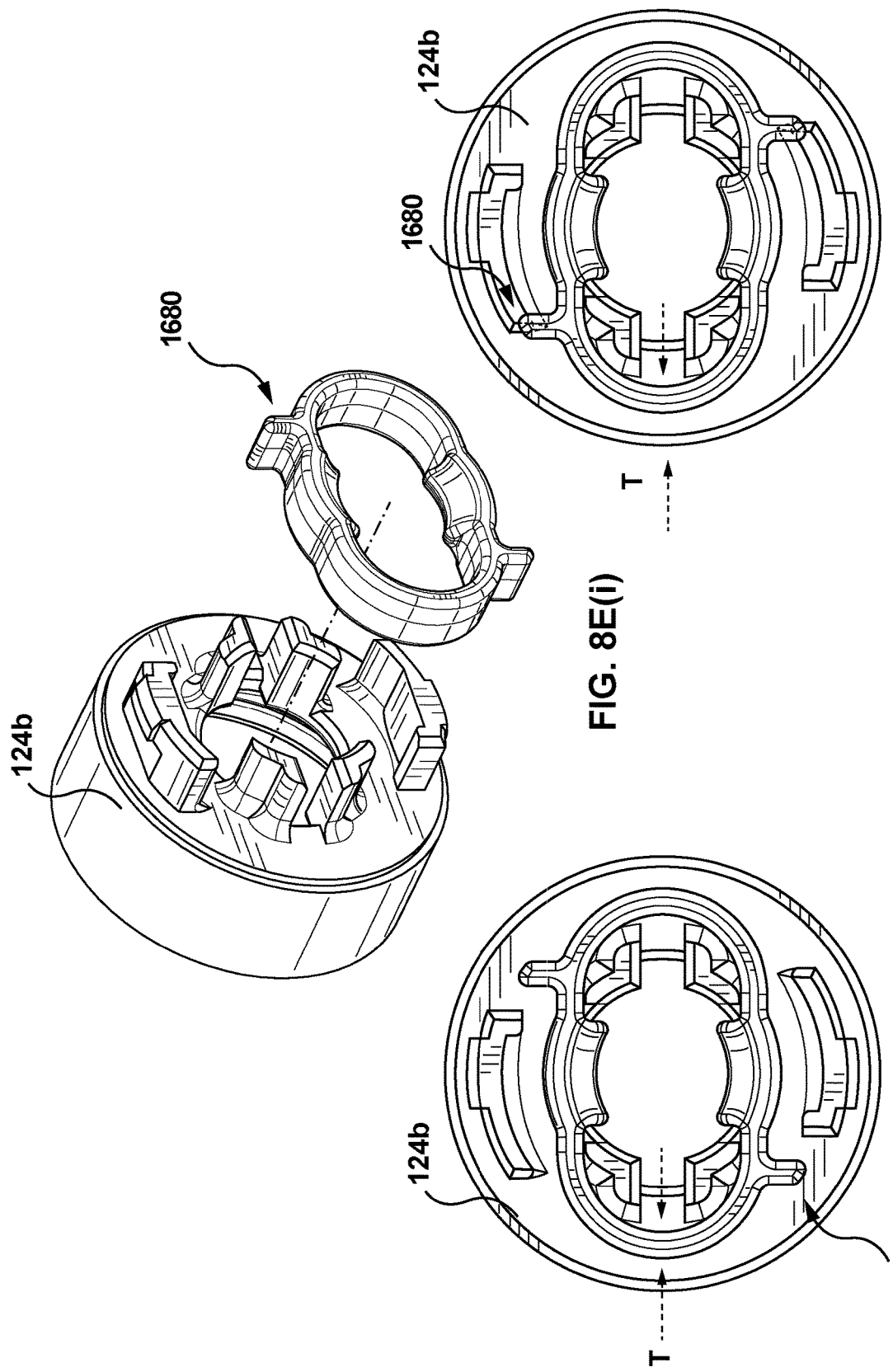

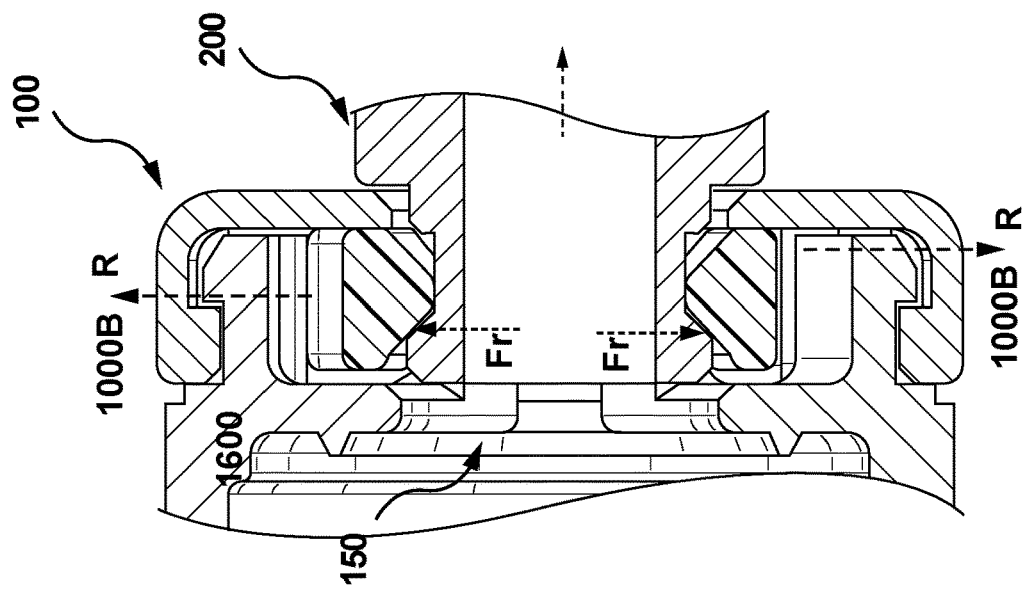
FIG. 8F(iii)
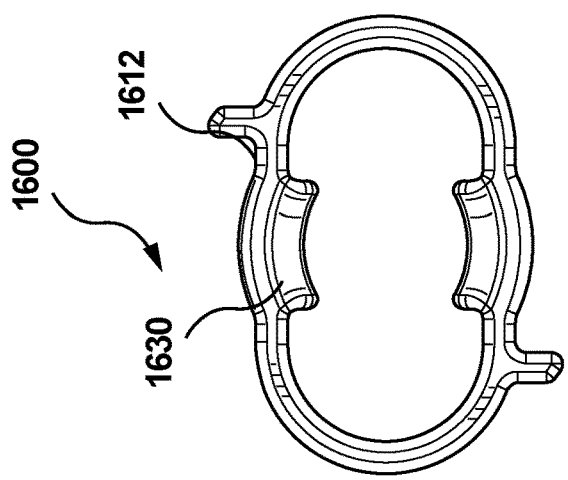
FIG. 8F(ii)
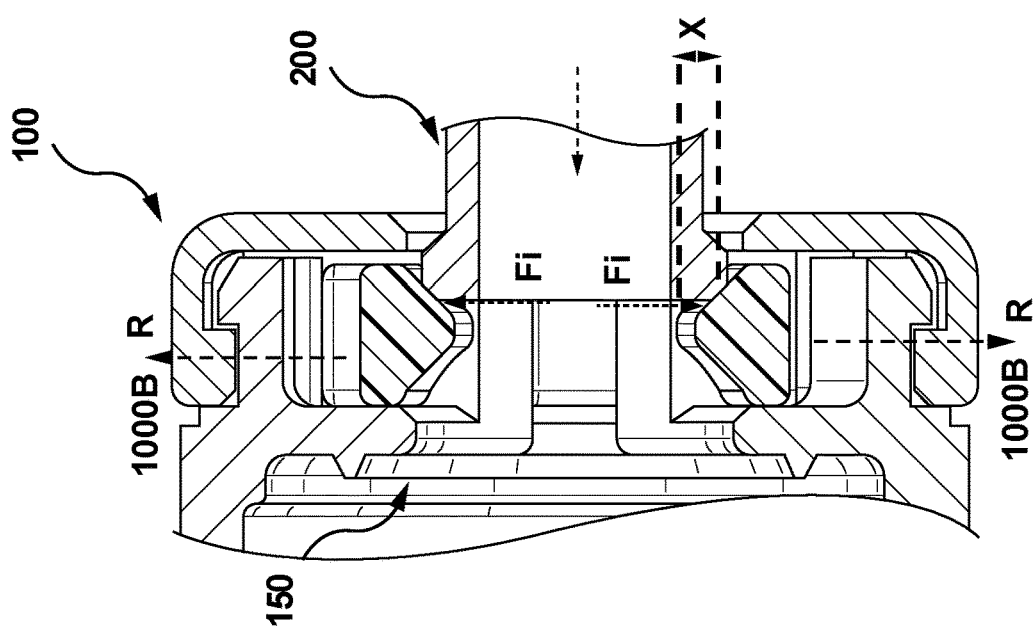
FIG. 8F(i)

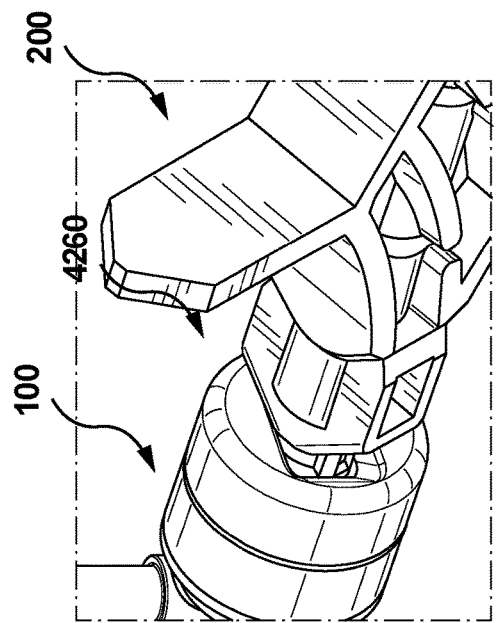
FIG. 9A(ii)
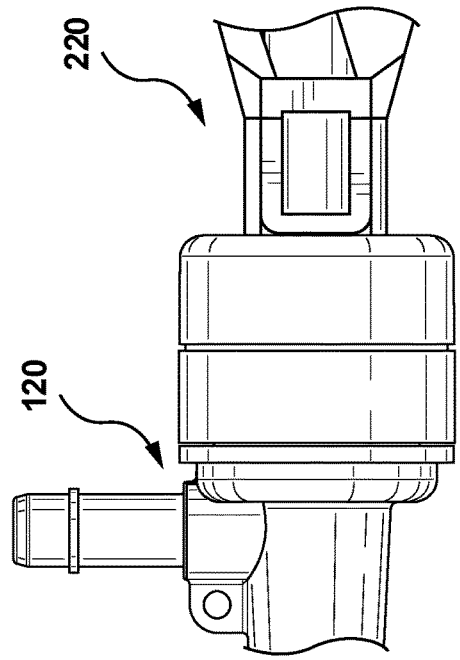
FIG. 9A(iv)
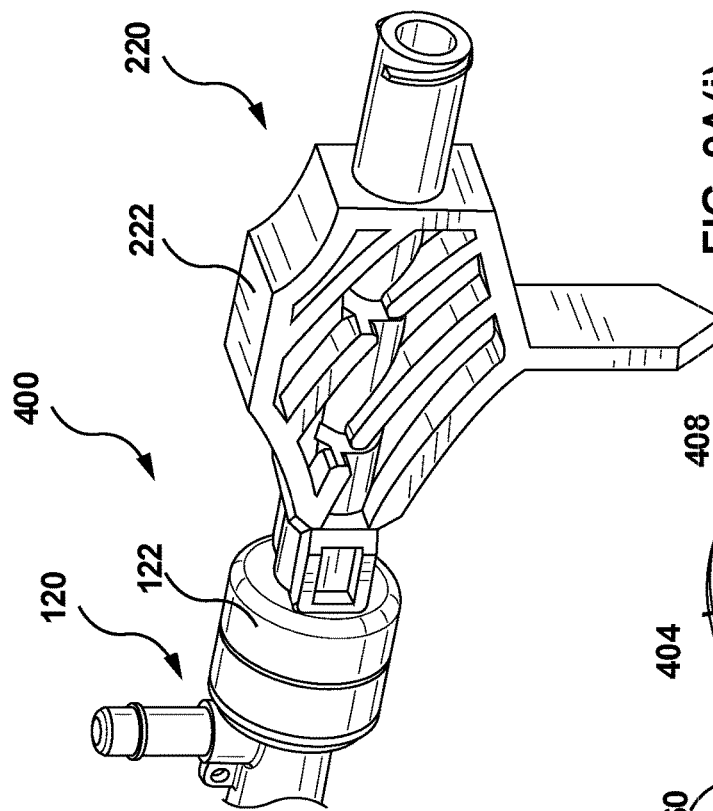
FIG. 9A(i)
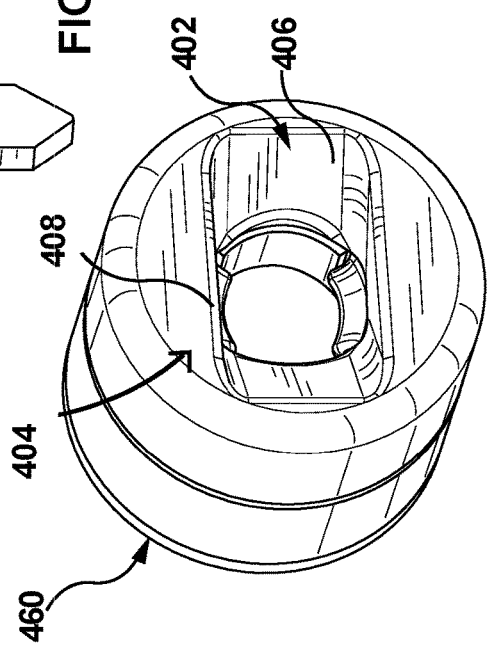
FIG. 9A(iii)

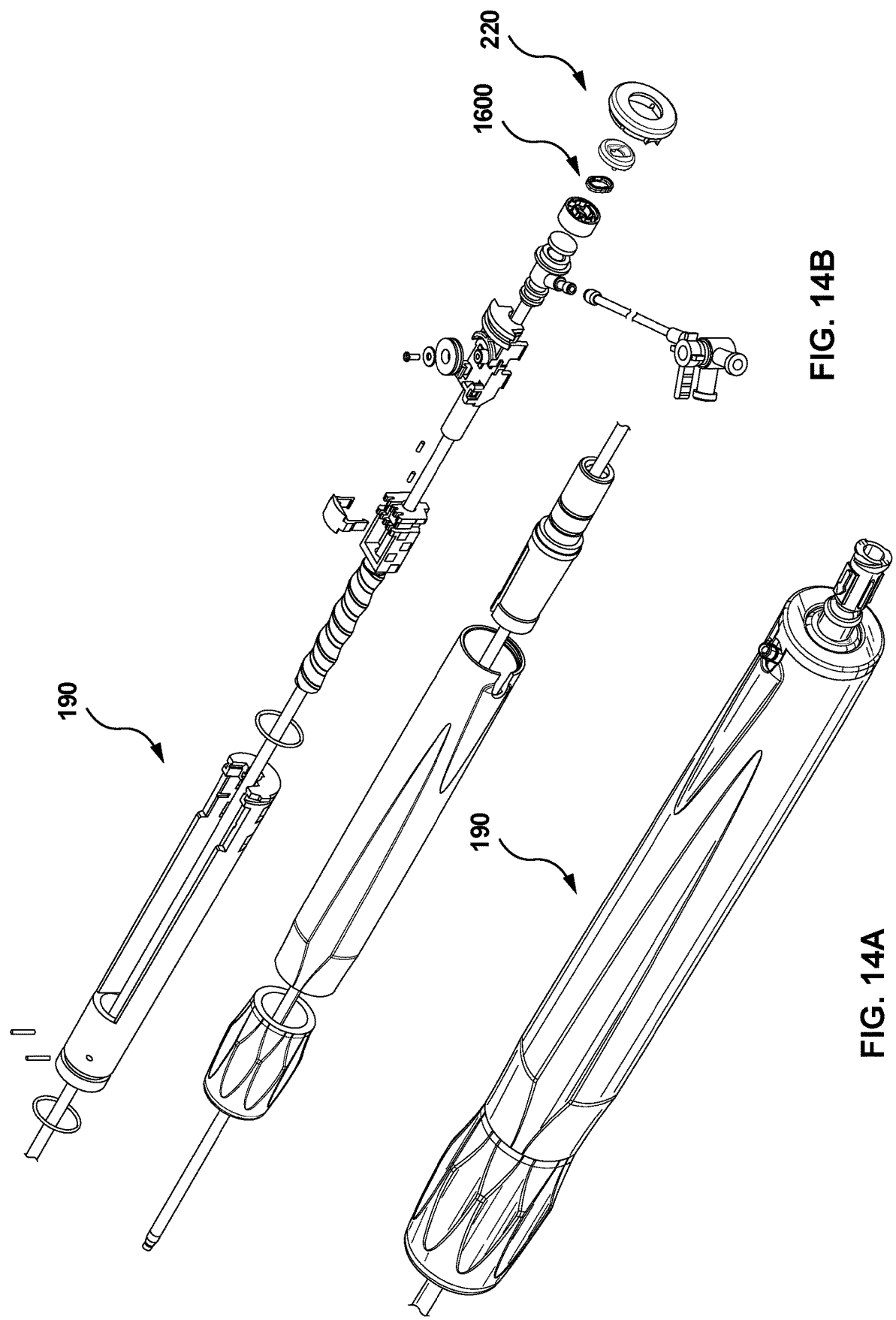

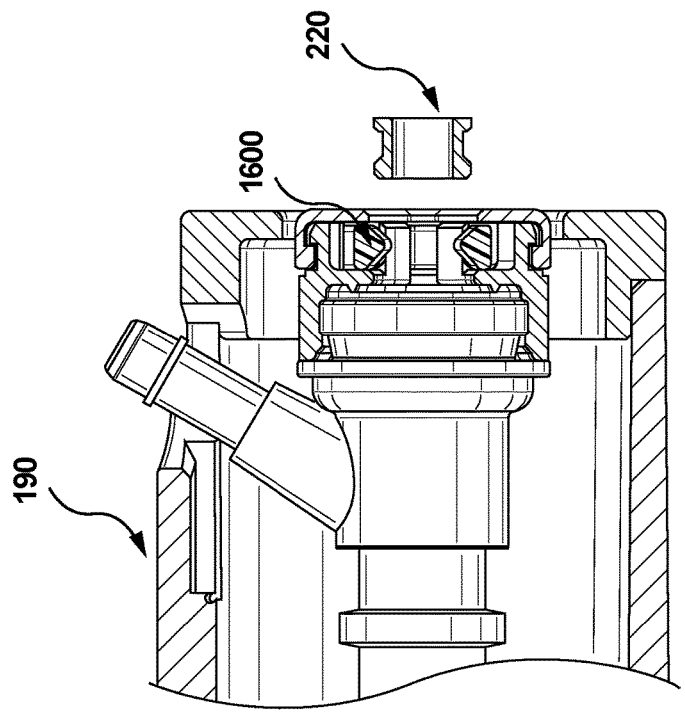
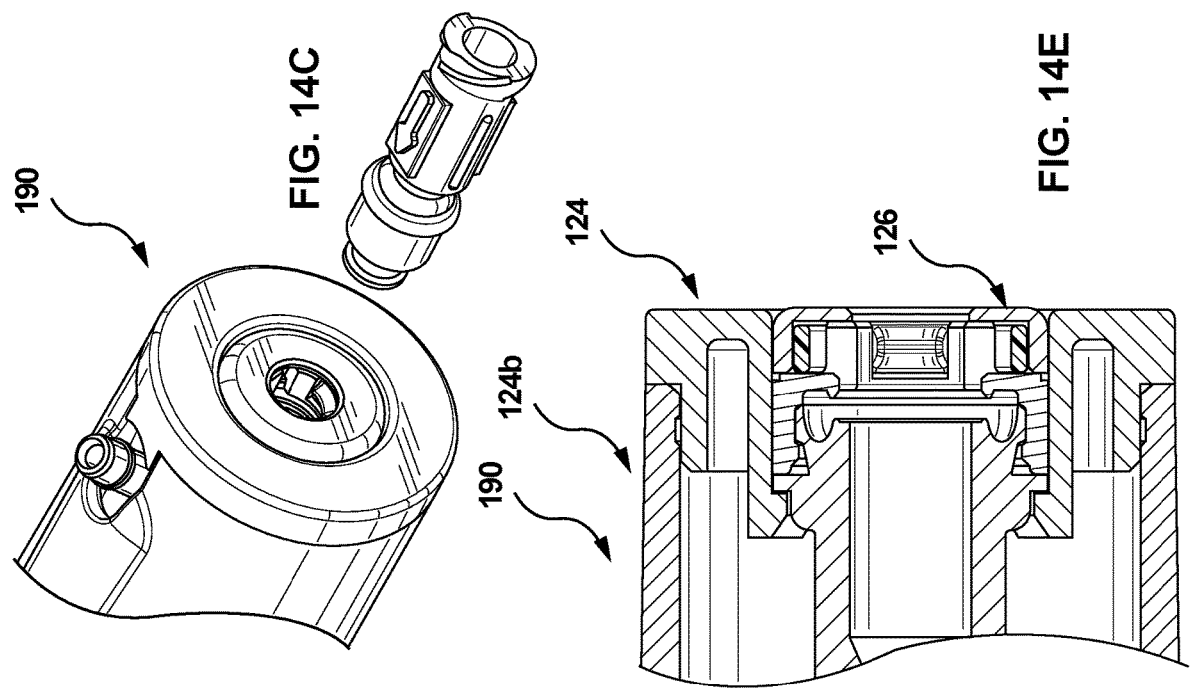

COUPLING MECHANISMS FOR MEDICAL DEVICES

The disclosure relates to systems and methods that incorporate coupling mechanisms that allow for coupling two mating member such as two medical devices such as introducers, sheaths, dilators and the like for a part of the procedure. More specifically, the disclosure relates to releasable coupling mechanisms, specifically snap-fit mechanisms, to allow for releasably coupling two medical devices such as a dilator and sheaths for a part of the procedure.

BRIEF DESCRIPTION OF THE DRAWINGS

In order that the invention may be readily understood, embodiments of the invention are illustrated by way of examples in the accompanying drawings, in which:

FIG. 2A(i) is a perspective view of a hub with a coupling mechanism, showing another device about to be inserted into the hub;

FIG. 2A(ii) is a cross sectional view of the hub of FIG. 2A(i), showing the other device partially inserted through the coupling mechanism;

FIG. 2B(i) is a perspective view of a hub with a coupling mechanism, showing another device about to be inserted into the hub;

FIG. 2B(ii) is a cross sectional view of the hub of FIG. 2B(i), showing the other device partially inserted through the coupling mechanism;

FIGS. 3A(i), 3A(ii) and 3A(iii) are, respectively, an exploded view, a perspective view and a cross section through a hub containing an embodiment of a coupling mechanism of the present invention;

FIGS. 3B and 3C are, respectively, cross sectional views of a device being inserted through an embodiment of a coupling mechanism and the device being retracted therefrom;

FIGS. 3D(i) and 3D(ii) are perspective exploded views illustrating various features of a hub and coupling mechanism of the present invention;

FIGS. 4A(i), 4A(ii) and 4A(iii) are, respectively, an exploded view, a perspective view and a cross section through a hub containing an embodiment of a coupling mechanism of the present invention;

FIG. 4A(iv) is a perspective view of an embodiment of a hub and coupling mechanism of the present invention;

FIGS. 5A(i), 5A(ii) and 5A(iii) are, respectively, a perspective view, an exploded view, and a cross section through a hub containing an embodiment of a coupling mechanism of the present invention, as well as a device inserted through the coupling mechanism;

FIG. 5A(iv) is a perspective view of an embodiment of a hub and coupling mechanism of the present invention;

FIGS. 5D(i), 5D(ii) and 5D(iii) are, respectively, an exploded view, a perspective view and a cross section through a hub containing an embodiment of a coupling mechanism of the present invention;

FIG. 5D(iv) is a perspective view of an embodiment of a hub and coupling mechanism of the present invention;

FIGS. 5E(i) and 5E(ii) show, respectively, cross-sectional and perspective views of an embodiment of a housing and a coupling mechanism of the present invention;

FIGS. 5F(i) and 5F(ii) are cross-sectional illustrations of a device being inserted through an embodiment of a coupling mechanism of the present invention and being removed therefrom;

FIGS. 5A(i), 5A(ii) and 5A(iii) are, respectively, a perspective view, an exploded view, and a cross section through a hub containing an embodiment of a coupling mechanism of the present invention, as well as a device inserted through the coupling mechanism;

FIG. 5A(iv) is a perspective view of an embodiment of a hub and coupling mechanism of the present invention;

FIGS. 6A(i) and 6A(ivi) are, respectively, perspective views of a device partially and fully inserted into a hub comprising an embodiment of a coupling mechanism of the present invention;

FIGS. 6A(ii) and 6A(iii) are, respectively, an exploded view and a cross section through a hub containing an embodiment of a coupling mechanism of the present invention, as well as a device inserted through the coupling mechanism;

FIGS. 6B and 6C are, respectively, cross sectional views of a device inserted through an alternate embodiment of a coupling mechanism of the present invention and being removed therefrom;

FIG. 6D(i) is a side view of an alternative embodiment of a coupling mechanism of the present invention;

FIG. 6D(ii) shows a perspective view of a device partially inserted through an embodiment of a coupling mechanism of the present invention;

FIG. 6E(i) shows a side view of an embodiment of a cap of a hub;

FIG. 6E(ii) is a partial cross-sectional view of an alternate embodiment of a coupling mechanism located within a hub;

FIGS. 6F(i) and 6F(ii) are, respectively, a cross section through, and an exploded view of, a hub containing an embodiment of a coupling mechanism of the present invention, as well as a device inserted through the coupling mechanism;

FIGS. 6F(iii) and 6F(iv) are, respectively, perspective views of a device being inserted into a hub and being removed therefrom comprising an embodiment of a coupling mechanism of the present invention;

FIGS. 7A, 7B and 7C illustrate top views of a coupling member in accordance with an embodiment of the present invention in its different states;

FIG. 7D illustrates a side cross-sectional view of a coupling member in accordance with an embodiment of the present invention in its different states;

FIG. 8A is a perspective view of a coupling member in accordance with an alternative embodiment of the present invention;

FIG. 8A is a perspective view of a coupling member in accordance with an alternative embodiment of the present invention;

FIGS. 8B and 8C are different cross-sectional views of the coupling member taken along the mid-point of the coupling member of FIG. 8A, in accordance with an alternative embodiments of the present invention.

FIGS. 8D(i) and 8D(ii) are a perspective view of a coupling member in accordance with an alternative embodiment of the present invention;

FIGS. 8E(i), and 8E(iii) are a top view of a coupling member in accordance with an embodiment of the present invention and a portion of the housing for retaining the same;

FIG. 8E(ii) is a perspective view of a coupling member in accordance with an alternative embodiment of the present invention as well as a portion of the housing for retaining the same;

FIGS. 8F(i), and 8F(iii) are FIGS. 6B and 6C are, respectively, cross sectional views of a device inserted through an alternate embodiment of a coupling mechanism of the present invention and being removed therefrom;

FIG. 8F(ii) is a perspective view of a coupling member in accordance with an alternative embodiment of the present invention as well as a portion of the housing for retaining the same;

FIGS. 9A(i), 9A(ii), 9A(iii) and 9A(iv) are perspective views of components of a rotational locking mechanism comprising a first mating member and a second mating member;

FIGS. 14A and 14B are, respectively, an exploded view and a perspective view of an alternate embodiment of the first mating member containing an embodiment of a coupling mechanism of the present invention, as well as a device inserted through the coupling mechanism;

FIG. 14C is a perspective view of an alternate embodiment of the first mating member comprising an embodiment of a coupling mechanism of the present invention, in accordance with an embodiment of the present invention; and FIGS. 14D and 14E are cross sectional views taken along different sections of the second mating member shown in FIGS. 14C, that comprises an embodiment of a coupling mechanism of the present invention, as well as a device inserted through the coupling mechanism, in accordance with an embodiment of the present invention.

DETAILED DESCRIPTION

Figure 1A:
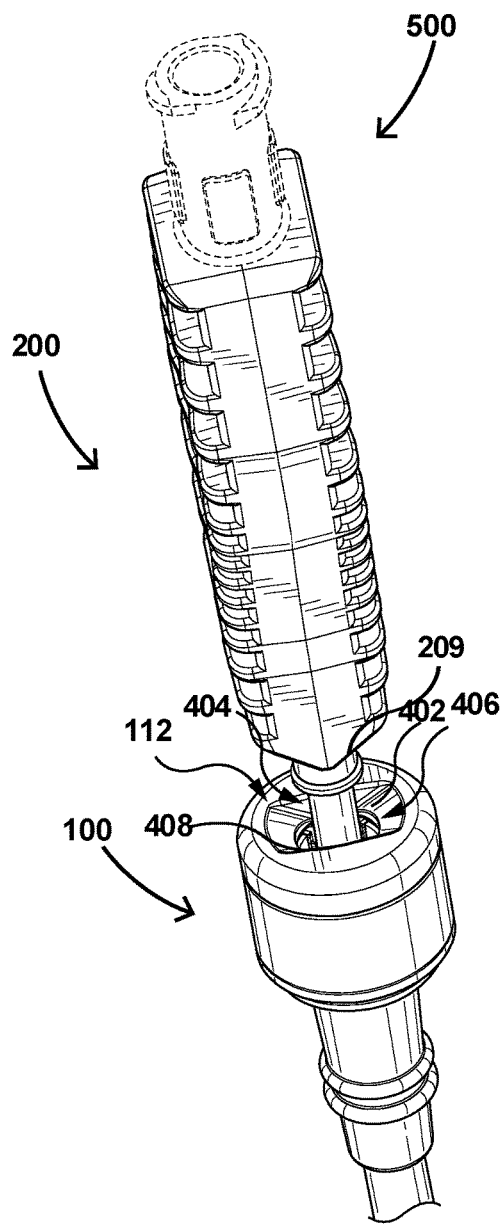
FIG. 1A is a perspective view of a hub for a medical device, comprising a coupling mechanism in accordance with an embodiment of the present invention and further showing a second device at least partially inserted into the hub.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In order to carry out certain medical procedures such as trans-septal procedures, it is necessary to gain access to the heart specifically to the left atrium of the heart. Access may be obtained to the heart from vasculature using one or more medical devices such as an introducer or sheath. In order to gain access, a superior approach may be used (by gaining access to the heart for example from the jugular vein through the superior vena cava), or alternatively access may be obtained from the femoral or inferior approach (by gaining access to the heart from the femoral vein through the inferior vena cava). Once access is obtained into the left atrium, one or more additional devices may be advanced through the introducer or sheath to carry out a part of the procedure. For example, in order to carry out trans-septal puncture, a puncture device is advanced through vasculature (for example through the sheath and/or through a dilator positioned within the sheath) in order to puncture through tissue (creating a puncture site) for example across a septum of the heart to gain access from the left atrium into the right atrium of the heart. Additionally, as mentioned above, a dilator may be used during a part of the procedure. For example, in combination with the puncture device, a dilator may be advanced to the puncture site to dilate the puncture site to enable additional medical devices to be advanced through the puncture site into the left side of heart. In such procedures, the dilator may be locked or coupled to the introducer or sheath using a locking mechanism during a portion of the procedure allowing the two devices to be advanced concurrently and/or to enable two of the devices to be coupled together thereafter after they are positioned relative to one another. The locking mechanism additionally enables decoupling of the two devices to enable one of the devices to be advanced independently during a part of the procedure.

In conventional systems locking mechanisms are provided that connect two devices at the proximal portions thereof for example along the hub portions, which ensures that the distal portions remain fixed in the desired or correct position while the user guides the sheath and dilator inside the patient anatomy. In some such examples, the direction of the sheath curve is indicated by the side port on the sheath hub and is controlled by rotating the sheath hub. The locking mechanism couples the dilator to the sheath allowing the sheath and dilator to be advanced and/or rotated together.

For example, the once the devices are positioned at the septum prior to puncture for example, the dilator snaps into the sheath hub to connect the two devices. This is done by the user on the proximal end which is the user interface. By connecting the two devices proximally, it ensures the distal portions remain fixed in the correct position while the user guides the sheath and dilator in the patient anatomy.

Certain limitations may be associated with the use of medical devices such as introducers or sheaths and dilators that employ conventional locking mechanisms such as snaps. The limitations of the existing locking mechanisms on these devices may include one or more of the following. The existing locking mechanisms have: snaps which degrade with use, provide insufficient retention force, provide insufficient tactile feedback, and/or generate debris. Additionally, the locking mechanism may not provide desired insertion force and/or removal force.

In some such examples, it may be too difficult to or require too much force to snap or connect the two devices together making it difficult for the user to couple the two devices, and/or may require too much force to unsnap or disconnect the two devices which could lead to loss of positioning of the devices. Conversely, it may be too easy to or require very little force to snap or connect the two devices together and/or may require very little force to unsnap or disconnect the two devices, which may not provide sufficient retention force and may lead to undesired and/or unintentional decoupling of the devices.

Some such conventional medical devices such as sheaths and dilators that require the use of rigid snaps have snap fits that have a rigid ring or bump on the dilator hub that must press into a mating feature on the sheath hub. These rigid snap mechanisms may have one or more of the above noted problems which may include one or more of: (1) degrading with use, (2) providing insufficient retention force, (3) providing insufficient tactile feedback, or generating debris, or (4) not providing a uniform force for locking and providing a uniform force for repeated uses.

Additionally, other problems associated with conventional snap mechanisms is that they require the use of plastic deformation of material, where the snaps are designed to and require that they deform plastically to enable coupling or locking of the two components. Such mechanisms rely on degradation of the snap component to enable locking. As such the initial insertion force value to enable coupling or locking for the first time may be high whereas with multiple uses, including starting from the second or third use for instance, the insertion force required to insert the dilator hub into the sheath hub may decline rapidly. As such the user may need to use a very high force to snap the two devices initially and the user may additionally get a different feel with multiple uses, providing a varying and inconsistent user experience. The prior art snaps require the user to use a varying amount of insertion force to couple the sheath and dilator hubs together to snap the two hubs together. This provides the user with varying feedback on the force that is required in order to snap the two components together.

Such prior art systems rely on locking mechanisms that utilize plastic deformation to provide coupling or locking using a press fit between rigid rings or bumps or tabs on the two medical devices that are being coupled. As such conventional systems rely on plastic deformation and not able to retain their shape during multiple uses and can be deformed or degraded over time.

Furthermore, existing snap mechanism may not adequately couple two devices to allow them to be rotated together and/or allowing the curves of the two devices to be aligned to provide directionality.

As such, there is a need to provide a coupling mechanism that allows two devices to be coupled together, while providing a relatively uniform insertion force and/or removal force in order to couple the two devices and for repeated uses (for example to snap the two devices together). There is additionally a need in the prior art to provide a mechanism that provides one or more advantages of (1) not degrading with use or multiple uses, (2) providing sufficient retention force to enable coupling, (3) providing insufficient tactile feedback (4) generating debris or (5) not providing a uniform force for locking for repeated uses (6) providing sufficient force for locking that is sufficient for retention but the force is not too high that is makes it difficult for the user to snap the two devices together.

Still furthermore, there is additionally a need to provide a mechanism that couples two devices so they can be rotated together and provide directionality by allowing the curves of the two devices to be aligned.

The inventors of the present invention have discovered novel locking mechanism and systems and methods that use the same in an attempt to overcome the limitations associated with prior art locking mechanism and systems.

In one broad aspect, the present inventors have discovered systems and methods that provide a novel locking mechanism comprising a snap fit design that enables flexible coupling between two medical devices such as a sheath and/or dilator. The systems and methods of the present invention attempt to overcome limitations associated with conventional locking mechanisms and systems that utilize rigid snap mechanisms.

Inventors of the present invention have developed a novel locking or coupling mechanism for coupling or locking two medical devices and a system that uses the same. The novel mechanism as provided herein is a releasable coupling or locking mechanism that provides a coupling member or element such as a flexible coupling member that provides a flexible coupling at the interface between the two devices, for example at the interface between the proximal portion of the two devices. In other words in some embodiments of the present invention, a flexible coupling member is provided that allows first and second mating members of a coupling system or arrangement to be releasably coupled to one another.

More specifically, in some embodiments the releasable coupling or locking mechanism defines a flexible coupling mechanism that comprises a flexible snap fit mechanism at the interface between the two devices where the flexible snap fit mechanism provides: a flexible snap member or component (or in other words a flexible coupling member or component) [either independent or attached] at the interface between the proximal portions or in other words mating portions of the two devices.

In other embodiments the releasable coupling or locking mechanism defines a flexible coupling mechanism that comprises flexible a coupling member or component comprising a snap fit mechanism at the interface between the two devices where the coupling mechanism provides: a member or element comprising a moveable and/or a flexible locking member or component (or in other words a moveable and/or a flexible coupling member or component) [either independent or attached] at the interface between the proximal portions of the two devices (or first and second mating members).

In some such embodiments, a coupling element comprising a flexible and/or a moveable member or component such as a flexible snap member or component is used at the interface between the two hubs of the two devices such as a sheath hub and the dilator hub. For example, the flexible snap member or component is provided within the sheath hub, where the flexible snap member or component interacts with the dilator hub to couple it to the sheath hub where the snap member or component itself is flexible and is capable of providing elastic deformation.

Some such embodiments of the present invention provide a flexible locking mechanism comprising a coupling element comprising a flexible locking member or component. In one particular example the flexible locking mechanism comprises defines a flexible snap fit mechanism that relies on elastic deformation to enable releasable coupling between the sheath hub and the dilator hub. More specifically, the flexible snap fit mechanism comprise a flexible locking member or component such as a flexible snap member or component (or interface or assembly) that flexes. As such, the flexible snap fit retains its shape during multiple uses and is not substantially deformed or degraded as the user is not plastically deforming the material as the dilator hub is advanced into the sheath hub. As an additional advantage in some embodiments the flexible snap member or component allows the snap-in force and the snap-out force to be varied.

In some such examples, the coupling element comprising the flexible snap member or component is provided independent from the device hub such as the sheath hub, or in other embodiments the snap member or component is attached to the device hub such as the sheath hub.

In some embodiments, the snap member or component comprises a resilient snap member or component that is provided within the sheath hub that is where the snap member or component [for example comprises a flexible body or body portion] where the body portion and thus the snap member or component itself is flexible and is capable of providing elastic deformation to allow the resilient snap member or component to move out [for example radially] to allow a portion of the dilator hub to pass and move back in [for example against a portion of the dilator hub or into a groove of the dilator hub] to retain it by releasably coupling it to the sheath hub. Then when the dilator is pulled back the resilient snap member or component can move out again to allow the dilator to be removed by disengaging the locking mechanism.

In some such embodiments, the body portion of the resilient snap member or component (and the resilient snap member or component) is configured to change its shape and/or move out of the way upon advancement of the dilator hub within the sheath hub, to allow a portion of the dilator hub to pass, such as a rigid bump or ring on the dilator hub, the body portion of the resilient snap member (and thus the resilient snap member or component) is then configured to move back into its original shape and/or position [for example into a groove of the dilator] in order to retain the dilator hub within the sheath hub to releasably lock the sheath and dilator hubs. Then when the dilator and thus the dilator hub is pulled back the body portion of the resilient snap member or component (and thus the resilient snap member or component) is configured to change its shape and/or move out again to allow the dilator hub to be removed, allowing the body portion of the snap member or component (and thus the snap member or component) to go back to its original shape and/or position.

In a specific example, the snap member or component comprises a resilient snap ring or band that is for example oval shaped that is configured to change its shape to a circular snap ring or band and move out [for example radially] to allow a raised portion of the dilator hub (such as a bump or a ring) to pass past the resilient ring or band (specifically past one or more snaps positioned along the body portion such as the resilient ring or band). The circular resilient ring or band is then configured to change or move back into its original oval shape (an oval snap ring or band) and thus its original position (allowing it to be positioned within a groove of the dilator hub). Specifically, allowing the one or more snaps along the oval resilient snap ring or band to move into a groove of the dilator hub, in order to retain it within the sheath hub to releasably couple the dilator hub to the sheath hub using the flexible locking mechanism. Then when the dilator hub is pulled back the oval snap member or component can move out again to allow the dilator hub to be removed and the snap member or component is configured go back to its original oval shape and position within the sheath hub.

In some such examples, the snaps along with the resilient snap ring or band are flexible and are also capable of elastic deformation allowing the assembly of the snap ring or band and the snaps to flex out of the way (for example radially) upon insertion of the dilator and to move back to its original shape and/or place to couple the sheath hub to the dilator hub. In some such examples, the snaps comprise flexible tabs that along with the snap ring or band are flexible, where the assembly of the snap ring or band and flexible tabs flexes and move out of the way upon advancement of the dilator hub and then moves back to its original shape and/or place to couple the sheath hub to the dilator hub. In some such embodiments the flexible snap member or component is moveable into a groove of the dilator hub (for example as it moves radially back into its original position) and sits within the groove of the dilator hub and may not hug the wall of the groove. In other embodiments, the flexible snap member or component is moveable into and sits within the groove of the dilator hub and may additionally hug the wall of the groove.

In some embodiments of the present invention, a locking mechanism is provides that provides a novel solution for releasably coupling two medical devices, where a moveable coupling member or component or portion is provided within the sheath hub, where the moveable coupling component or portion [attached or unattached] is translatable or moveable out of the way of the dilator hub wider portion (for example radially) as the dilator hub is advanced through and past the opening of the sheath hub. In some such examples the moveable coupling member or component comprises a moveable locking member or component. In some such examples the moveable coupling member or component is a moveable snap member or component. Then once the dilator hub wider portion is past the moveable component or portion—the moveable coupling component or portion is then moveable, for example radially, into the groove of the dilator hub [or in other words dilator hub groove portion]—and the (component or member which in some examples comprises a flexible snap) is thus positioned in the dilator groove [and thus coupled thereto] and as such the effective diameter of the dilator hub is now wider than the sheath hub opening preventing the dilator hub to be readily retracted from the opening in the absence of force.

In other words, once the dilator hub has advanced past the moveable member or component into the sheath hub, the moveable member such as a flexible snap member or component moves radially back into its original shape or configuration enabling the flexible snap member or component [such as a resilient snap ring or band] to fall into place within the dilator hub groove portion which creates a larger effective outer diameter of the dilator hub than the sheath hub opening creating an interference fit for releasably coupling the dilator hub to the sheath hub and preventing the dilator hub to be decoupled from the sheath hub in the absence of force. In other words, an interference fit is created between the moveable coupling member that is seated within the dilator hub groove, and the dilator hub groove. And the moveable coupling member may be seated loosely within the dilator hub groove. This arrangement of the coupling member within the dilator hub groove enables translational locking the sheath and dilator hubs and prevents the dilator hub from being advanced further into the sheath hub and additionally from being retracted as well, as the effective diameter of the dilator hub is greater than the opening of the sheath hub. In other words, the interaction between the moveable coupling member and the distal inner wall of the sheath hub housing (that defines the opening or space within which the moveable coupling member is seated) prevents the sheath hub from being retracted proximally in the absence of force. Similar interaction between the proximal inner wall of the sheath hub housing and the moveable coupling member prevent the dilator hub from being advanced further proximally once it is inserted into sheath hub. Thus the moveable coupling member of the present invention enables translational locking of the sheath and dilator hubs.

As such, in some embodiments, the moveable component functions to block the movement of the dilator hub out of the sheath hub and functions to create an interference fit to prevent movement of the dilator hub in the absence of force. This provides a translation locking mechanism where the dilator hub is not able to advance further into the sheath hub and additionally prevents the dilator from being retracted/disengaged or removed from the dilator hub in the absence of force.

In some such embodiments, a portion of the moveable and/or flexible member or component may be flexible or resilient or the moveable and/or flexible member or component may be partially flexible or resilient. In some such examples, the moveable and/or flexible member or component comprises a spring biased member.

In other embodiments, the moveable member or component may not be flexible or resilient, but is functional to move into the groove of the dilator to block the movement of the dilator hub out of the sheath hub, in the absence of force for instance. In one such example, the moveable locking member or component may comprise one or more loose pieces within the sheath hub that move (for example radially) out of the way when the dilator hub (specifically the dilator hub wider portion) is advanced into the sheath hub and once the dilator hub is advanced further such that the dilator hub groove portion is positioned at the axial location of the moveable locking member or component allowing the loose pieces to fall into place within the dilator hub groove portion which may create a larger effective outer dilator than the sheath hub opening creating an interference fit releasably coupling the dilator hub to the sheath hub and preventing the dilator hub to be decoupled from the sheath hub in the absence of force. However, once a sufficient force is applied the dilator hub may be decoupled from the sheath hub by allowing the loose pieces to move radially out from the groove upon application of a pulling force on the dilator.

As such in some embodiments of the present invention a locking mechanism is provided where the dilator has a smaller effective diameter going into the sheath hub and once in—it has a larger effective diameter by coupling to the member or component (such as a snap member or component) of/in the sheath hub, preventing it from exiting in the absence of force [where force is used for decoupling the component from the dilator hub]. The moveable member or component such as a moveable locking member or component in the sheath hub that creates an interference fit/or interacts with the incoming dilator hub preventing it from exiting—for example by creating a larger effective diameter on the dilator hub. In some such examples, the moveable member or component of the locking mechanism within the sheath hub is a flexible component. In other examples the member or moveable component of the locking component within the sheath hub is a translating or moveable component. In other embodiments, the locking member or component of the locking mechanism may be flexible and/or moveable, and functions to block the movement of the dilator hub out of the sheath hub in the absence of force. In some such embodiments, the moveable locking member or component comprises a flexible locking member or component, for example comprising a resilient material as noted above.

Some such embodiments of the present invention provide an audible click when the flexible or moveable snap member or component of the snap fit mechanism co-operatively or interacts with the dilator hub to enable engagement or coupling between the dilator hub and the sheath hub, and functions to provide the user with an audible indication-such as a clicking sound, indicating that the two hubs have been coupled or effectively locked together. In some such embodiments as noted above, the snap member of component may comprise one or more snaps positioned along a portion thereof such as a body portion, such as a resilient ring or band. In some such examples, the snaps may function to create audible sound or indictor such as a clicking sound to indicate that the two hub portions have been coupled or alternatively to indicate when the two hub portions are then disengaged.

As such embodiments of the present invention provide locking mechanisms that overcome one or more disadvantages of prior art locking mechanisms such as existing snap fits that have a rigid ring or bump on the dilator hub that must press into a mating feature on the sheath hub, as such embodiments of the present invention avoid the disadvantages of locking mechanisms that involve plastic deformation of the bumps/detents on the sheath/dilator hubs, and as such locking mechanism as presently disclosed herein can solve one or more problems of prior art locking mechanisms such as degrading with use, providing insufficient retention force, providing insufficient tactile feedback, and/or generating debris.

A Releasable Coupling Mechanism

In some embodiments of the present invention as shown in FIG. 1A, a releasable coupling mechanism 300 is provided for releasably coupling two members such as a first mating member 100 and a second mating member 200. As additionally shown in FIGS. 1B and 1C, the releasable coupling mechanism 300 comprises a coupling member or component 1000 associated with a first mating member 100 for releasably coupling or engaging a second mating member 200 to the first mating member 100, where the second mating member 200 is receivable by the first mating member 100, for example through an opening 112 thereof. In some such examples, the coupling member 1000 is positioned inside or held within the first mating member 100, as shown in FIG. 1B.

In some such embodiments, the coupling member 1000 has a first state 1000A and a second state 1000B [shown in FIGS. 7A-7B] and is moveable there-between to enable the second mating member 200 to be coupled to the first mating member 100. Specifically, the coupling member 1000 is moveable from the first state 1000A into a second state 1000B upon insertion of the second mating member 200 into the first mating member 100 to allow passage of the second mating member 200 and the coupling member 1000 is moveable thereafter into the first state 1000A to couple the second mating member 200 to the first mating member 100, discussed further herein below Releasable Coupling Assembly In accordance with some embodiments of the present invention releasable coupling assembly 400 is provided that comprises the first mating member 100 and a coupling mechanism 300 as described herein above, as shown in FIGS. 1A, 1B and 1C. More specifically, the releasable coupling assembly 400 comprises, the first mating member 100 and a coupling mechanism 300 comprising a coupling member 1000 associated with the first mating member 100 for releasably coupling a second mating member 200 receivable by the first mating member 100, to the first mating member 100. As noted herein above, the coupling member 1000 has a first state (or configuration) 1000A and a second state (or configuration) 1000B as shown in FIGS. 7A and 7B, as discussed further herein below. As noted herein, the coupling member 1000 is moveable or deflectable from its first state 1000A(FIG. 7A) into its second state 1000B(FIG. 7B) upon insertion of the second mating member 200 into the first mating member 100, as shown, to allow passage of the second mating member 200 there-through and is moveable thereafter into its first state (FIG. 7A) to couple the second mating member 200 to the first mating member 100 of the releasably coupling assembly 400 as shown in FIGS. 1A and 1D.

Releasable Coupling System

Figure 1D:
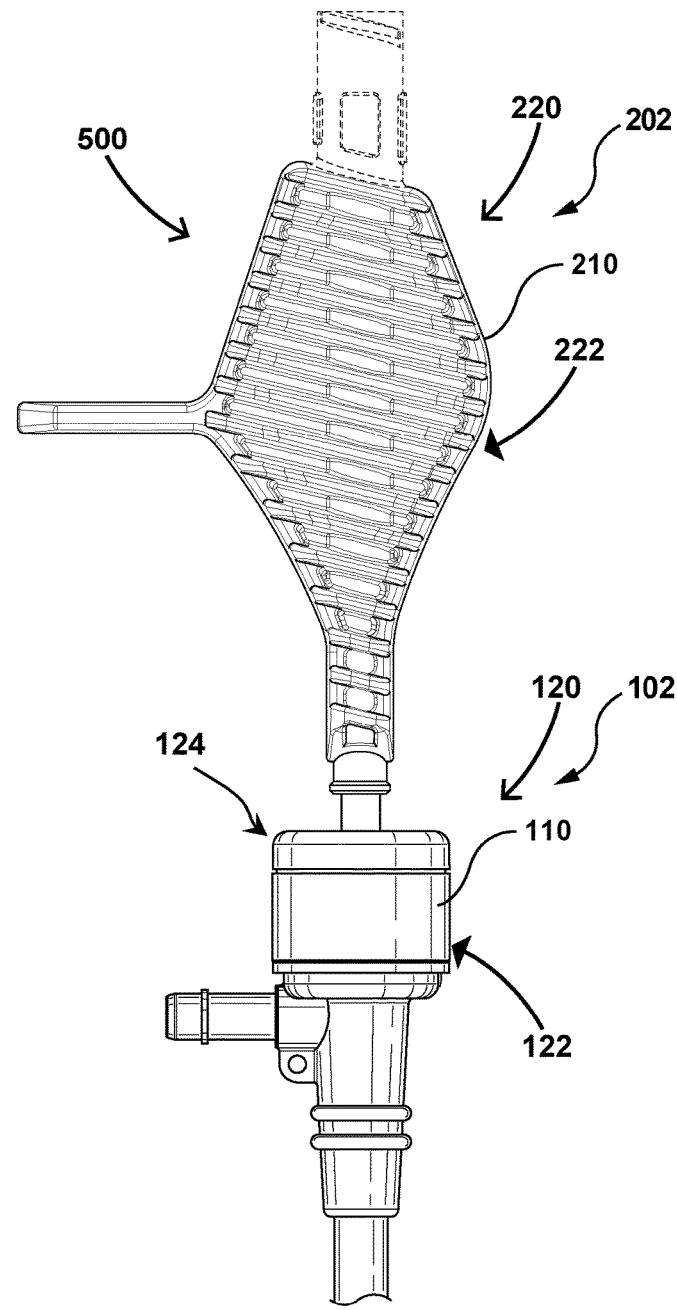
FIG. 1D is a side view of a device, for example a dilator, inserted into the hub of a second medical device, for example a sheath, wherein the sheath comprises a coupling mechanism in accordance with an embodiment of the present invention.
Figure 1C:
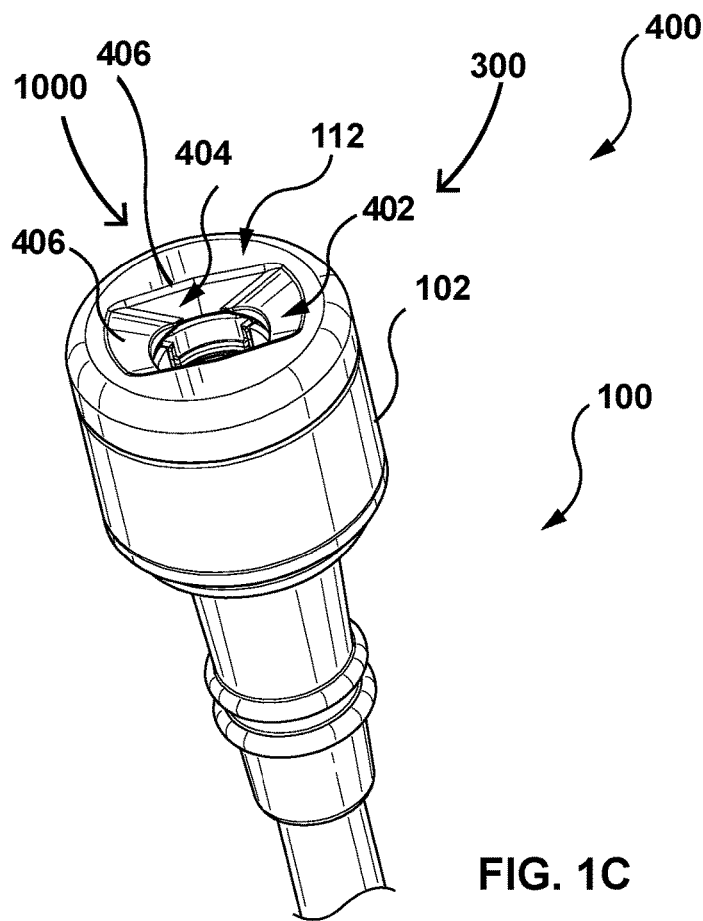
FIG. 1C is a perspective view of the hub, showing a coupling mechanism comprising guides and co-operating features for enabling coupling of two medical devices in accordance with an embodiment of the present invention.
Figure 1B:
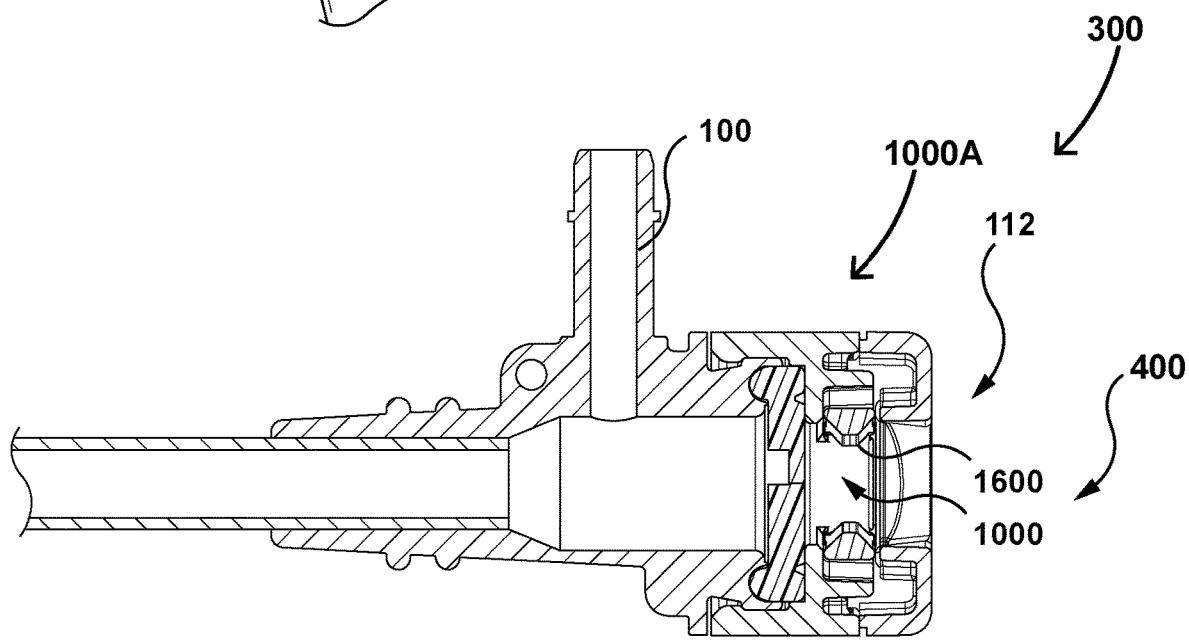
FIG. 1B shows a cross-sectional view of the hub of FIG. 1A and the coupling mechanism incorporated therein, in accordance with an embodiment of the present invention.

As an overview of embodiments of the present invention, in some embodiments of the present invention a coupling system 500 is provided as shown in FIGS. 1A and 1D, comprising a releasable coupling mechanism 300 for coupling two mating members 100, 200 In the embodiment shown, a releasable coupling system 500 is provided that comprises a first mating member 100, a coupling mechanism 300 comprising a coupling member 1000 associated with the first mating member 100 as shown in FIG. 1B, and a second mating member 200 that is receivable by the first mating member 100 to be secured thereto by the coupling member 1000.

For example, the releasable coupling system comprises a releasable coupling system 500 comprises a releasable coupling mechanism or releasable locking mechanism 300 that allows for releasably coupling two mating members 100, 200 that may comprise two devices 102, 202 such as two medical devices such as a sheath 120 and a dilator 220. Specifically, the releasable coupling system comprises a coupling mechanism comprising a coupling member 1000, a first mating member that houses or retains the coupling member 1000 (as shown in FIG. 1B), and a second mating member 200 that is receivable by the first mating member 100 (for example through an opening 112, to be coupled to the first mating member 100 by the coupling member 1000.

In one such embodiment, the first mating member 100 of the releasable coupling system 500 comprises a first handle portion 110 of a first medical device such as a sheath 120. In the example shown, the sheath 120 comprises a sheath hub 122 defining a housing 124, as shown in FIG. 1D, comprising an opening 112 (as additionally shown in FIGS. 1B and 1C) for receiving the second mating member 200 there-through as shown in FIGS. 1A and 1D. Thus, in such embodiments of the releasable coupling system 500 of the present invention, the first mating member 100 comprises a housing 124, as illustrated in FIG. 1D. In some such examples, the coupling member 1000 is functionally coupled to the housing 124 of the first mating member 100, where it may not necessarily be attached or coupled but is functional to interact with the housing upon insertion and removal of the second mating member 200 from the first mating member 100, interaction with the housing is provided in additional detail herein and encompasses functional coupling as the term is used herein.

Additionally in the embodiment shown, the releasable coupling system 500 includes the coupling mechanism 300 comprising the coupling member 1000 (such as a substantially oval disc shaped coupling member 1600 as additionally shown in FIGS. 6A-6D) for securing the second mating member 200 that is inserted into the first mating member 100 as shown in FIG. 1D. In some examples, the coupling member 1000 is held within the first mating member 100. In some examples, the coupling member 1000 is seated or positioned within the mating member.

The releasable coupling system 500 additionally comprises the second mating member 200 that is configured to be inserted within and received by the first mating member 100. In some such embodiments, the second mating member comprises a second handle portion 210 of a second medical device 202 or a part of (such as a dilator 220, shown in FIGS. 1C and 1D) therein, that is received by the opening 112. The second handle portion 210 comprises a dilator hub 222 comprises a second handle wider portion 226 for example such as ridge or a bump/ring 228 and a second handle groove portion or groove o224 (as shown in FIGS. 2A(i), 2A(ii)) for receiving a portion of the coupling member 1000, such as snaps 1630 of a substantially oval disc shaped coupling member 1600 (as shown in FIG. 6A(iii)).

As noted herein above for the coupling mechanism 300, in the coupling system 500, the coupling member 1000 has a first state or configuration 1000A and a second state (or configuration 1000B as shown in FIGS. 7A and 7B, where the coupling member 1000 is moveable from its first state 1000A(which for this particular example relates to a coupling member 1000 having a substantially oval disc shaped configuration 1600 where in the first state the coupling member has or retains its substantially oval disc shaped configuration as shown in FIG. 7A) where it is moveable into its second state 100B(where the substantially oval disc shaped coupling member 1600 moves or flexes into a substantially round or circular disc shaped configuration as shown in FIG. 7B) upon insertion of the second mating member 200 into the first mating member 100 to allow passage of the second mating member 200 there-through and is moveable thereafter into its first state (it goes back into its substantially oval disc shaped configuration as shown in FIG. 7A for this particular example) to couple the second mating member 200 to the first mating member 100. This mechanism is discussed further herein below.

As noted above, in some embodiments of the releasable coupling system, the second mating member 200 comprises a groove 226, and once the coupling member 1000 moves from its second state 1000B to its first state 1000A, the coupling member 1000 is receivable within the groove 226 of the second mating member 200 defining a co-operative engagement/arrangement 1226 there-between for releasably coupling the first 100 and second 200 mating members together.

In one specific example as discussed herein above with respect to FIGS. 7A-7D, once the coupling member 1000 moves from its second state 1000B to its first state 1000A, specifically with respect to the substantially oval disc shaped coupling member 1600. I.e once the coupling member 1600 moves from its substantially round or circular disc shaped configuration in its second state as shown in FIG. 7B, back to its substantially oval disc shaped configuration 1000A as shown in FIG. 7A, it is receivable within the groove 226 of the second mating member 200 defining a co-operative engagement or arrangement 1226 there-between for releasably coupling the first 100 and second 200 mating members together.

In accordance with a releasable coupling system 500 of the present invention, in some embodiments the coupling member 1000 defines a first corresponding co-operative engagement feature or portion 1006 as shown in FIG. 6D(i), where in some examples, the first corresponding co-operative engagement feature 1006 comprises snaps 1030 of the coupling member 1000, such as snaps 1630 of the substantially oval disc shaped coupling member 1600. In some such examples, a second corresponding co-operative engagement feature/portion 206 is provided on the second mating member 200, which in some examples comprises a groove 226 of the second mating member 200, as shown in FIG. 6B and as shown in FIGS. 2A(i), 2A(ii) as discussed previously herein.

In the releasably coupling system 500 as shown in FIG. 6B, in accordance with some examples of the present invention, wherein the first corresponding co-operative engagement feature or portion 1006 of the coupling member 1000 is operable to co-operatively engage to the second corresponding co-operative engagement feature or portion 206 of the second mating member 200 defining a co-operative engagement/arrangement there-between the first and second corresponding portions 1006, 206 to for releasably coupling the first and second mating members 100, 200.

In some such embodiments of the releasable coupling system 500, the releasable coupling mechanism 300 comprises and provides a translational locking mechanism for preventing the first and second mating members 100, 200 from moving translationally with respect to one another. In some such examples, the coupling member 1000 is functionally coupled to the housing 124 of the first mating member 100. In some such examples, the housing 124 for example in the case of a sheath 120 a housing base portion 124b and sheath hub cap 126. In some such examples the sheath hub 122 comprises a hub portion 125 that is coupled to the housing 124. The housing 124 for example as defined by housing base portion 124b and sheath hub cap 126 interacts with the coupling member 1000 to prevent translational movement of the second mating member 200 with respect to the first mating member 100.

As described herein above, as shown in FIGS. 6A(iii) and 6A(iv), the coupling member 1000 of the coupling mechanism 300 interacts in co-operative engagement [at least functionally] with the second mating member 200, and functionally engages the two in the absence of force. The housing 124 interacts to prevent movement of the coupling member translationally in the proximal and distal directions [specifically the sheath hub cap 126 prevent proximal retraction of the second mating member 200 such as a dilator 220 and the base of the housing base portion 124b prevents distal movement of the mating member 200 such as the dilator 220 preventing further advancement of the dilator 220 into the sheath 120, and as such translationally locking the first mating member [such as the sheath 120] and the second mating member [such as the dilator 220].

Releasable Coupling Member

As above, in embodiments of the present invention, a releasable coupling mechanism 300 is provided comprising a coupling member 1000, where the releasable coupling mechanism comprises a translational locking mechanism preventing the first and second mating members 100, 200 from moving translationally with respect to one another. In other words the coupling member 1000 enables translational locking of the first and second mating members 100, 200.

General Coupling Member [General Housing Configuration-Coupling Member is Functionally Coupled to the Housing]

As described herein above, some embodiments of the present invention provide a releasable coupling mechanism 300 where the coupling mechanism 300 further comprises a housing 124 of the first mating member 100 wherein the coupling member is functionally coupled to the housing 124 of the first mating member 100 and functions to retain the second mating member 200 once it is inserted into the housing 124. The coupling member 1000 is moveable to couple to the second mating member 200 to secure it to the first mating member. The coupling member 1000 is additionally configured to interact 124 with the housing to prevent removal of the second mating member 200 in the absence of force and to prevent translational movement of the coupling member 100 and thus the second mating member 200 coupled thereto, either distally prevent further advancement into the first mating member 100 or retraction distally. The interaction may comprise the coupling member 1000 abutting against the proximal inner surface of the housing 124 or a distal inner surface of the housing 124 to prevent translation thereof.

In some such examples of a releasable coupling mechanism 300 of the present invention, for example as shown in FIGS. 1A-1D, the coupling member 1000 is held within the first mating member 100, for example within the housing 124.

[Coupled/Attached Housing Configuration-Coupling Member is Coupled to the Housing]

Straight Cantilever and u-Shaped Cantilever

In some such embodiments, where the coupling member 1000 is functionally coupled to the housing 124, the coupling member 1000 is coupled to a housing 124 of the first mating member 1000, with reference to FIG. 2A-2B, as well as FIGS. 3A-3C, 4A-4C, FIGS. 5A-5F. In some such examples, the coupling member 1000 is attached to the housing 124.

Straight Cantilever [Coupling Member is Integrally Formed with the Housing]

With specific reference now to FIGS. 2A(i)-2A(ii), and additionally 2B(i)-2B(ii), the coupling member 1000 is formed integrally with the housing 124 of the first mating member 100, specifically a first 102 such as a medical device such as the sheath 120 as noted herein above. In some such embodiments of a releasable coupling mechanism 300, the coupling member 1000 comprises at least one cantilever 1010 as shown.

Straight Cantilever

In the example shown in FIGS. 2A(i)-2B(ii), the at least one cantilever 1010 comprises at least one straight or simple cantilever 1200, as shown. In the specific instance of this example the at least one straight or simple cantilever 1200 is formed integrally with the housing 124

(for example with a cap thereof such as a sheath hub cap 126) shown in FIG. 2A(ii). In some such embodiments, the coupling member 1000 comprising the straight or simple cantilever 1200 comprises a flexible coupling member, it is able to flex from its first state or configuration 1000A [as shown in FIG. 2A(i)], for example radially outwards into its second state or configuration 1000B(as shown by directional arrows R), to allow the second mating member 200 to pass through the opening 112 of the first mating member 100, and then the straight or simple cantilever 1200 flexes back into its [FIG. 2A-2B]

In the illustrated example of the the at least one straight or simple cantilever comprises one or more retaining arms or members 1212 as shown in FIG. 2A(i). In some such embodiments, the one or more retaining arms or members 1212 terminate in one or more snaps 1230. In additional examples as shown in FIGS. 2B(i), (ii) the at least one straight or simple cantilever 1200 comprises two or more straight or simple cantilevers 1200x, 1200y as shown (or at least two cantilevers 1200x, 1200y as shown).

In the embodiment shown, each of the two or more straight or simple cantilevers 1200x, 1200y is deflectable to move from the first state 1000A into a second state 1000B upon insertion of the second mating member 200 into the first mating member 100 to allow passage of the second mating member 200 there-through and the coupling member 1000 is capable of returning thereafter into the first state 1000A to couple the second mating member to the first mating member as shown in FIG. 2B(ii). As noted above, in some examples each of the two or more straight or (simple) cantilevers 1200 is deflectable in a radial direction to move between the first state 1000A and the second state 1000B.

Still furthermore, in the embodiments illustrated in FIGS. 2A(i)-2B(ii) of the releasable coupling mechanism 300, each of the two or more straight or simple cantilevers 1200 is moveable in a plane P1 that is substantially in plane with the direction of advancement D of the secondary mating member 200 into the housing 124 for insertion therein. [FIG. 2A]. In other words each of the two or more straight or simple cantilevers 1200 is moveable in a plane P1 that is substantially in plane with a plane DI that is substantially in plane with the direction of advancement D (or alternatively direction of removal) of the secondary mating member 200.

U-Shaped Cantilevers [Coupling Member is Attached to the Housing]

In some embodiments, of the present invention, as discussed previously herein above, the coupling member 1000 is functionally coupled to the housing 124. In an example of this, the coupling member 1000 is held within the housing. In a specific instance, the coupling member 1000 is coupled to a housing 124 of the first mating member 1000, as discussed previously with reference to FIG. 2A(i)-2B(ii) above, as well as FIGS. 3A-3C, 4A-4C, FIGS. 5A-5F.

With reference now to FIGS. 3A(i)-3C, 4A-4C, FIGS. 5A-5F, similar to examples discussed previously herein above, the releasable coupling mechanism 300 of the coupling system 500 comprises a coupling member 1000 comprising at least one cantilever 1010 (as shown in FIGS. 3B, 3C, and additionally FIGS. 4B,4C and FIGS. 5B, 5C) to enable a second mating member 200 of the coupling system 500 to be coupled to the first mating member 100, where the coupling member 100 is held within the housing 124. In some such examples, the coupling member 1000 is attached to the housing 124. In some embodiments, the coupling member 1000 comprises at least one u-shaped cantilever 1300 as shown, which in some instances comprises an elastic u-shaped cantilever 1300 that is substantially elastic.

In some such embodiments, as shown in FIG. 3A(i)-3D, 4A-4C, 5A-5F, the at least one u-shaped cantilever 1300 comprises a pair of u-shaped cantilevers 1300.

Standard U-Shaped Cantilever

Coupling Member Coupled to the Housing

With reference now to FIGS. 3A(i) and 3A(iii), as well as FIGS. 3D(i) and 3D(ii), the one or more one u-shaped cantilevers 1300 are held within the housing 124, specifically a housing base portion 124b that holds the substantially u-shaped cantilever 1300. In some examples, the housing base portion 124b is coupled to a hub portion 125. The substantially u-shaped cantilever 1300 is substantially held within and coupled to the housing base portion 124b. As shown, in some such embodiments, the substantially u-shaped cantilever 1300 is substantially exposed along a proximal face thereof and forms the proximal outer face of the first mating member 100 as shown in FIG. 3A(ii). In some such embodiments, the coupling member 1300 comprises a pair of standard u-shaped cantilevers 1301, as shown in FIGS. 3A(i) to D(ii), where the distal to proximal cross-section view as shown in FIGS. 3B and 3C defines substantially u-shaped cantilevers.

Coupling Member is Contained within the Housing

Alternatively, in some such embodiments of the present invention, as shown in FIGS. 5A(i), 5A(ii), and 5A(iii), the pair of u-shaped cantilevers are substantially contained within the housing 124 defining substantially contained u-shaped cantilevers 1303, as shown in FIG. 5A(iv). Specifically, as shown in FIGS. 5A(i) and 5A(iii) the u-shaped cantilevers 1300 are substantially contained within or retained by the housing 124 as defined by the housing base portion 124b and a hub cap 126 that together define the housing 124. In the illustrated embodiment, the housing base portion 124b is formed integrally with the hub cap 126, and thus the housing 124 of the first mating member 100 of the coupling assembly 400, is formed integrally and comprises a substantially unitary construction or piece. As such, the u-shaped cantilevers 1300 are substantially contained within the integrally formed housing 124.

Alternatively in some additional embodiments, as shown in FIGS. 5D(i), 5D(ii), 5D(iii), and 5D(iv), the housing 124 is formed from a two part housing, comprising a housing base 124b and a separate hub cap such as a sheath hub cap 126 that are coupled together for example using a snap fit arrangement as shown in FIG. 5E(i). As such, in some embodiments, the housing 124 comprises a housing base 124b and hub cap 126 and the u-shaped cantilevers are substantially contained within the housing base 124b and the hub cap 126 that together function to retain the substantially u-shaped cantilevers 1300 within the housing as shown in FIG. 5E(ii), defining contained u-shaped cantilever coupling members 1303 as above.

Standard U-Shaped Cantilever-Insertion and Removal Forces

In the example shown the U-shaped cantilevers have retaining snap arms or members 1312 that terminate in snaps 1330 as shown in FIG. 3B, 3C (as well as FIGS. 4B, 4C and 5B, 5C). The snaps additionally have dual ramps 1333A, 1333B, where the first ramp 1333A of said dual ramps defines an insertion force and where the second ramp 1333B of said dual ramps defines the removal force where the ramp angles (Fi, Fr) create a component of force that compresses the snaps 1333. In some such examples, the angles on the first and second ramps (or in other words insertion and removal ramps) 1333A, 1333B may be varied to define respective insertion and removal forces. In some such examples, the first and second ramps 1333A, 1333B have varying (different) ramp angles defining varying (different) respective removal and insertion forces. In other examples, the first and second ramps 1333A, 1333b have substantially equivalent ramp angles defining substantially equivalent removal and insertion forces.

Figure 5B:
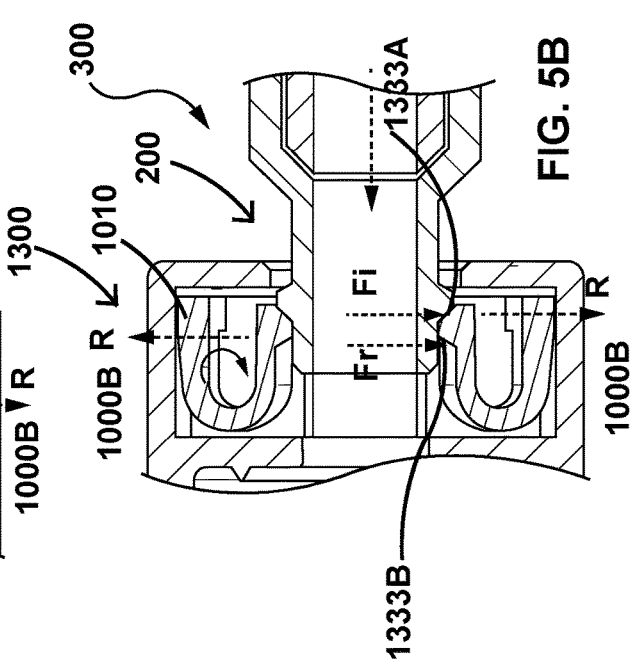
FIGS. 5B and 5C, respectively, are cross-sectional views showing a device being inserted through an alternate embodiment of a coupling mechanism, and the device being removed from the coupling mechanism.
Figure 5C:
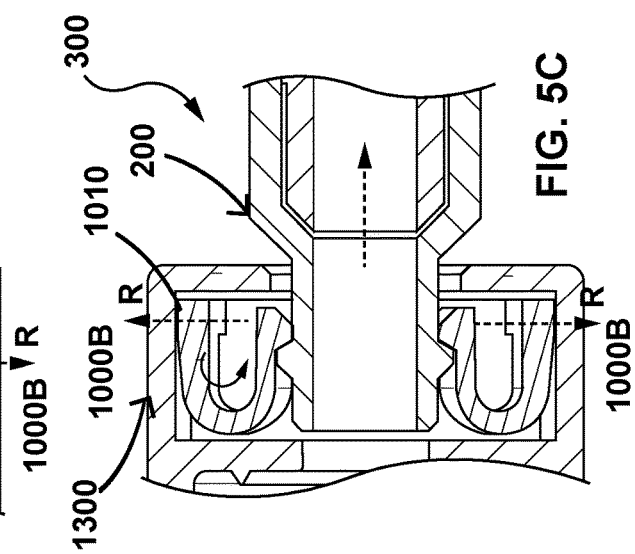

In the specific example shown in FIGS. 3B, 3C, (and additionally in FIGS. 5B, 5C and FIGS. 5F(i), 5F(ii)) the insertion force and the removal force may be varied. In some instances, the force may be varied by a moment created on the snap arm 1312. Specifically as shown in FIGS. 3B, 5B and 5F(i), as the second mating member 200 is advanced into the first mating member 100, the insertion force will create a moment on the snap arm or member 1312 which will increase the force required to overcome snap (in other words the force required to move the substantially u-shaped coupling member 1300 from its first configuration 1000A into its second configuration. In still other words, in some embodiments, the coupling member 1000 such as u-shaped coupling member 1300 is effectively biased in first state or configuration 1000A, and the moment on the snap arm 1312 will effectively increase the force required to overcome this bias in order to move the u-shaped coupling member into its second state or configuration.)

Conversely, upon removal of the second mating member 200 from the first mating member 100 as shown in FIG. 3C (and additionally FIGS. 5C and 5F(ii)), the removal force will create a moment on the snap arm 1312, which will decrease the force required to overcome snap (in other words the force required to move the substantially u-shaped coupling member 1300 from its first configuration 1000A into its second configuration. In still other words, in some embodiments, the coupling member 1000 such as u-shaped coupling member 1300 is effectively biased in first state or configuration 1000A, and the moment on the snap arm 1312 will effectively decrease the force required to overcome this bias in order to move the u-shaped coupling member into its second state or configuration.) In some such embodiments, the angle of the second or removal ramp 1333B may be provided as a relatively steep angle for example in comparison to the angle of the first or insertion ramp 1333A, in order to increase the removal force to provide relatively uniform insertion and removal forces.

Inverted U-Shaped Cantilever-Coupling Member Contained with the Housing

In other embodiments of the present invention, as illustrated in FIGS. 4A(i), 4A(ii), 4A(iii) and 4A(iv), the coupling member 1000 comprising u-shaped cantilevers 1300 comprises a pair of inverted u-shaped cantilevers 1302. As additionally illustrated in FIGS. 4A(i), 4A(ii), 4A(iii) and 4A(iv), the substantially u-shaped cantilevers 1300 are held within the housing 124, specifically the base portion 125b of the housing 124, as shown and form the proximal face of the first mating member 100 (specifically with reference to FIG. 4A(iv). In these embodiments, the coupling members 1000 comprising the u-shaped cantilevers 1300 are coupled to the housing 124, specifically base portion 125b of the housing 124.

Figure 4B:
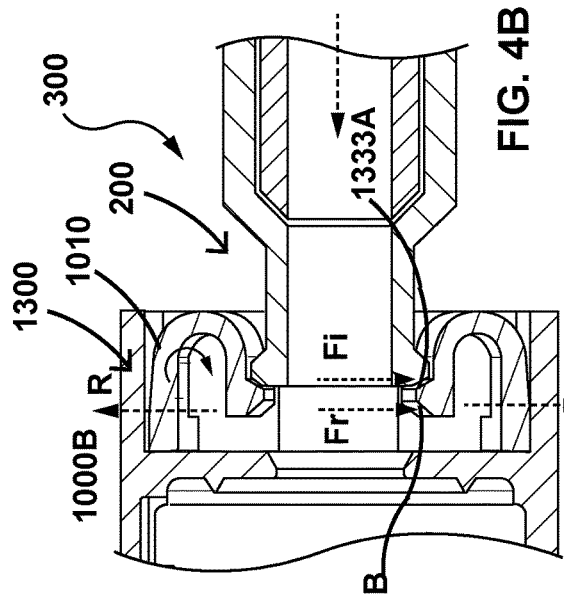
FIGS. 4B and 4C, respectively, are cross-sectional views showing a device that is being inserted through an embodiment of a coupling mechanism, and the device being removed from the coupling mechanism.
Figure 4C:
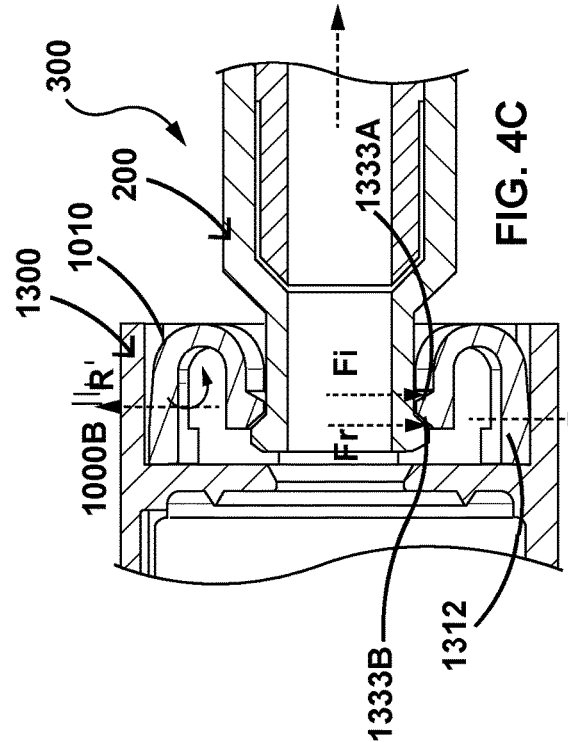

Similar to embodiments discussed previously with respect to FIGS. 3B and 3C, in the specific example shown in FIGS. 4B, 4C, the insertion force and the removal force may be varied. In some instances the force may be varied as a result of a moment created on the snap arm 1312. Specifically as shown in FIG. 4B, as the second mating member 200 is advanced into the first mating member 100, the insertion force will create a moment on the snap arm or member 1312 which will decrease the force required to overcome snap (in other words the force required to move the substantially u-shaped coupling member 1300 from its first configuration 1000A into its second configuration. In still other words, in some embodiments, the coupling member 1000 such as u-shaped coupling member 1300 is effectively biased in first state or configuration 1000A, and the moment on the snap arm 1312 will effectively decrease the force required to overcome this bias in order to move the u-shaped coupling member into its second state or configuration.)

Conversely, upon removal of the second mating member 200 from the first mating member 100 as shown in FIG. 4B, the removal force will create a moment on the snap arm 1312, which will increase the force required to overcome snap (in other words the force required to move the substantially u-shaped coupling member 1300 from its first configuration 1000A into its second configuration. In still other words, in some embodiments, the coupling member 1000 such as u-shaped coupling member 1300 is effectively biased in first state or configuration 1000A, and the moment on the snap arm 1312 will effectively increase the force required to overcome this bias in order to move the u-shaped coupling member into its second state or configuration.)

In some such embodiments, the angle of the first or insertion ramp 1333B may be provided as a relatively steep angle for example in comparison to the angle of the second or removal ramp 1333A, in order to increase the required insertion force to provide relatively uniform insertion and removal forces.

U-Shaped Cantilever-Structure

In some such embodiments of the present invention, as shown in FIGS. 3A(i)-3D(ii), 4A(i)-4C, 5A(i)-5F(ii)], the coupling member 1000 comprising the u-shaped cantilever 1300 comprises a moveable coupling member 1000 where it is moveable between the first and the second states 1000A, 1000Bf. Additionally, in the examples shown, the coupling member 1000 comprises a flexible coupling member, specifically the u-shaped cantilever 1300 is flexible enabling the cantilever arms 1312 to flex between the first state 1000A and the second state 1000B. In still further examples of the coupling member 1000 that embodies the u-shaped cantilever 1300, the u-shaped cantilever 1300 and thus the cantilever arms 1312 comprise a resilient material, thus defining a resilient coupling member 1000.

In still further embodiments of the present invention, the coupling member 1000 comprises an elastic coupling member that is elastically deformable to transition between the first and the second states 1000A, 1000B and substantially avoids plastic deformation. In some such examples, the coupling member 1000 remains in the elastic region of the strain curve. Thus, in some embodiments where the u-shaped cantilever 1300 is provided as outlined herein, the cantilever sections, specifically the cantilever arms 1312 are elastically deformable.

In some such embodiments, each of the pair of u-shaped cantilevers 1300 is deformation, specifically elastically deformable to move from the first state 1000A into a second state 1000b upon insertion of the second mating member 200 into the first mating member 100 to allow passage of the second mating member 200 there-through and the coupling member 1000 defined by the u-shaped cantilever 1300 is capable of returning thereafter into the first state 1000A to couple the second mating member 200 to the first mating member 100. In some such examples, each of the pair of u-shaped cantilevers 1300 is elastically deformable in a radial direction to move between the first state 1000A and the second state 1000B, for example as shown in FIGS. 3B-3C, 4B-4C, 5B-5C).

In some such embodiments, each of the pair of u-shaped cantilevers 1300 is moveable in a plane P1 as shown in FIG. 3B (but is applicable to FIGS. 3C, 4B,4C, 5B, 5C as well) that is substantially in plane with the direction D of advancement of secondary mating member into the housing for insertion therein (or removal therefrom).

In other words each of the pair of u-shaped cantilevers 1300 is moveable in a plane P1 that is substantially in plane with a plane DI that is substantially in plane with the direction of advancement D (or alternatively direction of removal) of the secondary mating member 200 into/from the first mating member 100.

Alternatively in some embodiments, the pair of u-shaped cantilevers 1300 is moveable in a plane p2 that is perpendicular to the direction D of advancement of second mating member 200 into the housing 124 for insertion therein (extending into and out of FIG. 3B as shown.

Substantially Annular Cantilever-Coupling Member Contained with the Housing

In alternate embodiments of the present invention, as shown in [FIGS. 6A(i)-6F(iv), 7A-7D, 8A-8F(iii), 13A-13D, 14A-14F(iii)], a releasable coupling member 1000 is provided where the coupling member 1000 is substantially contained or retained within the housing 124. In the embodiments shown the coupling member 1000 is substantially free floating or loose within the housing 124.

Specifically with reference to FIGS. 6A(i)-6F(iv), in accordance with an embodiment of the present invention a coupling mechanism 300 is provided comprising a coupling member 1000 comprises at least one cantilever 1010 (or in other words a cantilever portion or segment 1010), as shown in FIG. 6D(i). In the illustrated example, the at least one cantilever 1010 comprises a simply supported beam configuration. Specifically as shown, the at least one cantilever 1010 comprises two cantilevers 1010 (or in other words comprises a pair of cantilever portions or segments).

With reference again to FIG. 6D(i), a pair of cantilevers 1010 that are coupled together. As shown in some embodiments, the two cantilevers 1010 comprise two substantially straight segments(S) (or in other words substantially straight portions or sections) that are coupled together using one or more arcuate segments (C), as shown in FIG. 8A. In a specific instance of this as shown, each of the two straight segments(S) of the cantilevers 1010 are coupled together at each of their respective ends by an arcuate (C) segment.

In some of the embodiments shown, each of the two cantilevers 1010 comprise deflectable portions or regions, where each of these deflectable portions are defined by a simply supported beam configuration. In the specific configuration shown, the substantially straight segments(S) define the deflectable portions where maximum deflection (M) is substantially along the mid-point of the substantially straight segments(S). In some such examples, each of the deflectable portions comprise one or more retaining arms 1612 where the one or more retaining arms comprise one or more snaps 1630.

In one specific example, the coupling member 1000 in accordance with a coupling mechanism 300 of the present invention, comprises a substantially annular disc shaped configuration 1601, [or in other words the coupling member substantially comprises an annular disc] similar to the configurations shown in FIGS. 7A and 7B. In a specific instance of this example, the coupling member 1000 comprises a substantially oval disc shaped configuration [or in other words the coupling member substantially comprises an oval disc], with reference again to FIG. 6D(i) and FIG. 8A. As a feature of this, the substantially oval disc shaped coupling member 1600 comprises one or more retaining arms 1612 that terminate in one or more snaps 1630.

In the embodiments illustrated in FIGS. 6A(i)-6F(iv), 7A-7D, 8A-8F(iii), 13A-13D, 14A-14F(iii), the substantially oval disc shaped coupling member 1600 is functionally coupled to the housing 124 but in this particular embodiment it is substantially not coupled or remains unattached or unengaged to the housing during use so that it is moveable feely within the housing 124. Specifically with reference to FIGS. 6D(ii), 6E(i) and 6E(ii), the the substantially oval disc shaped coupling member 1600 is housed within a housing base portion 124b of a sheath hub 122 and is retained therein by the sheath hub cap 126. As such, the combination of the housing base portion 124b and the sheath hub cap 126 form an enclosure to enclose the substantially oval disc shaped coupling member 1600 therein as additionally shown in FIG. 6F(i).

As outlined previously herein above with reference now to FIG. 6E(ii), (as well as FIG. 6F(i) 6F(ii), 6F(iii) which show an alternate second mating member 200) the housing 124, for example as defined by housing base portion 124b and sheath hub cap 126 interacts with the substantially oval disc shaped coupling member 1600 to prevent translational movement of the second mating member 200 with respect to the first mating member 100, once the second mating member 200 is inserted into the first mating member 100 as shown in FIG. 6F(iv).

In some such examples, The housing 124 interacts to prevent movement of the coupling member translationally in the proximal and distal directions [specifically the sheath hub cap 126 prevent proximal retraction of the second mating member 200 such as a dilator 220 and the base of the housing base portion 124b prevents distal movement of the mating member 200 such as the dilator 220 preventing further advancement of the dilator 220 into the sheath 120, and as such translationally locking the first mating member [such as the sheath 120] and the second mating member [such as the dilator 220]. Furthermore, as shown in FIGS. 6B and 6C, the substantially oval disc shaped coupling member 1600 and specifically the snaps 1630 thereof will rub against the distal face 124f of the housing base portion 124b, and the friction will thereby increase the insertion force as shown in FIG. 6B. Conversely, the substantially oval disc shaped coupling member 1600 and specifically the snaps 1630 thereof will rub against the proximal face 126f of the sheath hub cap 126, and the friction will thereby increase the removal force. In some such examples, the substantially oval disc shaped coupling member 1600 is functionally coupled to the housing 124 in that it may not necessarily be attached or coupled (as provided in this embodiment) but is functional to interact with the housing upon removal or insertion of the second mating member 200 to facilitate insertion and removal of the second mating member 200 and coupling it to the first mating member 100.

In some such embodiments of the present invention, the coupling member 1000 such as the substantially oval disc shaped coupling member 1600 comprises a substantially flexible coupling member 1000. In specific embodiments of the present invention, as shown in FIGS. 7A-7D, the substantially oval disc shaped coupling member 1600 is deformable, wherein the coupling member comprises an elastic coupling member that is elastically deformable.

In other words in some embodiments of the present invention, the coupling member 1000 substantially comprises a snap ring or band 1601, which may have a configuration as shown in FIG. 7A or 7B. In a specific example, the coupling member 1000 comprises a substantially oval snap ring or band 1600 as additionally shown in FIG. 8A. In some such embodiments, the coupling member 1000 comprises a substantially annular cantilever.

Substantially Annular Cantilever-Function

In the embodiments shown where the coupling member 1000 comprises a substantially oval disc shaped coupling member 1600, the coupling member 1000 that has a substantially oval disc-shaped configuration in its first state 1000A(FIG. 7A) and substantially round or circular disc-shaped configuration in its second state 1000B (FIG. 7B). The substantially oval disc shaped coupling member 1600, is deflectable to move (for example radially) from its oval disc-shaped configuration in its first state or configuration 1000A into its substantially round or circular disc-shaped configuration 100B in its second state upon insertion of the second mating member 200 into the first mating member 100, as shown in FIG. 6B and FIG. 8B, to allow passage of the second mating member 200 there-through and the a substantially oval disc shaped coupling member 1600, is capable of returning thereafter into the first state 1000A defined by the oval configuration to couple the second mating member 200 to the first mating member 100, as shown in FIG. 6C and FIG. 8F(iii).

Alternatively, the substantially oval disc shaped coupling member 1600 (or alternatively substantially oval snap ring or band 1600) has a first engaging configuration in its first state 1000A which comprises a substantially oval disc shaped configuration [or a substantially oval configuration] and wherein the coupling member has a second non-engaging configuration in its second state 1000B which comprises a substantially circular disc shaped configuration [or a substantially round or circular configuration]. The substantially oval disc shaped coupling member 1600 is moveable (for example radially) into its second non-engaging configuration comprising the substantially circular disc shaped configuration upon insertion of the second mating member 200 into the first mating member 100 (FIGS. 6B and 8F(i)) to enable the second mating member 200 to advance therein and is moveable thereafter into its first engaging configuration comprising the substantially oval disc shaped configuration (as shown in FIG. 6C, FIG. 8F(iii)) to couple the second mating member 200 to the primary or first mating member 100.

In some such examples, with reference to FIGS. 6F(i), 6F9ii), 6F(iii), 6F(iv) the substantially oval disc shaped coupling member 1600 (or alternatively substantially oval snap ring or band 1600) is elastically deformable to move between the first state 1000A and second state 1000B. More specifically in some examples, the substantially oval disc shaped coupling member 1600 (or alternatively oval snap ring or band is moveable outwards, for example radially, into its second non-engaging configuration having a substantially round configuration 1000B upon insertion of the second mating member 200 into the housing of the first mating member 100 [to allow the second mating member 200, specifically to allow a raised portion of the dilator hub 222 (such as a bump or a ring 228) to advance into the housing 124 of the first mating member 100 (to pass past the substantially oval disc shaped coupling member 1600 (or alternatively resilient snap ring or band) specifically past one or more snaps 1630 positioned along the body of the coupling member]. The substantially oval disc shaped coupling member 1600 is moveable thereafter into its first engaging configuration comprising a substantially oval configuration 1000A to couple the second mating member 200 to the primary or first mating member 100 (in other words the circular resilient ring or band is then configured to change or move back into its original substantially oval shape or configuration (a substantially oval snap ring or band) and thus its original position (allowing it to be positioned within a groove 226 of the dilator hub 222.

As noted herein, wherein the substantially oval disc shaped coupling member 1600 is elastically deformable in a radial direction [R] (as outlined in FIGS. 6B, 6C and FIGS. 8B, 8C) to move between the first state 1000A and the second state 1000B.

Snap Force being Independent of the Hub Length

In some embodiments of the each of the pair of cantilevers 1010 of the substantially oval disc shaped coupling member 1600 (as shown in FIG. 6D(i), FIG. 8A) is moveable in a plane [P2] that is perpendicular to the direction of advancement [D] of secondary mating member 200 into the housing 124 for insertion therein.

In some such embodiments, the snap force [i.e. the force required for coupling the second mating member 200 to the first mating member 100 using the coupling mechanism 300] is independent of a proximal length of the first mating member 100. In other words, the force required to enable the substantially oval disc shaped coupling member 1600 to move from its first state 1000A to its second state 1000B to enable coupling, is independent from the length of the first mating member 100, such as a length of a medical device hub such as a dilator hub 122. As a result in some such examples, the frictional forces from insertion of the second mating member into the first mating member 100 against the coupling member 1000 can be minimized and as a result there is reduced drag. As a result additional frictional forces are substantially not introduced and are not additive to the snap force required to deflect the coupling member 1000 to enable coupling or in other words snapping in and snapping out of the second mating member 200. As such the insertion and removal forces are substantially determined by the coupling member 1000 (specifically the substantially oval disc shaped coupling member 1600 with reference to FIGS. 8A, FIG. 8F(ii)) which may alternatively be referred to as a racetrack.

In some embodiments of the present invention the insertion and removal force [Fi] and [Fr] are about 15 Newtons. In other embodiment.

Coupling Member is Flipped Sideways so it Isn't Obstructing View of the Valve

In some embodiments of the present invention, as shown in FIG. 8F(i) and FIG. 8Ff(iii), the first mating member 100, specifically comprising a first device 102 comprising a medical device (such as a sheath 120) has a medical device hub 104 that further comprises a valve 150, wherein the coupling member 1000 (specifically the substantially oval disc shaped coupling member 1600) is oriented in a plane p2 that is perpendicular to the direction of advancement D of the second mating member 200 (as shown in FIG. 8A), whereby it does not substantially hinder visibility of the valve 150 from the user. In other words the coupling member 1000 in the orientation shown does not substantially require use of the hub length (L) for example as defined by the length of the housing 124 as shown in FIG. 6F(iii), for the cantilever 1010 lengths. In some such embodiments, the coupling mechanism 300 utilizes the width of the housing 124, as defined by the real estate provided by the diameter of the housing 124. This ensures that the snapping force is independent of the hub length (L) and helps optimize visibility of the valve 150 through the opening 112 for the user by allowing it be positioned in relative proximity to the opening 112.

Insertion Force and Removal Force being Substantially Equivalent/Uniform

In some embodiments of the present invention, as also discussed previously hereinabove, with reference now to FIGS. 8F(i), 8F(iii), The coupling member 1000, specifically the substantially disc shaped coupling member 1600 as noted previously comprises cantilever arms or retaining arms or members 1612 that have snaps 1630 for example along the mid portion of the retaining arms or members 1612 at the region of maximum deflection. In some such examples of releasable coupling mechanism 300 the snaps 1630 additionally have dual ramps 1633A, 1633B, where the first ramp 1333A of said dual ramps defines an insertion force and where the second ramp 1333B of said dual ramps defines the removal force where each of the ramp angles (Fi, Fr) create a component of force that compresses the snaps 1630.

In some embodiments, the insertion force [Fi] for inserting the second mating member 200 into the coupling mechanism 300 to be coupled to the first mating member 100 by the coupling member 1000 (specifically the substantially oval disc shaped coupling member 1600) is substantially equivalent to the removal force [Fr] for removing the second mating member from coupling mechanism to be disengaged from the first mating member. [FIG. 8A-8F] In some such examples, the angles on the first and second ramps (or in other words insertion and removal ramps) 1633A, 1633B may be varied to define respective insertion and removal forces. In some such examples, the first and second ramps 1633A, 1633B have varying (different) ramp angles defining varying (different) respective removal and insertion forces, as shown in FIG. 8C. For example FIG. 8C provides a greater or steeper angle on the first ramp or insertion ramp 1633A compared to the ramp angle for the second or removal ramp 1633B, which would increase the insertion force [Fi] in comparison to the removal force (for example where the insertion force is the force required to utilize the coupling mechanism for example to snap the second mating member 200 in using the snap mechanism 300 as shown). As such, in the specific example shown in FIGS. 8C, embodiments of the present invention provide a means to vary or in other words provide a varying or different insertion force [Fi] and the removal force [Fr].

Tuning of the Insertion Force and Removal Force

As such some embodiments of the present invention, the insertion force [Fi] (for inserting the second mating member 200 into the coupling mechanism 300 to be coupled to the first mating member 100 by the coupling member 1000, specifically substantially oval disc shaped coupling member 1600) and the removal force [Fr] (for removing the second mating member 200 from coupling mechanism to be disengaged from the first mating member 100) are tunable as shown in FIGS. 8A-8C, as well as FIG. 8D(i). As such, some embodiments of the present invention, provide a mechanism to tune or control the insertion and removal forces (Fi, Fr) for example by changing the respective ramp angles for insertion and removal ramps 1633A, 1633B. In some such examples, the coupling member 1000 such as a substantially disc shaped coupling member 1600, one or more orientation keys 1480 are provided so the substantially disc shaped coupling member 1600 can be inserted in the desired orientation with the appropriate insertion ramp 1633A and 1633B being oriented to have the appropriate insertion and removal ramp angles as desired as shown in FIG. 8E(i), 8E(ii) and 8E(iii). This may facilitate assembly where the removal ramp angle may be different than the insertion ramp angle.

Providing Substantially Equivalent Insertion Force and Removal Force

In other words the first and second ramps 1633A, 1633B may be varied to define respective insertion and removal forces (Fi, Fr). In other examples, the first and second ramps 1633A, 1633B have substantially equivalent ramp angles defining substantially equivalent removal [Fr] and insertion forces [Fi] respectively, as shown in FIG. 8B.

Snap Force May be Varied

In some embodiments of the present invention, as shown in FIG. 8D(ii), 8E(ii) and 8E(iii), the snap force (for example the force required to snap the second mating member 200 to the first mating member 100 using the coupling member 1000, specifically the substantially oval disc shaped coupling member 1600) for example as defined by the insertion force [Fi] and/or the removal force [Fr] can be dialed in (or changed) by varying the wall thickness [T] and the snap height. In some such examples, the snap overlap [X] is defined as the overlap between the snap 1630 and the portion of the second mating member 200 that is inserted into the first mating member 100, for example for a dilator 220, the portion of dilator 220 defining the groove 226 of the dilator 220 and/or the ridge or bump 228 of the dilator hub 222, with reference to FIG. 8F(ii). In one such example, the wall thickness T is about 0.75 mm and the snap overlap X is about 0.5 mm. In another example, the wall thickness T is about 1.0 mm and the snap overlap is about 1.0 mm.

Coupling Member Remains within the Elastic Region

In some such embodiments of the present invention as shown in FIGS. 7A, 7B and additionally shown in FIGS. 7C and 7D, the substantially disc shaped coupling member 1600 of the releasable coupling mechanism 300 substantially remains in the elastic region upon deformation, for example as it flexes between the first state 1000A and the second state 1000B. In some such embodiments of the present invention, with reference again to FIGS. 7A-7D as well as FIGS. 8B-8C, wherein the insertion force [Fi] for inserting the second mating member 200 into the coupling mechanism 300 to be coupled to the first mating member 100, and the removal force [Fr] for removing the second mating member 200 from coupling mechanism 300 to be disengaged from the first mating member, are substantially uniform over multiple uses of the coupling mechanism 300. In other words, the insertion force [Fi] and the removal force [Fr] remain substantially unchanged over multiple uses. In some embodiments, the ability of coupling member 1000 (for example the substantially oval disc shaped coupling member 1600) to remain in the elastic region during deformation and flexion substantially facilitates that the insertion and removal forces (Fi, Fr) remain substantially constant or unchanged over multiple uses.

In some such examples, the substantially oval disc shaped coupling member 1600 (racetrack component or snap component) is able to flex since it is free floating within the housing 124, and the sheath hub length L is minimized since the flexing is in a radial direction. The racetrack is formed integrally or in other words has continuous geometry which facilitates reduction in stress concentrations. Additionally the snap force can be dialed in or changed or tuned with altering wall thickness T and snap overlap or snap engagement X. In some such examples, the substantially oval disc shaped coupling member 1600 comprises a polycarbonate. In additional examples, the substantially oval disc shaped coupling member 1600 may comprise a resilient material. In another example the material is ABS Acrylonitrile butadiene. In some embodiments the strain seen by the coupling member 1000 such as the substantially oval disc shaped coupling member 1600 during flexion between first and second states 100A, 100B is less than about 6%, where the coupling member 1000 would require a strain of greater than about 6% before plastic deformation occurs. Above this strain value the coupling member 1000 would be plastically deformable but the structure of the coupling member 1000 prevents this by providing elastic deformation over multiple uses. In some such example, the strain the coupling member 1000 sees is substantially dependent on the structure (for example it is based on the structure of the substantially oval disc shaped coupling member 1600 which has a substantially racetrack structure based on the geometry) which allows for a less than 6% strain value.

Figure 13B:
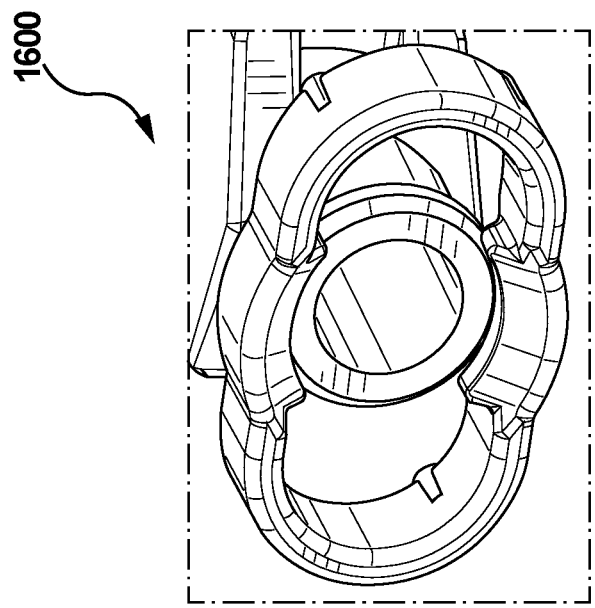
FIGS. 13A, 13B and 13E are perspective views of a coupling mechanism comprising a coupling member, in accordance with an alternative embodiment of the present invention.
Figure 13A:
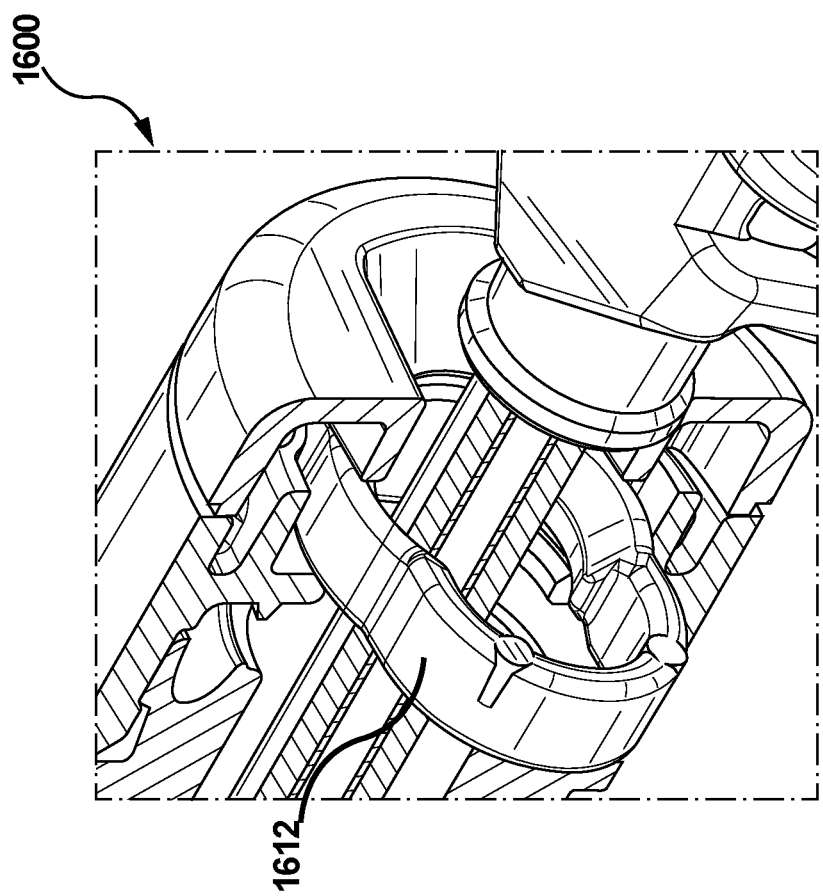
Figure 13D:
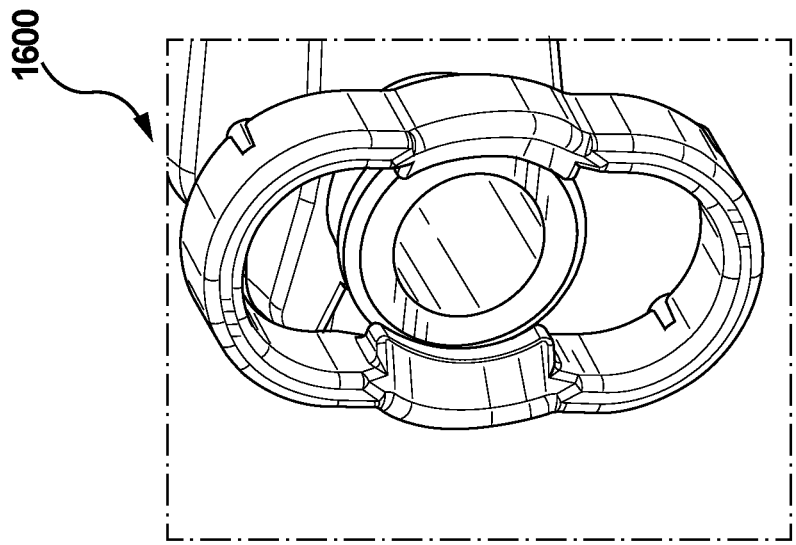
FIGS. 13C, 13D and 13F are perspective views of a coupling mechanism comprising a coupling member, in accordance with an alternative embodiment of the present invention.
Figure 13C:
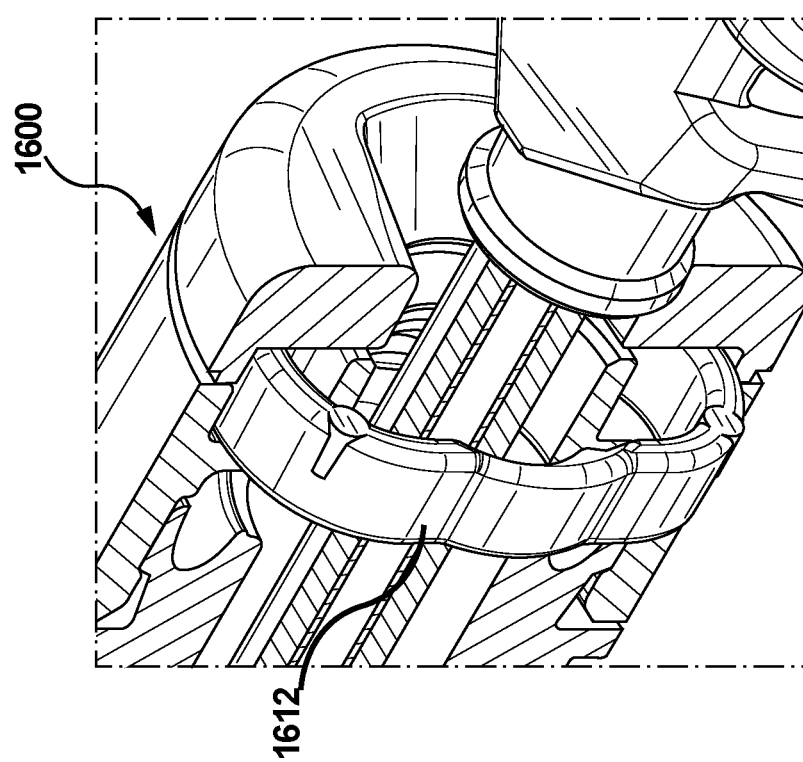
Figure 13E:
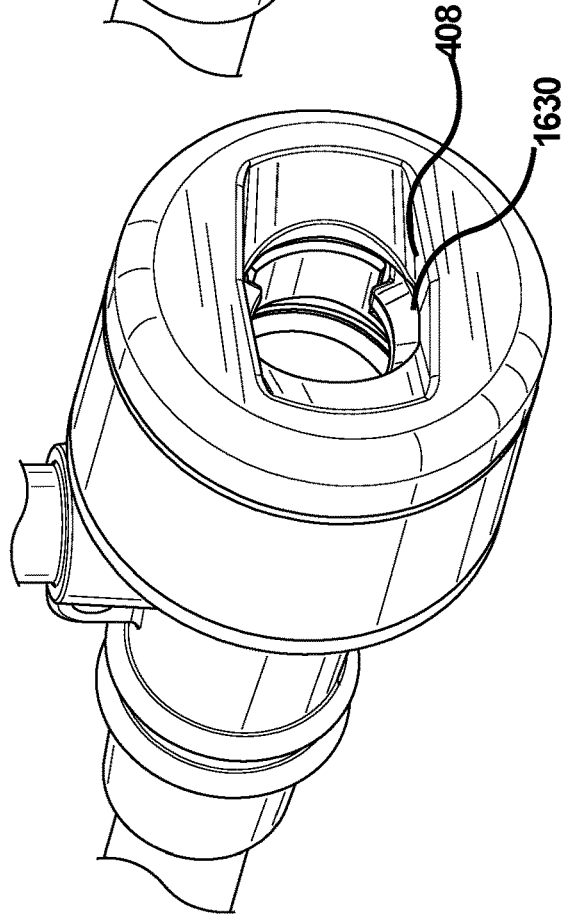
Figure 13F:
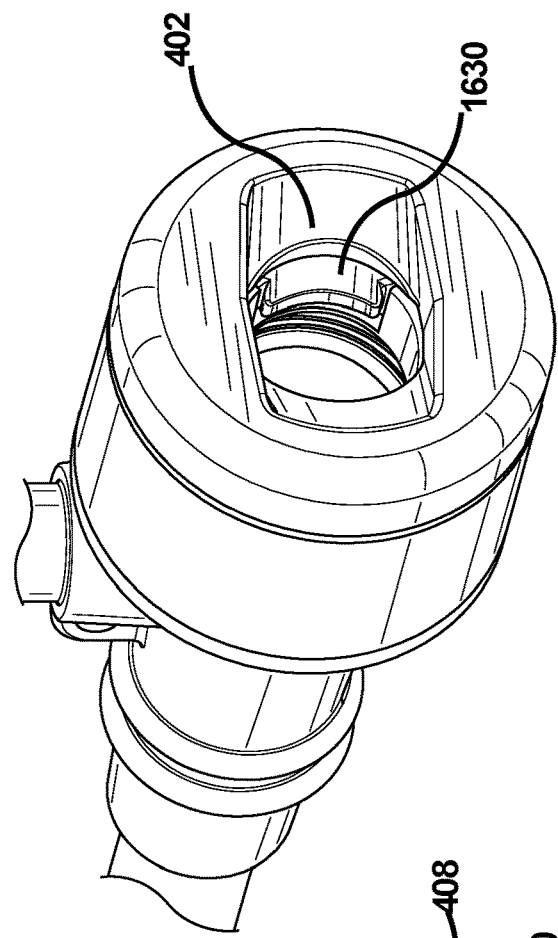

In some embodiments as shown in FIGS. 13A, 13B, 13E the substantially oval disc shaped coupling member is oriented so that the cantilever arms 1612 are oriented so that they are parallel to the flat faces 408 of the hub cap and the snaps 1630 are positioned along the flat faces. In some embodiments as shown in FIGS. 13C and 13D, 13F the substantially oval disc shaped coupling member is oriented so that the cantilever arms 1612 are oriented so that they are perpendicular to the flat faces 408 of the hub cap, so the snaps 1630 are positioned adjacent the guides 402.

In an alternative embodiment of the present invention, a coupling member 1000, specifically substantially disc shaped coupling member 1600 is provided in a first mating member 100 that comprises a steerable sheath 190 as shown in FIGS. 14A, 14B, 14C, 14D, 14E and 14F, where the substantially disc shaped coupling member 1600 is contained or retained within the housing 124 (formed by a housing base 124b and a hub cap 126) and may comprise additional component to contain the coupling member in the housing. The coupling member is substantially free floating in the housing 124, where the coupling member 1000 (substantially disc shaped coupling member 1600) is configured to couple the second mating member comprising the dilator 220 to the steerable sheath 190.

General Audible Feedback

In some embodiments of the present invention, the coupling member 1000, such as coupling members (straight cantilever coupling member 1200), (u-shaped coupling member 1300) and (substantially oval disc shaped coupling member 1600), configured to generate an audible feedback upon movement between the first state 1000A and second state 1000B, with reference to FIGS. 2A(ii), 2B(ii), 3B,3C, 4B. 4C, 5B,5C In some such examples the coupling member 1000 (specifically each of the straight cantilever coupling member 1200, u-shaped coupling member 13000 and substantially oval disc shaped coupling member 1600), interact with the second mating member 200 upon insertion into the first mating member 100 to generate audible feedback. In some such example, the respective snaps 1230, 1330 and 16300 of the respective coupling members interact with a portion of the second mating member 200 (such as groove 226) upon once the coupling member returns from its second state 1000B to the first state 1000A generating an audible click indicating insertion and coupling of the second mating member 200 to the first mating member 100. Similarly in some such examples, the respective snaps 1230, 1330 and 16300 of the respective coupling members interact with a portion of the second mating member 200 (such as ridge or bump 228) upon once the coupling member returns from its second state 1000B to the first state 1000A upon removal of the second mating member 200 from the first mating member 100 to generate an audible click indicating removal and decoupling of the second mating member 200 from the first mating member 100.

Alternate Claim for the Racetrack Embodiment

In some embodiments of the present invention, specifically with reference to FIGS. 6A(i)-6F(iv), 7A-7D, 8A-8F(iii), a releasable coupling system 500 is provided comprising a first mating member 100 defining an opening 112 for receiving a second mating member 200 there-through. In some such examples the second mating member 200 has a first diameter (for example of the portion of the dilator 220 defining the groove 226) defining an effective diameter that is smaller than the opening 112 enabling it to be advanced into the first mating member 100 through the opening 112. The system 500 further comprises a means for increasing the effective diameter of the second mating member 200, the means comprising a coupling member 1000 (specifically the substantially oval disc shaped coupling member 1600) positioned/located within the first mating member 100. Upon insertion of the second mating member 200 into the first mating member 100 through the opening 112 thereof, the coupling member 1000 (specifically the substantially oval disc shaped coupling member 1600) is coupled to the second mating member 200, thereby modifying [increasing] the effective diameter of the second mating member 200 (for example at the groove 226) such that the effective diameter of the second mating member 200 is larger than the opening 112 of the first mating device 100 preventing it from exiting therefrom/moving translationally therein. Additionally the effective diameter of the second mating member 200 is larger than a distal opening in the housing 124 of the first mating member 100. Thus, the coupling member 1000 when functionally coupled to the second mating member prevents or blocks the movement of dilator hub 122 out of the sheath hub 122 in the absence of force, thereby preventing the dilator hub from exiting by interacting with both the distal face and the proximal inner faces of the housing 124.

Alternatives

In other words, the embodiments shown in FIGS. 1A-1D, specifically with reference to FIG. 1B, the flexible coupling mechanism 300 additionally a flexible locking member or component 1000 that is seated within the first handle housing such as the sheath housing 124 for releasably coupling the second handle portion 210 to the first handle portion 110. The flexible locking member or component has a first configuration 1000A which can also be the locking configuration as shown in FIG. 7A, and FIG. 6C and a second non-locking configuration 1000B (FIG. 7B). Upon initial advancement of the second handle portion 210 into the first handle portion, the flexible locking member or component 1000 is moveable outwards from its first locking configuration 1000A into its second non-locking configuration 1000B out of the path of the second handle wider portion such as ridge or bump 228 upon interaction therewith, and upon further advancement of the second handle portion 210 into the first handle portion 110, the flexible locking member or component 1000 is moveable inwards into the second handle groove portion 226 from its second non-locking configuration into its first locking configuration as shown in FIG. 7A, in order to releasably couple the dilator hub 222 to the sheath hub 122, whereby the flexible locking member or component 1000 is moveable into its second non-locking configuration upon exertion of force as the dilator hub 222 is pulled to enable disengagement of the releasable locking mechanism. In some examples the flexible locking member or component has snaps 132.

Rotational Locking Mechanism

In accordance with some embodiments of the present invention a coupling mechanism is provided that allows two devices to be coupled together so they can be maneuvered or manipulated together thereby forming a rotational locking assembly or system that comprises the two devices. In some such examples, the coupling mechanism comprises a locking mechanism to allow one or more of rotational and/or translational locking of the two devices. In addition to coupling mechanism 300 that function as translational locking mechanisms as described herein above, some embodiments of the present invention additionally provide for rotational locking mechanism 400 in addition to the releasable coupling mechanism 300. Some embodiments may include one or more of the releasable coupling mechanism and rotational locking mechanism.

In some such examples, with reference now to FIGS. 9A(i), 9A(ii), 9A(iii) and 9A(iv), the coupling mechanism comprises a rotational locking mechanism 400 comprising guides and/or corresponding co-operating features (such as guides 402, 404 and 406 within or along the two devices for enabling coupling of a sheath 100 and a dilator 200) to allow the two devices to be maneuvered or manipulated together. The present invention overcomes problems with prior art systems in terms of meeting the need in the art for: a) allowing the user to have the ability to rotate the connected devices using either the sheath hub or dilator hub or handle, and additionally b) to allow the dilator to be oriented in the same direction as the curve of the sheath (for example in embodiments where the dilator is stiff).

In one embodiment of the present invention, a rotational key mechanism or rotational locking mechanism 400 has been added to the first and second mating members 100, 200 dilator and sheath hubs 104, 204, as discussed above and as shown in FIGS. 1A and 1C, allowing them to be maneuvered together such as rotated or torqued together. The coupling mechanism comprising a rotational locking mechanism 400 as shown, ensures proper alignment (for example between the first and second mating members 100,200 such as the sheath and dilator hubs 122, 222 and thus the dilator and sheath 120, 220) as shown in FIGS. 9A(i) and 9A(iv) and thus provides the assembly of the sheath 120 and dilator 220 to be maneuvered together and hence provides the assembly with the ability to transmit torque.

In the particular example shown in FIGS. 1A and 1C, the sheath hub 122 comprises guides 402 which are sides that funnel in towards the valve In one such embodiment the housing 124 of the first mating member 100, specifically the sheath 120 comprises one or more guides 402 comprising angles or tapered guides or surfaces 406 as shown in FIG. 9A(iii). The first mating member additionally comprises one or more keying surfaces or features 404 such as adjacent flat surfaces 408 comprising keying and torque transfer surfaces. In some such embodiments keying and torque transfer is provided on or using the flat faces or surfaces 408. In some such examples, one or more of the guides 402 and the keying features 404 define a first corresponding engagement feature 460 of the locking mechanism 400. The locking mechanism further comprises corresponding guide portions 202 on the dilator hub 222 that are angled that interact with the guides 402 to guide the dilator 222 into the sheath hub 122. Additionally the dilator hub 222 comprises one or more corresponding keying surfaces 204 that correspond to the keying surfaces or features 404 of the sheath. In some such embodiments, one or more of the keying surfaces 204 and guide portions 202 of the dilator 220 provide a second corresponding engagement feature 260 for the rotational locking mechanism 400 to enable co-operative coupling for example to enable rotational locking. The sheath hub further comprises flat faces 404 to provide keying and torque transfer. In some such embodiments the user can pivot the dilator hub 220 for example 3-9 O-clock to loosen the snap. In some such embodiments the force to disengage the rotational locking mechanism 400 is greater than about 10 Newtons. In some embodiments it is about 15 Newtons.

In some such embodiments, due to the angled face 209 on the front of the dilator, when the dilator is torqued the corner edges touch. In some examples, the corresponding flat faces may not mate when torqued. The torque being applied on the angle generates an unsnapping force for the rotational locking mechanism. When the torque is sufficient to generate enough unsnapping force, then the rotational lock disengages and the dilator 220 unsnaps from the sheath 120.

Figure 9C:
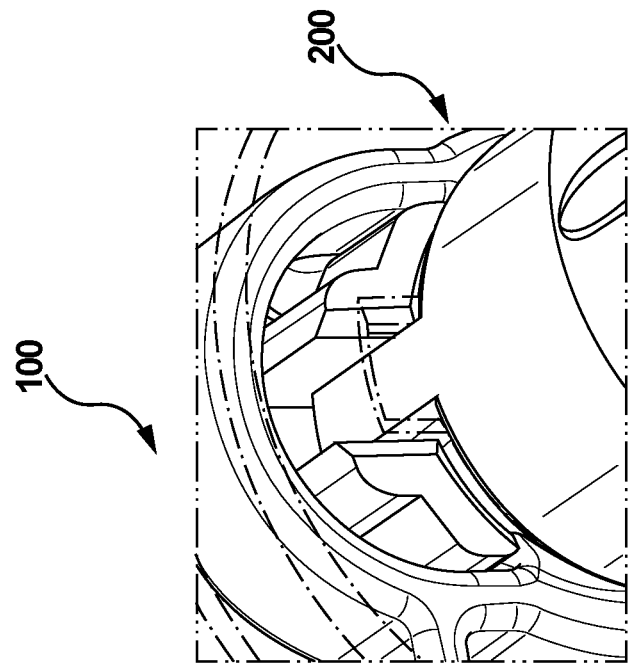
FIGS. 9B and 9C are perspective views of components of a rotational locking assembly comprising a first mating member and a second mating member and engagement there-between, in accordance with an alternative embodiment of the present invention.
Figure 9B:
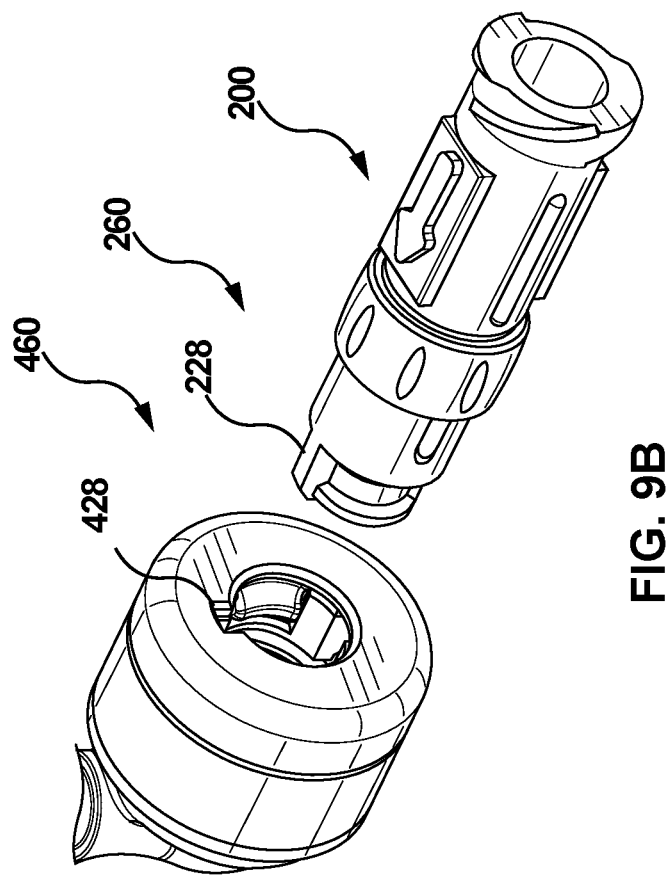

In an additional embodiment of the present invention as shown in FIGS. 9B, and 9C, a rotational locking mechanism is provided a first corresponding engagement feature on the first mating member 100 comprising a key 428 for example formed in a portion of the housing 124 such as the hub cap 126) and a second corresponding engagement feature comprising a rib 228 on the second mating member 200.

Figure 10C:
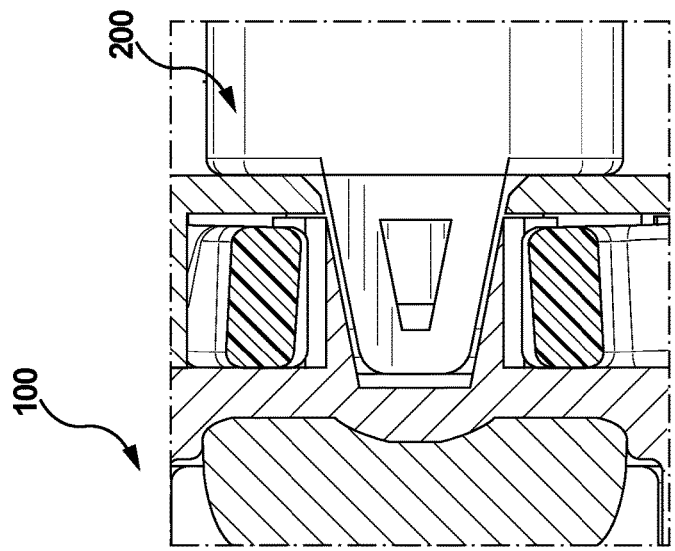
FIG. 10C is a side cross-sectional view of the rotational locking assembly of FIG. 10A, in accordance with an alternative embodiment of the present invention.
Figure 10B:
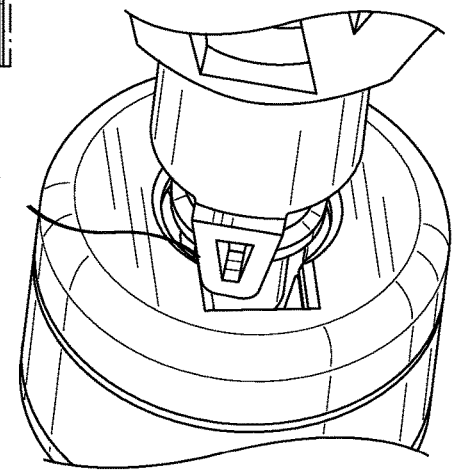
FIGS. 10A and 10B are perspective views of components of a rotational locking assembly comprising a first mating member and a second mating member and engagement there-between, in accordance with an alternative embodiment of the present invention.
Figure 10A:
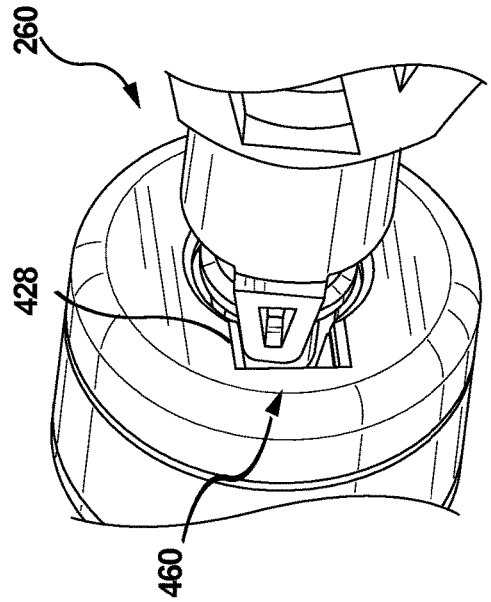

In an additional embodiment of the present invention as shown in FIGS. 10A, 10B and 10C, a rotational locking mechanism is provided a first corresponding engagement feature on the first mating member 100 comprising a key 428 (for example formed in portion of the housing 124 such as the cover or hub cap 126) and a second corresponding engagement feature comprising a rib 228 on the second mating member 200. Additionally chamfers are provided on the key 428 and radii or curved edges on the rib 228 to facilitate guiding the second mating member 200 the dilator 220 into the first mating member 100, i.e. the sheath 120. In some such examples, the key 428 comprises a slot in the cover or hub cap 126 and the slot in the hub cap 126 and the rib 228 have corresponding matching angles which may facilitate surface contact.

Figure 11A:
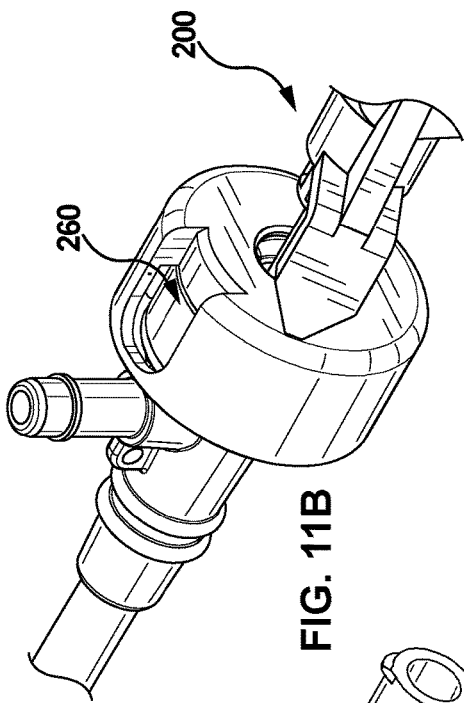
FIGS. 11A and 11B are perspective views of components of a rotational locking assembly comprising a first mating member and a second mating member and engagement there-between, in accordance with an alternative embodiment of the present invention.
Figure 11B:
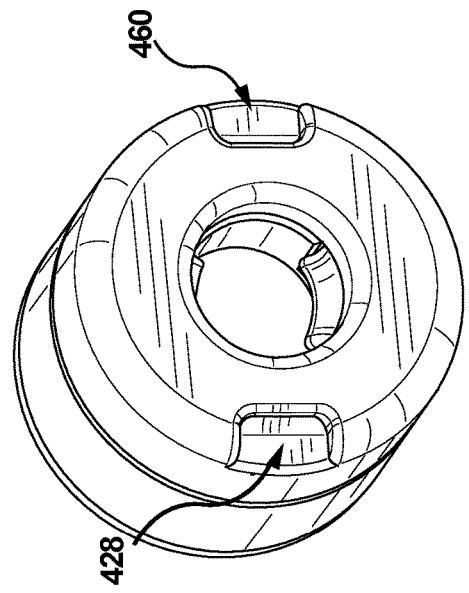
Figure 12A:
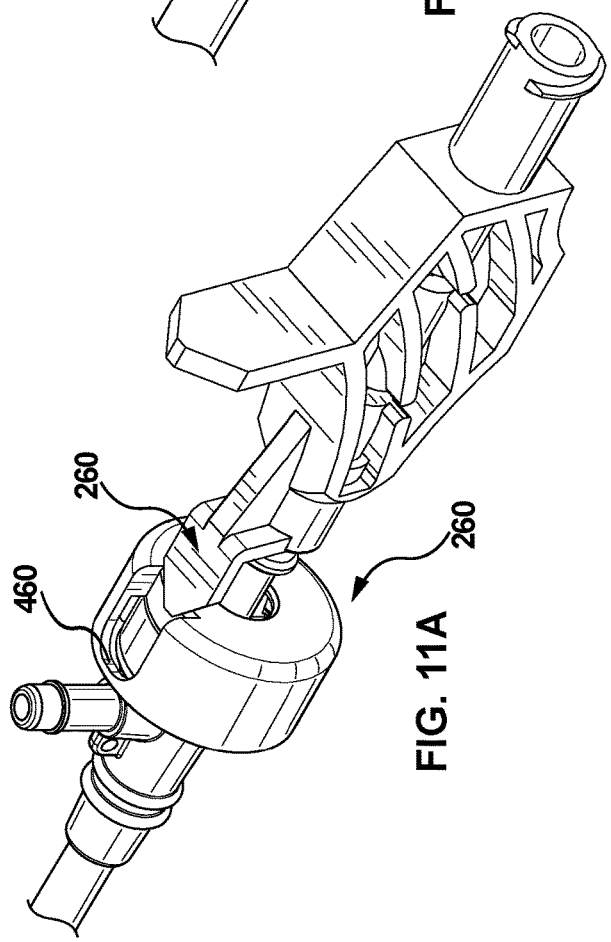
FIGS. 12A and 12B are perspective views of components of a rotational locking assembly comprising a first mating member and a second mating member and engagement there-between, in accordance with an alternative embodiment of the present invention.
Figure 12B:
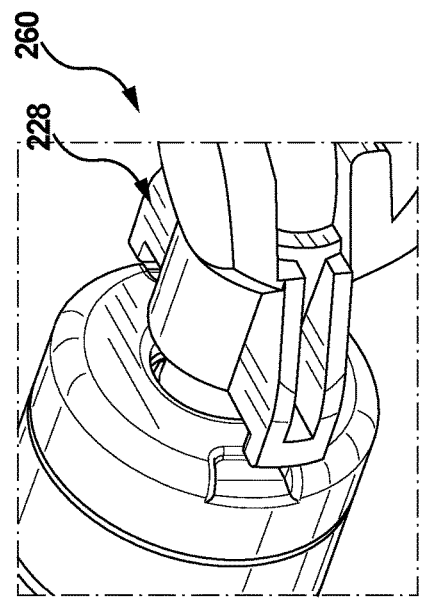

In an additional embodiment of the present invention as shown in FIGS. 11A, and 11B, and 12A and 12B a rotational locking mechanism is provided a first corresponding engagement feature on the first mating member 100 comprising a key 428 (for example formed in a portion of the housing 124 such as the hub cap 126) [which in FIGS. 11A, 11B comprises a slot in the hub cap 126, and in FIGS. 12A, 12B comprises at least two grooves]. The rotational locking mechanism 400 further comprises a second corresponding engagement feature comprising a rib 228 which may be angled on the second mating member 200. In FIGS. 12A, 12B, two rib sections 228 are provided that correspond to the two grooves 428.

In some such embodiments a rotational locking mechanism is provided comprising, a first corresponding engagement feature on a first mating member, a second corresponding engagement feature on a second mating member, wherein the first and second corresponding features enable rotational locking. In some such examples, the rotational the first corresponding feature comprises one or more guides. In one such example, the one or more guides comprise a funnel. In some such embodiments, the first corresponding feature comprises a keying feature. In some such embodiments the keying feature comprises a substantially flat face. In some such embodiments, the second corresponding feature comprises one or more guide portions that are configured to mate with the one or more guides of the first corresponding feature of the sheath. In some such embodiments, the second corresponding feature comprises keying surfaces that correspond to the keying features of the first corresponding feature.

FIGS. 2-111 additionally show additional embodiments of coupling mechanisms in accordance with various embodiments of the present invention.

Various Embodiments of Coupling Members

In some embodiments of the present invention, the coupling member comprises a flexible coupling member. In some embodiments, the coupling member comprises a resilient coupling member. In still some examples, the coupling member comprises an elastic coupling member that is elastically deformable.

Cantilever Coupling Member

In some embodiments, the coupling member comprises at least one cantilever.

Straight Cantilever

In some embodiments, the coupling member comprises at least one straight or simple cantilever. In some such examples, the at least one straight or simple cantilever is coupled to [a housing of the first mating member. In some embodiments, the coupling member comprises two or more straight or (simple) cantilevers.

U-Shaped Cantilever

In some embodiments, the coupling member comprises at least one u-shaped cantilever. In some such embodiments, the at least one u-shaped cantilever comprises at an elastic u-shaped cantilever. In one example, the coupling member comprises a pair u-shaped cantilevers. In a specific instance, the coupling member comprises a pair of inverted u-shaped cantilevers.

Substantially Disc-Shaped Cantilever

In another embodiment, the coupling member comprises a substantially disc shaped cantilever or a substantially annular cantilever or substantially annular coupling member. In one example the coupling member comprises a substantially disc shaped configuration. In one example the coupling member comprises a substantially oval disc shaped configuration. In one embodiment, the coupling member substantially comprises a snap ring or band (or substantially annular snap ring or band). In a specific example of this, the coupling member comprises a substantially oval snap ring or band.

General Audible Feedback

In some embodiments, the coupling member is configured to generate an audible feedback upon movement between its first state and second state. In some such embodiments, the coupling member interacts with the second mating member upon insertion into the first mating member to generate audible feedback. In some embodiments, the coupling member interacts with the second mating member upon once the coupling member returns from its second state to the first state generating an audible click.

Alternatives

In some embodiments, a locking mechanism is provided comprising a locking (member or component) held (seated/positioned) within a locking device for releasably coupling a second device thereto, where the second device is receivable by the locking device, wherein the locking (member or component) has a first state (or configuration) and a second state (or configuration), and wherein the locking member is moveable from its first state into its second state upon insertion of the second device into the locking device to allow passage of the second device there-through and is moveable thereafter into its first state to couple the second device to the locking device.

In some embodiments, a releasable locking assembly is provided comprising a locking device, a locking (member or component) held (seated/positioned) within the locking device for releasably coupling a second device that is receivable by the locking device, to the locking device, wherein the locking component has a first state (or configuration) and a second state (or configuration), wherein the locking component is moveable from a first state into a second state upon insertion of the second device into the locking device to allow passage of the second device there-through and the locking component is moveable thereafter into its first state to couple the second device to the locking device.

In some embodiments, a locking system is provided comprising a locking device, a locking (member or component) held (seated/positioned) within the locking device, and A coupling member held within the first mating member, and a second device that is receivable by locking device to be releasably secured thereto by the locking member, wherein the locking component is moveable from its first state into its second state upon insertion of the second device into the locking device to allow passage of the second device there-through and the locking component is moveable thereafter into its first state to couple the second device to the locking device.

Alternatives

In some embodiments, a releasable coupling mechanism is provided comprising A housing defining a primary mating member [defining an opening] for receiving a secondary mating member to be coupled thereto, an elastically deformable a retaining component [or member] seated [or positioned] within the housing, for releasably coupling the secondary mating member to the housing upon insertion thereof into the housing, wherein the elastically deformable retaining component has a first engaging configuration and a second non-engaging configuration, wherein the elastically deformable retaining component is moveable into its second non-engaging configuration upon insertion of the secondary mating member into the housing to enable the secondary mating member to advance into the housing and is moveable thereafter into its first engaging configuration to couple the secondary mating member to the primary mating member preventing [the secondary mating member to be detachable therefrom, preventing disengagement thereof in the absence of force to prevent the secondary mating member to be removable from the opening thereof].

In some such embodiments retaining component comprises a deflectable member and is deflectable into its second non-engaging configuration upon insertion of the secondary mating member and is capable of returning to its original first engaging configuration thereafter. In some such embodiments, the retaining component comprises a flexible retaining component. In some examples of the releasable coupling mechanism, the retaining component comprises an elastic retaining component. In some examples, retaining component comprises an elastically deformable retaining component.

In some embodiments, the retaining component is contained within the housing so it is substantially enclosed by the housing. In some examples, the housing comprises a cap and a cover, defining a cavity or space therein, and the retaining component is seated or positioned within the cavity or space defined by the housing. In some examples, the retaining component is coupled to the housing. In some examples, the retaining component is attached to the housing. In some examples, the retaining component is attached to the housing at least at an end or point thereof. In some examples, the retaining component is formed integrally with the housing. In some examples, the retaining component comprises at least one retaining arm or member or in other words one or more retaining arms or members.

In some examples, the at least one retaining arm [or member], wherein the one or more retaining arms or [members] terminate in one or more snaps. In some examples, the at least one retaining arm [or member], wherein the one or more retaining arms or [members] comprises one or more cantilevers. In some examples, the one or more cantilevers comprise a straight cantilever. In In some examples, he one or more cantilevers comprise a u-shaped cantilever.

In some embodiments of the u-shaped cantilever, the u-shaped cantilever in its first engaging configuration comprises a substantially u-shaped configuration and wherein the retaining component in its second non-engaging configuration comprises a substantially compressed u-shaped configuration, Wherein the elastically deformable retaining component is moveable into its second non-engaging configuration comprising the substantially compressed u-shaped configuration upon insertion of the secondary mating member into the housing to enable the secondary mating member to advance into the housing and is moveable thereafter into its first engaging configuration comprising the substantially u-shaped configuration to couple the secondary mating member to the primary mating member.

In some embodiments, wherein the u-shaped cantilever in its first engaging configuration comprises a substantially u-shaped configuration and wherein the retaining component in its second non-engaging configuration comprises a substantially expanded shaped configuration, wherein the elastically deformable retaining component is moveable into its second non-engaging configuration comprising the substantially expanded u-shaped configuration upon insertion of the secondary mating member into the housing to enable the secondary mating member to advance into the housing and is moveable thereafter into its first engaging configuration comprising the substantially u-shaped configuration to couple the secondary mating member to the primary mating member.

In some embodiments, the retaining component is retained [or held loosely] within the housing to be constrained therein or restrained. In other words it is substantially not coupled thereto or affixed thereto/not rigidly fastened or securely attached. In some such examples, the retaining component is free floating within the housing, ie. Some embodiments provide comprises a free floating retaining component that is free floating within the housing. In some such examples, the retaining component is moveable in a direction that is in a plane that is perpendicular to the direction of advancement of secondary mating member into the housing for insertion therein.

In some embodiments, the retaining component is moveable in a direction that is in a plane that is perpendicular to the direction of advancement of secondary mating member into the housing for insertion therein. In some such examples, the elastically deformable retaining component comprises a substantially disc shaped structure. In some such examples, the elastically deformable retaining component comprises a substantially oval disc shaped structure. In some embodiments, the retaining component is moveable in a direction that is in a plane that is in plane with the direction of advancement of secondary mating member into the housing for insertion therein. In some embodiments, the retaining component is moveable in a plane that is perpendicular with the direction of advancement of secondary mating member into the housing for insertion therein. In some such embodiments, the retaining component is moveable [radially] in a radial direction.

In some embodiments, the retaining component is biased in its first engaging configuration, wherein upon insertion of the secondary mating member into the housing [the secondary mating member exerts an outward radial force against the retaining component whereby] the retaining component is moveable into its second engaging configuration to enable the secondary mating member to advance into the housing, In some embodiments, the retaining component is independently moveable with respect to the housing. In some embodiments, the housing comprises a cap in other words housing base portion and a cover or hub cap, defining a cavity [or space] therein for holding the retaining component therein free from engagement therein.

In some embodiments a releasable coupling mechanism is provided comprising, A coupling comprising a primary receiving hub [defining an opening] for receiving an advancing secondary hub for insertion therein, and an independently moveable coupling/gripping component seated within a cavity of the primary hub and enclosed therein, the independently moveable gripping component having an engaging configuration and a non-engaging configuration, wherein upon insertion of the secondary hub into the primary hub, the independently moveable gripping component is initially moveable into its non-engaging configuration to enable advancement of [an engaging portion of] the secondary hub, and is moveable thereafter into its engaging configuration for gripping/grabbing the portion of the secondary hub to enable coupling thereby preventing disengagement thereof [preventing the secondary hub from being removed from the opening in the absence of force], and wherein upon retraction of the secondary hub from the primary hub, the independently moveable gripping component is moveable into its non-engaging configuration to enable disengagement thereof.

In one example, the independently moveable gripping component comprises a flexible gripping component. In one example, the independently movable gripping component comprises a resilient gripping component. In one example, the independently moveable gripping component is radially moveable.

In one broad aspect, embodiments of the present invention comprise a releasable locking mechanism for releasably coupling two medical devices, the releasable locking mechanism comprising, a first handle portion defining a housing comprising an opening for receiving a part of a second handle portion therein, the second handle portion comprising a second handle wider portion and a second handle groove portion, a flexible locking member or component that is seated within the first handle housing for releasably coupling the second handle portion to the first handle portion, the flexible locking member or component having a first locking configuration and a second non-locking configuration, Wherein upon initial advancement of the second handle portion into the first handle portion, the flexible locking member or component is moveable outwards from its first locking configuration into its second non-locking configuration out of the path of the second handle wider portion upon interaction therewith, and upon further advancement of the second handle portion into the first handle portion, the flexible locking member or component is moveable inwards into the second handle groove portion from its second non-locking configuration into its first locking configuration, in order to releasably couple the dilator hub to the sheath hub, whereby the flexible locking member or component is moveable into its second non-locking configuration upon exertion of force as the dilator hub is pulled to enable disengagement of the releasable locking mechanism.

In some examples, the the flexible locking member or component comprises a resilient locking member or component. In a further broad aspect, embodiments of the present invention comprise a releasable locking mechanism for releasably coupling two medical devices, the releasable locking mechanism comprising, a first handle portion defining a housing comprising an opening for receiving a part of a second handle portion therein, the second handle portion comprising a second handle wider portion and a second handle groove portion, a moveable locking member or component that is seated within the first handle housing for releasably coupling the second handle portion to the first handle portion, the moveable locking member or component having a first locking configuration and a second non-locking configuration, wherein upon initial advancement of the second handle portion into the first handle portion, the moveable locking member or component is moveable outwards from its first locking configuration into its second non-locking configuration out of the path of the second handle wider portion upon interaction therewith, and upon further advancement of the second handle portion into the first handle portion, the moveable locking member or component is moveable inwards into the second handle groove portion from its second non-locking configuration into its first locking configuration, in order to releasably couple the dilator hub to the sheath hub, whereby the moveable locking member or component is moveable into its second non-locking configuration upon exertion of force as the dilator hub is pulled to enable disengagement of the releasable locking mechanism.

In still further embodiments, a releasable locking mechanism is provided for releasably coupling two devices, the releasable locking mechanism comprising, A first receiving device defining a housing, the housing defining an opening for receiving an second insertion device there-through, the second insertion device having a first diameter that is a smaller effective diameter than the opening enabling it to be advanced into the receiving first device, a means for increasing the effective diameter of the second device, the means comprising a moveable and/or flexible locking member or component, Wherein upon insertion of the second device into the first device through the opening thereof, the moveable and/or flexible locking component is moveable to around the second insertion device creating an interference fit/or interacts with to be coupled to the incoming insertion second device that is inserted there-through, thereby creating a larger effective diameter of the second device, thereby creating an effective diameter of the second device, that is larger than the opening of the first device, thereby preventing it from exiting therefrom. Preventing or blocking the movement of dilator hub out of the sheath hub in the absence of force, thereby preventing the dilator hub from exiting.

In some embodiments, a releasable locking mechanism is provided for releasably coupling two devices, the releasable locking mechanism comprising, A sheath hub defining an opening for receiving a dilator hub there-through, a means for increasing an effective diameter of the dilator hub comprising a moveable and/or flexible locking member or component, wherein the dilator hub has a smaller effective diameter than the opening going into the to enable advancement into the sheath hub and once positioned inside the sheath hub, and wherein once the dilator hub is advanced into the sheath hub, the moveable and/or flexible locking component moves around the dilator hub creates an interference fit/or interacts with the incoming dilator hub preventing it from exiting from the opening, thereby creating a larger effective diameter on the dilator hub that is larger than the opening within the sheath hub, thereby preventing/blocking the movement of dilator hub out of the sheath hub in the absence of force, preventing the dilator hub from exiting.

As a further overview, some embodiments of the present invention provide a novel coupling for two devices. This may be advantageous in scenarios such as when a dilator snaps into a sheath hub to connect the two devices. This is generally done by the user on the proximal end which is the user interface. By connecting the two devices proximally, it ensures the distal portions remain fixed in the correct position while the user guides the sheath and dilator in the patient anatomy.

Inventors of the present invention have invented coupling mechanisms that attempt to overcome problems associated with prior art mechanism. Problems associated with existing devices are that they have snaps which degrade with use, have insufficient retention force, provide insufficient tactile feedback, or generate debris. These snaps typically embody a rigid ring or bump on the dilator hub that must press into a mating feature on the sheath hub.

Additionally there is a need in the art for the user needs to have the ability to rotate the connected devices using either the sheath hub or dilator handle, and/or additionally to allow a dilator (such as a stiff dilator) to be oriented in the same direction as the curve of the sheath.

Inventors of the present invention have developed a snap member with inherent flexibility, which allows the snap to be/become substantially robust. Additionally a coupling mechanisms is provided that provides a rotational key, for example that has been added to the dilator and sheath hubs. In some such embodiments, this ensures proper alignment and the ability to transmit torque. Thus some embodiments of the present invention, provide a coupling mechanism that provide a) a snap mechanism with inherent flexibility, and/or b) providing mechanical engagement between the dilator and sheath hubs which can transfer torque and which provides for consistent alignment.

In some embodiments, the direction of the sheath curve is indicated by the side port on the sheath hub and is controlled by rotating the sheath hub.

In one broad aspect, embodiments of the present invention comprise a releasable locking mechanism for releasably coupling two medical devices, the releasable locking mechanism comprising: a first handle portion defining a housing comprising an opening for receiving a part of a second handle portion therein, the second handle portion comprising a second handle wider portion and a second handle groove portion; a flexible locking member or component that is seated within the first handle housing for releasably coupling the second handle portion to the first handle portion; the flexible locking member or component having a first locking configuration and a second non-locking configuration; Wherein upon initial advancement of the second handle portion into the first handle portion, the flexible locking member or component is moveable outwards from its first locking configuration into its second non-locking configuration out of the path of the second handle wider portion upon interaction therewith, and upon further advancement of the second handle portion into the first handle portion, the flexible locking member or component is moveable inwards into the second handle groove portion from its second non-locking configuration into its first locking configuration, in order to releasably couple the dilator hub to the sheath hub, whereby the flexible locking member or component is moveable into its second non-locking configuration upon exertion of force as the dilator hub is pulled to enable disengagement of the releasable locking mechanism.

In a further broad aspect, embodiments of the present invention comprise a releasable locking mechanism for releasably coupling two medical devices, the releasable locking mechanism comprising: a first handle portion defining a housing comprising an opening for receiving a part of a second handle portion therein, the second handle portion comprising a second handle wider portion and a second handle groove portion; a moveable locking member or component that is seated within the first handle housing for releasably coupling the second handle portion to the first handle portion; the moveable locking member or component having a first locking configuration and a second non-locking configuration; Wherein upon initial advancement of the second handle portion into the first handle portion, the moveable locking member or component is moveable outwards from its first locking configuration into its second non-locking configuration out of the path of the second handle wider portion upon interaction therewith, and upon further advancement of the second handle portion into the first handle portion, the moveable locking member or component is moveable inwards into the second handle groove portion from its second non-locking configuration into its first locking configuration, in order to releasably couple the dilator hub to the sheath hub, whereby the moveable locking member or component is moveable into its second non-locking configuration upon exertion of force as the dilator hub is pulled to enable disengagement of the releasable locking mechanism.

As a feature of this broad aspect, the means for increasing the effective diameter of the dilator hub comprises a moveable and/or flexible locking member or component, wherein the dilator hub has a smaller effective diameter going into the sheath hub and once positioned inside the sheath hub the moveable and/or flexible locking component moves around the dilator hub creates an interference fit/or interacts with the incoming dilator hub preventing it from exiting, by creating a larger effective diameter on the dilator hub, where the effective diameter of the dilator hub is larger than the opening within the sheath hub preventing/blocking the movement of dilator hub out of the sheath hub in the absence of force, thereby preventing the dilator hub from exiting.

The embodiment(s) of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A releasable coupling mechanism comprising:
a housing defining a primary mating member defining an opening for receiving a secondary mating member to be coupled thereto; and
an elastically deformable retaining component comprises one or more resilient u-shaped cantilever terminating in a snap having a first ramp defining an insertion force and a second ramp defining a removal force, wherein the first ramp and the second ramp include angles that create a component of force that compresses the u-shaped cantilever, wherein the insertion force and the removal force are equivalent, the elastically deformable retaining component being positioned within the housing, for releasably coupling the secondary mating member to the housing upon insertion thereof into the housing;
wherein the elastically deformable retaining component has a first engaging configuration and a second non-engaging configuration, wherein the elastically deformable retaining component is moveable into its second non-engaging configuration upon insertion of the secondary mating member into the housing to enable the secondary mating member to advance into the housing and is moveable thereafter into its first engaging configuration to couple the secondary mating member to the primary mating member preventing the secondary mating member to be detachable therefrom, preventing disengagement thereof in the absence of force to prevent the secondary mating member to be removable from the opening thereof.

2. The releasable coupling mechanism of claim 1, wherein the retaining component comprises a deflectable member and is deflectable into its second non-engaging configuration upon insertion of the secondary mating member and is capable of returning to its original first engaging configuration thereafter.

3. The releasable coupling mechanism of claim 2, wherein the retaining component comprises a flexible retaining component.

4. The releasable coupling mechanism of claim 2, wherein the retaining component comprises an elastic retaining component.

5. The releasable coupling mechanism of claim 4, wherein the retaining component comprises an elastically deformable retaining component.

6. The releasable coupling mechanism of claim 5, wherein the retaining component is contained within the housing.

7. The releasable coupling mechanism of claim 6, wherein the housing comprises a cap and a cover, defining a cavity therein, wherein the retaining component is seated within the cavity defined by the housing.

8. The releasable coupling mechanism of claim 6, wherein the retaining component is coupled to the housing.

9. The releasable coupling mechanism of claim 8, wherein the retaining component is attached to the housing.

10. The releasable coupling mechanism of claim 9, wherein the retaining component is attached to the housing at least at an end thereof.

11. The releasable coupling mechanism of claim 9, wherein the retaining component is formed integrally with the housing.

12. The releasable coupling mechanism of claim 9, wherein the retaining component comprises one or more retaining arms.

13. The releasable coupling mechanism of claim 1, wherein the one or more u-shaped cantilever in its first engaging configuration comprises a substantially u-shaped configuration and wherein the retaining component in its second non-engaging configuration comprises a substantially compressed shaped configuration; and wherein the elastically deformable retaining component is moveable into its second non-engaging configuration comprising the substantially compressed u-shaped configuration upon insertion of the secondary mating member into the housing to enable the secondary mating member to advance into the housing and is moveable thereafter into its first engaging configuration comprising the substantially u-shaped configuration to couple the secondary mating member to the primary mating member.

14. The releasable coupling mechanism of claim 1, wherein the one or more u-shaped cantilever in its first engaging configuration comprises a substantially u-shaped configuration and wherein the retaining component in its second non-engaging configuration comprises a substantially expanded shaped configuration;

wherein the elastically deformable retaining component is moveable into its second non-engaging configuration comprising the substantially expanded u-shaped configuration upon insertion of the secondary mating member into the housing to enable the secondary mating member to advance into the housing and is moveable thereafter into its first engaging configuration comprising the substantially u-shaped configuration to couple the secondary mating member to the primary mating member.

15. The releasable coupling mechanism of claim 1, wherein the retaining component is moveable in a direction that is in a plane that is perpendicular to the direction of advancement of secondary mating member into the housing for insertion therein.

16. The releasable coupling mechanism of claim 1, wherein the retaining component is moveable in a direction that is in a plane that is in plane with the direction of advancement of secondary mating member into the housing for insertion therein.

17. The releasable coupling mechanism of claim 1, wherein the retaining component is moveable in a plane that is perpendicular with the direction of advancement of secondary mating member into the housing for insertion therein.

18. The releasable coupling mechanism of claim 1, wherein the retaining component is moveable in a radial direction.

19. The releasable coupling mechanism of claim 1, wherein the retaining component is biased in its first engaging configuration, wherein upon insertion of the secondary mating member into the housing the secondary mating member exerts an outward radial force against the retaining component whereby the retaining component is moveable into its second engaging configuration to enable the secondary mating member to advance into the housing.

20. The releasable coupling mechanism of claim 1, wherein the retaining component is independently moveable with respect to the housing.

21. A releasable coupling mechanism comprising:
a housing defining a primary mating member defining an opening for receiving a secondary mating member to be coupled thereto; and
an elastically deformable retaining component comprises one or more resilient u-shaped cantilever terminating in a snap having a first ramp defining an insertion force and a second ramp defining a removal force, wherein the insertion force and the removal force are different, wherein upon removal of the second mating member from the primary mating member the removal force creates a moment on the u-shaped cantilever, the elastically deformable retaining component being positioned within the housing, for releasably coupling the secondary mating member to the housing upon insertion thereof into the housing;
wherein the elastically deformable retaining component has a first engaging configuration and a second non-engaging configuration, wherein the elastically deformable retaining component is moveable into its second non-engaging configuration upon insertion of the secondary mating member into the housing to enable the secondary mating member to advance into the housing and is moveable thereafter into its first engaging configuration to couple the secondary mating member to the primary mating member preventing the secondary mating member to be detachable therefrom, preventing disengagement thereof in the absence of force to prevent the secondary mating member to be removable from the opening.

22. A releasable coupling mechanism comprising:
a housing defining a primary mating member defining an opening for receiving a secondary mating member to be coupled thereto; and
an annular elastically deformable retaining component comprising a pair of substantially straight segments coupled together at each of their respective ends by an arcuate segment, wherein a maximum deflection of the deformable retaining component occurs at a mid-point of the substantially straight segments, the annular elastically deformable retaining component being positioned within the housing, for releasably coupling the secondary mating member to the housing upon insertion thereof into the housing;
wherein the annular elastically deformable retaining component has a first engaging configuration and a second non-engaging configuration, wherein the annular elastically deformable retaining component is moveable into its second non-engaging configuration upon insertion of the secondary mating member into the housing to enable the secondary mating member to advance into the housing and is moveable thereafter into its first engaging configuration to couple the secondary mating member to the primary mating member preventing the secondary mating member to be detachable therefrom, preventing disengagement thereof in the absence of force to prevent the secondary mating member to be removable from the opening thereof.

23. The releasable coupling mechanism of claim 22, wherein the annular elastically deformable retaining component is held loosely within the housing to be retained thereby wherein the retaining component is not coupled thereto or affixed thereto by secure attachment.

24. The releasable coupling mechanism of claim 23, wherein the annular elastically deformable retaining component is free floating within the housing.

25. The releasable coupling mechanism of claim 23, wherein the annular elastically deformable retaining component is moveable in a direction that is in a plane that is perpendicular to the direction of advancement of secondary mating member into the housing for insertion therein.

26. The releasable coupling mechanism of claim 22, wherein the annular elastically deformable retaining component comprises a substantially disc shaped structure.

27. The releasable coupling mechanism of claim 26, wherein the annular elastically deformable retaining component comprises a substantially oval disc shaped structure.

28. The releasable coupling mechanism of claim 27, wherein the annular elastically deformable retaining component in its first engaging configuration comprises a substantially oval disc shaped configuration and wherein the retaining component in its second non-engaging configuration comprises a substantially circular disc shaped configuration;

wherein the annular elastically deformable retaining component is moveable into its second non-engaging configuration comprising the substantially circular disc shaped configuration upon insertion of the secondary mating member into the housing to enable the secondary mating member to advance into the housing and is moveable thereafter into its first engaging configuration comprising the substantially oval disc shaped configuration to couple the secondary mating member to the primary mating member.

29. The releasable coupling mechanism of claim 22, wherein the annular elastically deformable retaining component comprises a snap member.

30. The releasable coupling mechanism of claim 29, wherein the annular elastically deformable retaining component comprises a substantially oval snap member.

31. The releasable coupling mechanism of claim 30, wherein the annular elastically deformable retaining component in its first engaging configuration comprises the substantially oval snap member defining a substantially oval shape and wherein the annular elastically deformable retaining component in its second non-engaging configuration comprises a substantially circular snap member defining a substantially circular shape;

wherein the substantially oval snap member is moveable outwards radially into its second non-engaging configuration comprising the substantially circular shape upon insertion of the secondary mating member into the housing to enable the secondary mating member to pass past one or more snaps positioned along the substantially oval snap member and is moveable thereafter into its first engaging configuration comprising the substantially oval shape to couple the secondary mating member to the primary mating member.

32. The releasable coupling mechanism of claim 22, wherein the housing comprises a cap and cover, defining a space therein for holding the annular elastically deformable retaining component therein free from engagement therein.

* * * * *